(12) United States Patent
Han et al.

(10) Patent No.: US 6,727,366 B2
(45) Date of Patent: Apr. 27, 2004

(54) IMIDAZOLIDINONES AND THEIR RELATED DERIVATIVES AS HEPATITIS C VIRUS NS3 PROTEASE INHIBITORS

(75) Inventors: Amy Qi Han, Hockessin, DE (US); Peter W. Glunz, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/015,328

(22) Filed: Dec. 12, 2001

(65) Prior Publication Data

US 2003/0100768 A1 May 29, 2003

Related U.S. Application Data

(60) Provisional application No. 60/255,168, filed on Dec. 13, 2000.

(51) Int. Cl.[7] .................................. C07F 5/04; A61K 31/69
(52) U.S. Cl. ........................................ 548/110; 514/19
(58) Field of Search ........................... 548/323.1, 110; 514/392, 19

(56) References Cited

FOREIGN PATENT DOCUMENTS

| EP | 0471651 | 2/1992 |
|----|---------|--------|
| EP | 0932617 | 4/1998 |
| WO | WO 98/17679 | 4/1998 |
| WO | WO 99/50230 | 10/1999 |
| WO | WO 02/08198 | 1/2002 |

*Primary Examiner*—Robert W. Ramsuer
*Assistant Examiner*—Rebecca Anderson
(74) *Attorney, Agent, or Firm*—James Epperson; Scott K. Larson

(57) ABSTRACT

The present invention relates generally to a novel class of imidazolidinones of Formula (I):

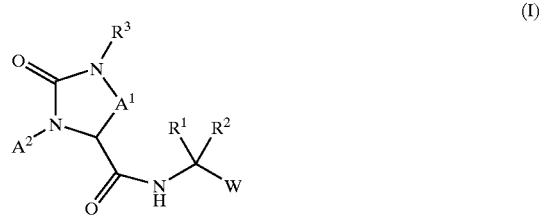

that are useful as serine protease inhibitors, and more particularly as Hepatitis C virus NS3 protease inhibitors. This invention also relates to pharmaceutical compositions comprising these compounds and methods of using the same.

4 Claims, No Drawings

IMIDAZOLIDINONES AND THEIR RELATED DERIVATIVES AS HEPATITIS C VIRUS NS3 PROTEASE INHIBITORS

FIELD OF THE INVENTION

The present invention relates generally to a novel class of imidazolidinones that are useful as serine protease inhibitors, and more particularly as Hepatitis C virus NS3 protease inhibitors. This invention also relates to pharmaceutical compositions comprising these compounds and methods of using the same.

BACKGROUND OF THE INVENTION

Hepatitis C virus (HCV) is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chroninicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard et al. *Lancet* 1998, 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus agents that inhibit NS3 proteolytic processing of the viral polyprotein are expected to have antiviral activity.

There are several patents that disclose HCV NS3 protease inhibitors. WO98/17679 describes peptide and peptidomimetic ihibitors with the following formula: $U-E^8-E^7-E^6-E^5-E^4-NH-CH(CH_2G^1)-W^1$, where W is one of a variety of electrophilic groups, including boronic acid or ester. E4 represents either an amino acid or one of a series of peptidomimetic groups, the sythesis of which are not exemplified. HCV protease inhibitors described in the present case are not covered.

Based on the large number of persons currently infected with HCV and the limited treatments available, it is desirable to discover new inhibitors of HCV NS3 protease.

SUMMARY OF THE INVENTION

One object of the present invention is to provide compounds, or pharmaceutically acceptable salt forms or prodrugs thereof, which are useful as inhibitors of hepatitis C virus protease, more specifically, the NS3 protease.

It is another object of the present invention to provide pharmaceutical compositions comprising a pharmaceutically acceptable carrier and a therapeutically effective amount of a compound of Formula (I), or pharmaceutically acceptable salt form or prodrug thereof.

It is another object of the present invention to provide a method for the treatment or prevention of HCV comprising administering to a host in need of such treatment a therapeutically effective amount of a compound of Formula (I), or a pharmaceutically acceptable salt form or prodrug thereof.

These and other objects of the invention, which will become apparent during the following detailed description, have been achieved by the discovery that compounds of Formula (I):

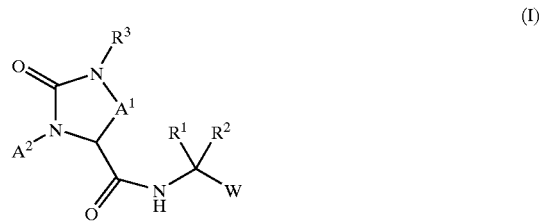

(I)

or pharmaceutically acceptable salt forms or prodrugs thereof, wherein $R^1$, $R^2$, $R^3$, W, $A^1$ and $A^2$ are defined below, are effective inhibitors of HCV NS3 protease.

It is another object of the present invention to provide a kit or container containing at least one of the compounds of the present invention in an amount effective for use as a standard or reagent in a test or assay for determining the ability of a potential pharmaceutical to inhibit HCV NS3 protease, HCV growth, or both.

It is another object of the present invention to provide novel compounds for use in therapy.

It is another object of the present invention to provide the use of novel compounds for the manufacture of a medicament for the treatment of HCV.

DETAILED DESCRIPTION OF THE INVENTION

[1] Thus, in one embodiment, the present invention provides a compound of Formula (I):

(I)

or a stereoisomer, pharmaceutically acceptable salt form or prodrug thereof, wherein:

$A^1$ is $C_1$–$C_3$ alkylene substituted by 0–2 $C_1$–$C_4$ alkyl;

$A^2$ is —C(=O)$R^{9b}$, —S(=O)$R^{9b}$, —S(=O)$_2R^{9b}$, —CONH$R^{9b}$, —S(=O)$_2$NH$R^{9b}$, —C(=O)O$R^{9b}$;

-$A^3$-$R^{9a}$;

-$A^3$-$A^4$-$R^{9a}$;

-$A^3$-$A^4$-$A^5$-$R^{9a}$; or

-$A^3$-$A^4$-$A^5$-$A^6$-$R^{9a}$;

W is selected from the group:

—B(O$R^{26}$)(O$R^{27}$),

—C(=O)C(=O)-Q,

—C(=O)C(=O)NH-Q,

—C(=O)C(=O)—O-Q,

—C(=O)CF$_2$C(=O)NH-Q,

—C(=O)CF$_3$,

—C(=O)CF$_2$CF$_3$,

—C(=O)H, and

—C(=O)$W^1$;

$W^1$ is O$R^8$ or —N$R^{11}R^{11a}$;

Q is selected from the group:

—(C$R^{10}R^{10c}$)$_m$-$Q^1$,

—(C$R^{10}R^{10c}$)$_m$-$Q^2$, $C_1$–$C_4$ alkyl substituted with $Q^1$, $C_2$–$C_4$ alkenyl substituted with $Q^1$, $C_2$–$C_4$ alkynyl substituted with $Q^1$, an amino acid residue, -$A^7$-$A^8$, and

-$A^7$-$A^8$-$A^9$;

m is 1, 2, 3, or 4;

$Q^1$ is selected from the group:

—CO$_2R^{11}$, —SO$_2R^{11}$, —SO$_3R^{11}$, —P(O)$_2R^{11}$, —P(O)$_3R^{11}$;

aryl substituted with 0–4 $Q^{1a}$; and

5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $Q^{1a}$;

$Q^{1a}$ is H, F, Cl, Br, I, —NO$_2$, —CN, —NCS, —CF$_3$, —OCF$_3$, —CO$_2R^{19}$, —C(=O)N$R^{19}R^{19a}$, —NHC(=O)$R^{19}$, —SO$_2R^{19}$, SO$_2$N$R^{19}R^{19a}$, N$R^{19}R^{19a}$, —O$R^{19}$, —S$R^{19}$, $C_1$–$C_4$ alkyl, $C_1$–$C_4$ alkoxy, $C_1$–$C_4$ haloalkyl, or $C_1$–$C_4$ haloalkoxy;

$Q^2$ is —X—N$R^{12}$-Z, —N$R^{12}$—Y-Z, or —X—N$R^{12}$—Y-Z;

X is —C(=O)—, —S—, —S(=O)—, —S(=O)$_2$—, —P(O)—, —P(O)$_2$—, or

Y is —C(=O)—, —S—, —S(=O)—, —S(=O)$_2$—, —P(O)—, —P(O)$_2$—, or —P(O)$_3$—;

Z is selected from the group:

$C_1$–$C_4$ haloalkyl;

$C_1$–$C_4$ alkyl substituted with 0–3 $Z^a$;

$C_2$–$C_4$ alkenyl substituted with 0–3 $Z^a$;

$C_2$–$C_4$ alkynyl substituted with 0–3 $Z^a$;

$C_3$–$C_{10}$ cycloalkyl substituted with 0–5 $Z^b$;

aryl substituted with 0–5 $Z^b$;

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^b$;

an amino acid residue;

-$A^7$-$A^8$, and

-$A^7$-$A^8$-$A^9$;

$Z^a$ is selected from the group:

H, F, Cl, Br, I, —NO$_2$, —CN, —NCS, —CF$_3$, —OCF$_3$, —CO$_2R^{20}$, —C(=O)N$R^2$O$R^{20a}$, —NHC(=O)$R^{20}$, —N$R^2$O$R^{20a}$, —O$R^{20}$, —S$R^{20}$, —S(=O)$R^{20}$, —SO$_2R^{20}$, —SO$_2$N$R^2$O$R^{20a}$, $C_1$–$C_4$ alkyl, $C_1$–$C_4$ haloalkyl, $C_1$–$C_4$ haloalkoxy;

$C_3$–$C_{10}$ cycloalkyl substituted with 0–5 $Z^b$;

$C_3$–$C_{10}$ carbocyle substituted with 0–5 $Z^b$;

aryl substituted with 0–5 $Z^b$; and

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^b$;

$Z^b$ is selected from the group:

H, F, Cl, Br, I, —NO$_2$, —CN, —NCS, —CF$_3$, —OCF$_3$, —CO$_2R^{20}$—C(=O)N$R^2$O$R^{20a}$, —NHC(=O)$R^{20}$, —N$R^{20}$O$R^{20a}$, —O$R^{20}$, —S$R^{20}$, —S(=O)$R^{20}$, —SO$^2R^{20}$, —SO$_2$N$R^0R^{20a}$, $C_1$–$C_4$ alkyl, $C_1$–$C_4$ haloalkyl, $C_1$–$C_4$ haloalkoxy;

$C_3$–$C_{10}$ cycloalkyl substituted with 0–5 $Z^c$;

$C_3$–$C_{10}$ carbocyle substituted with 0–5 $Z^c$;

aryl substituted with 0–5 $Z^c$; and

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^c$;

$Z^c$ is H, F, Cl, Br, I, —NO$_2$, —CN, —NCS, —CF$_3$, —OCF$_3$, —CO$_2R^{20}$, —C(=O)N$R^{20}R^{20a}$, —NHC(=O)$R^{20}$, —N$R^{20}R^{20a}$, —O$R^{20}$, —S$R^{20}$, —S(=O)$R^{20}$, —SO$_2R^{20}$, —SO$_2$N$R^{20}R^{20a}$, $C_1$–$C_4$ alkyl, $C_1$–$C_4$ haloalkyl, or $C_1$–$C_4$ haloalkoxy;

$R^1$ is selected from the group: H, F;

$C_1$–$C_6$ alkyl substituted with 0–3 $R^{1a}$;

$C_2$–$C_6$ alkenyl substituted with 0–3 $R^{1a}$;

$C_2$–$C_6$ alkynyl substituted with 0–3 $R^{1a}$; and $C_3$–$C_6$ cycloalkyl substituted with 0–3 $R^{1a}$;

$R^{1a}$ is selected at each occurrence from the group:

Cl, F, Br, I, CF$_3$, CHF$_2$, OH, =O, SH, —CO$_2R^{1b}$, —SO$_2R^{1b}$, —SO$_3R^{1b}$, P(O)$_2R^{1b}$, —P(O)$_3R^{1b}$,

—C(=O)NHR$^{1b}$, —NHC(=O)R$^{1b}$, —SO$_2$NHR$^{1b}$, —OR$^{1b}$, —SR$^{1b}$, C$_3$–C$_6$ cycloalkyl, C$_1$–C$_6$ alkoxy, —S—(C$_1$–C$_6$ alkyl);
C$_1$–C$_4$ alkyl substituted with 0–3 R$^{1c}$;
aryl substituted with 0–5 R$^{1c}$;
—O—(CH$_2$)$_n$-aryl substituted with 0–5 R$^{1c}$;
—S—(CH$_2$)$_n$-aryl substituted with 0–5 R$^{1c}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 R$^{1c}$;
n is 0, 1 or 2;
R$^{1b}$ is H;
C$_1$–C$_4$ alkyl substituted with 0–3 R$^{1c}$;
C$_2$–C$_4$ alkenyl substituted with 0–3 R$^{1c}$;
C$_2$–C$_4$ alkynyl substituted with 0–3 R$^{1c}$;
C$_3$–C$_6$ cycloalkyl substituted with 0–5 R$^{1c}$;
aryl substituted with 0–5 R$^{1c}$;
aryl-C$_1$–C$_4$ alkyl substituted with 0–4 R$^{1c}$; or
5–6 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 R$^{1c}$;
R$^{1c}$ is selected at each occurrence from the group:
C$_1$–C$_4$ alkyl, Cl, F, Br, I, OH, SH, —CN, —NO$_2$, —OR$^{1d}$, —C(=OR$^{1d}$, —NR$^{1d}$R$^{1d}$, —SO$_2$R$^{1d}$, —SO$_3$R$^{1d}$, —C(=O)NHR$^{1d}$, —NHC(=O)R$^{1d}$, —SO$_2$NHR$^{1d}$, —CF$_3$, —OCF$_3$, C$_3$–C$_6$ cycloalkyl, phenyl, and benzyl;
R$^{1d}$ is selected at each occurrence from the group: H, C$_1$–C$_4$ alkyl, phenyl and benzyl;
R$^2$ is selected from the group: H, C$_1$–C$_4$ alkyl, C$_2$–C$_4$ alkenyl, C$_2$–C$_4$ alkynyl, C$_3$–C$_4$ cycloalkyl, and C$_3$–C$_4$ cycloalkyl(C$_1$–C$_4$ alkyl)-;
alternatively, R$^1$ and R$^2$ can be combined to form a 4–7 membered cyclic group consisting of carbon atoms; substituted with 0–2 R$^{14}$;
R$^3$ is selected from the group: R$^4$,
—(CH$_2$)$_p$—NH—R$^4$,
—(CH$_2$)$_p$—NHC(=O)—R$^4$,
—(CH$_2$)$_p$—C(=O)NH—R$^4$,
—(CH$_2$)$_p$—C(=O)O—R$^4$,
—(CH$_2$)$_p$—C(=O)C(=O)—R$^4$,
—(CH$_2$)$_p$—C(=O)C(=O)NH—R$^4$,
—(CH$_2$)$_p$—NHC(=O)NH—R$^4$,
—(CH$_2$)$_p$—NHC(=O)NHC(=O)—R$^4$,
—(CH$_2$)$_p$—NHS(~0)$_2$—R$^4$,
—(CH$_2$)$_p$—S(=O)$_2$NH—R$^4$,
—(CH$_2$)$_p$—C(=O) —R$^4$,
—(CH$_2$)$_p$—O—R$^4$, and
—(CH$_2$)$_p$—S—R$^4$;
p is 0, 1, or 2;
R$^4$ is selected from the group:
C$_1$–C$_6$ alkyl substituted with 0–3 R$^{4a}$;
C$_2$–C$_6$ alkenyl substituted with 0–3 R$^{4a}$;
C$_2$–C$_6$ alkynyl substituted with 0–3 R$^{4a}$;
C$_3$–C$_{10}$ cycloalkyl substituted with 0–4 R$^{4b}$;
C$_3$–C$_{10}$ carbocycle substituted with 0–4 R$^{4b}$;
aryl substituted with 0–5 R$^{4b}$;
aryl-C$_1$–C$_4$ alkyl substituted with 0–5 R$^{4b}$; and
5–10 membered heterocyclic group consisting of carbon atoms and 1–4 heteroatoms selected from the group: O, S, and N; optionally saturated, partially unsaturated or unsaturated; and said 5-10 membered heterocyclic group is substituted with 0–4 R$^{4b}$;
R$^{4a}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, OR$^{11a}$, SR$^{11a}$, —C(=O)R$^{11a}$, —S(=O)R$^{11a}$, —SO$_2$R$^{11}$, —SO$_2$NR$^{11}$R$^{11a}$, —NHC(=NH)NHR$^{11}$, —C(=NH)NHR$^{11}$, =NOR$^{11}$, —NR$^{11}$C(=O)OR$^{11a}$, NR$^{11}$C(=O)NR$^{11}$R$^{11a}$, —NR$^{11}$SO$_2$NR$^{11}$R$^{11a}$, NR$^{11}$SO$_2$R$^{11a}$, —OP(O)(OR$^{11}$)$_2$;
C$_1$–C$_4$ alkyl substituted with 0–3 R$^{4b}$;
C$_2$–C$_4$ alkenyl substituted with 0–3 R$^{4b}$;
C$_2$–C$_4$ alkynyl substituted with 0–3 R$^{4b}$;
C$_3$–C$_7$ cycloalkyl substituted with 0–4 R$^{4c}$;
C$_3$–C$_{10}$ carbocycle substituted with 0–4 R$^{4c}$;
aryl substituted with 0–5 R$^{4c}$; and
5–10 membered heterocyclic group consisting of carbon atoms and 1–4 heteroatoms selected from the group: O, S, and N; optionally saturated, partially unsaturated or unsaturated; and said 5-10 membered heterocyclic group is substituted with 0–3 R$^{4c}$;
R$^{4b}$ is, at each occurrence, independently selected from:
H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, OR$^{11a}$, SR$^{11a}$, —C(=O)R$^{11a}$, —S(=O)R$^{11a}$, —SO$_2$R$^{11}$, —SO$_2$NR$^{11}$R$^{11a}$, —NHC(=NH)NHR$^{11}$, —C(=NH)NHR$^{11}$, =NOR$^{11}$, —NR$^{11}$C(=O)OR$^{11a}$, —OC(=O)NR$^{11}$R$^{11a}$, —NR$^{11}$C(=O)NR$^{11}$R$^{11a}$, —NR$^{11}$SO$_2$NR$^{11}$R$^{11a}$, —NR$^{11}$SO$_2$R$^{11a}$, —OP(O)(OR$^{11}$)$_2$;
C$_1$–C$_4$ alkyl substituted with 0–3 R$^{4c}$;
C$_2$–C$_4$ alkenyl substituted with 0–3 R$^{4c}$;
C$_2$–C$_4$ alkynyl substituted with 0–3 R$^{4c}$;
C$_3$–C$_6$ cycloalkyl substituted with 0–4 R$^{4d}$;
aryl substituted with 0–5 R$^{4d}$; and
5–10 membered heterocyclic group consisting of carbon atoms and 1–4 heteroatoms selected from the group: O, S, and N; optionally saturated or unsaturated; and said 5–10 membered heterocyclic group is substituted with 0–3 R$^{4d}$;
R$^{4c}$ is, at each occurrence, independently selected from:
H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, SR$^{11a}$, —C(=O)R$^{11a}$, —S(=O)R$^{11a}$, —SO$_2$R$^{11}$—SO$_2$NR$^{11}$R$^{11a}$,
C$_1$–C$_4$ haloalkyl, C$_1$–C$_4$ haloalkoxy;
C$_1$–C$_4$ alkyl substituted with 0–3 R$^{4d}$;
C$_2$–C$_4$ alkenyl substituted with 0–3 R$^{4d}$;
C$_2$–C$_4$ alkynyl substituted with 0–3 R$^{4d}$;
C$_3$–C$_6$ cycloalkyl substituted with 0–4 R$^{4d}$;
aryl substituted with 0–5 R$^{4d}$; and
5–10 membered heterocyclic group consisting of carbon atoms and 1–4 heteroatoms selected from the group: O, S, and N; optionally saturated or unsaturated; and said 5–10 membered heterocyclic group is substituted with 0–3 R$^{4d}$;

$R^{4d}$ is, at each occurrence, independently selected from:
  H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, $NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^8$ is H or $C_1$–$C_4$ alkyl;

$R^{9a}$ is selected from the group: H, —S(=O)$R^{9b}$, —S(=O)$_2R^{9b}$, —S(=O)$_2NHR^{9b}$, —C(=O)$R^{9b}$, —C(=O)$OR^{9b}$, —C(=O)$NHR^{9b}$, —C(=O)NHC(=O)$R^{9b}$;
  $C_1$–$C_6$ alkyl substituted with 0–3 $R^{9c}$;
  $C_2$–$C_6$ alkenyl substituted with 0–3 $R^{9c}$;
  $C_2$–$C_6$ alkynyl substituted with 0–3 $R^{9c}$;
  $C_3$–$C_6$ cycloalkyl substituted with 0–3 $R^{9d}$;
  $C_3$–$C_{14}$ carbocycle substituted with 0–4 $R^{9d}$;
  aryl substituted with 0–5 R9d; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 R9d;

$R^{9b}$ is selected from the group: H;
  $C_1$–$C_6$ alkyl substituted with 0–3 $R^{9c}$;
  $C_2$–$C_6$ alkenyl substituted with 0–3 $R^{9c}$;
  $C_2$–$C_6$ alkynyl substituted with 0–3 $R^{9c}$;
  $C_3$–$C_6$ cycloalkyl substituted with 0–3 $R^{9d}$;
  $C_3$–$C_{14}$ carbocycle substituted with 0–4 $R^{9d}$;
  aryl substituted with 0–5 $R^{9d}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9c}$ is selected from the group: $CF_3$, $OCF_3$, Cl, F, Br, I, =O, OH, c(O)$OR^{11}$, $NH_2$, $NH(CH_3)$, $N(CH_3)_2$, —CN, $NO_2$;
  $C_1$–$C_6$ alkyl substituted with 0–3 $R^{9d}$;
  $C_2$–$C_6$ alkenyl substituted with 0–3 $R^{9d}$;
  $C_2$–$C_6$ alkynyl substituted with 0–3 $R^{9d}$;
  $C_3$–$C_6$ cycloalkyl substituted with 0–3 $R^{9e}$;
  $C_3$–$C_{14}$ carbocycle substituted with 0–4 $R^{9e}$;
  aryl substituted with 0–5 $R^9e$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9e}$;

$R^{9d}$ is selected at each occurrence from the group:
  $CF_3$, $OCF_3$, Cl, F, Br, I, =O, OH, C(O)$OR^{11}$, $NH_2$, $NH(CH_3)$, $N(CH_3)_2$, —CN, $NO_2$;
  $C_1$–$C_4$ alkyl substituted with 0–3 $R^{9e}$;
  $C_1$–$C_4$ alkoxy substituted with 0–3 $R^{9e}$;
  $C_3$–$C_6$ cycloalkyl substituted with 0–3 $R^{9e}$;
  aryl substituted with 0–5 $R^{9e}$; and
  5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $R^{9e}$;

$R^{9e}$ is selected at each occurrence from the group:
  $C_1$–$C_4$ alkyl, $C_1$–$C_4$ alkoxy, $CF_3$, $OCF_3$, Cl, F, Br, I, =O, OH, phenyl, C(O)$OR^{11}$, $NH_2$, $NH(CH_3)$, $N(CH_3)_2$, —CN, and $NO_2$;

$R^{10}$ is selected from the group: —$CO_2R^{11}$, —$NR^{11}R^{11a}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, $NR^{11}R^{11a}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ and $R^{11a}$ are, at each occurrence, independently selected from the group: H;
  $C_1$–$C_6$ alkyl substituted with 0–3 $R^{11b}$;
  $C_2$–$C_6$ alkenyl substituted with 0–3 $R^{11b}$;
  $C_2$–$C_6$ alkynyl substituted with 0–3 $R^{11b}$;
  $C_3$–$C_7$ cycloalkyl substituted with 0–3 $R^{11b}$;
  aryl substituted with 0–3 $R^{11b}$; and
  aryl($C_1$–$C_4$ alkyl)-substituted with 0–3 $R^{11b}$;

$R^{11b}$ is OH, $C_1$–$C_4$ alkoxy, F, Cl, Br, I, $NH_2$, or —NH($C_1$–$C_4$ alkyl);

$R^{12}$ is H or $C_1$–$C_4$ alkyl;

$R^{14}$ is $C_1$–$C_4$ alkyl or $C_2$–$C_4$ alkenyl;

$R^{19}$ and $R^{19a}$ are independently selected from the group: H, $C_1$–$C_4$ alkyl, $C_1$–$C_4$ haloalkyl, aryl, aryl($C_1$–$C_4$ alkyl), $C_3$–$C_6$ cycloalkyl, and $C_3$–$C_6$ cycloalkyl($C_1$–$C_4$ alkyl);

alternatively, $NR^{19}R^{19a}$ may form a 5–6 membered heterocyclic group consisting of carbon atoms, a nitrogen atom, and optionally a second heteroatom selected from the group: O, S, and N;

$R^{20}$ and $R^{20a}$ are independently selected from the group: H, $C_1$–$C_4$ alkyl, $C_1$–$C_4$ haloalkyl, aryl, aryl($C_1$–$C_4$ alkyl)-, $C_3$–$C_6$ cycloalkyl, and $C_3$–$C_6$ cycloalkyl($C_1$–$C_4$ alkyl)-;

alternatively, $NR^{20}R^{20a}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
  a) —OH,
  b) —F,
  c) —$NR^{28}R^{29}$,
  d) $C_1$–$C_8$ alkoxy, and
when taken together, $OR^{26}$ and $OR^{27}$ form:
  e) a cyclic boronic ester where said cyclic boronic ester contains from 2 to 20 carbon atoms, and, optionally, 1, 2, or 3 heteroatoms which can be N, S, or O;
  f) a cyclic boronic amide where said boronic amide contains from 2 to 20 carbon atoms and, optionally, 1, 2, or 3 heteroatoms which can be N, S, or O; or
  g) a cyclic boronic amide-ester where said boronic amide-ester contains from 2 to 20 carbon atoms and, optionally, 1, 2, or 3 heteroatoms which can be N, S, or O;

$R^{28}$ and $R^{29}$, are independently selected from: H, $C_1$–$C_4$ alkyl, aryl($C_1$–$C_4$ alkyl)-, and $C_3$–$C_7$ cycloalkyl;

$A^3$, $A^4$, $A^5$, $A^6$, $A^7$, $A^8$, and $A^9$ are independently selected from an amino acid residue; and an amino acid residue, at each occurence, independently comprises a natural amino acid, a modified amino acid or an unnatural amino acid wherein said natural, modified or unnatural amino acid is of either D or L configuration.

[2] In another embodiment, the present invention provides a compound of Formula (I) or a pharmaceutically acceptable salt or prodrug thereof, wherein:

$A^1$ is —$CH_2$— or —$CH_2CH_2$—;

$A^2$ is —C(=O)$R^{9b}$, —S(=O)$R^{9b}$, —S(=O)$_2R^{9b}$, —CONH$R^{9b}$, —S(=O)$_2NHR^{9b}$, —C(=O)$OR^{9b}$;

—$A^3$—$R^{9a}$;
—$A^3$—$A^4$—$R^{9a}$;
—$A^3$—$A^4$—$A^5$—$R^{9a}$; or
—$A^3$—$A^4$—$A^5$—$A^6$—$R^{9a}$;

W is selected from the group:
- —$B(OR^{26})(OR^{27})$,
- —$C(=O)C(=O)$—Q,
- —$C(=O)C(=O)NH$—Q,
- —$C(=O)C(=O)$—O—Q,
- —$C(=O)CF_2C(=O)NH$—Q,
- —$C(=O)CF_3$,
- —$C(=O)CF_2CF_3$,
- —$C(=O)H$, and
- —$C(=O)W^1$;

$W^1$ is $OR^8$ or —$NR^{11}R^{11a}$;

Q is selected from the group:
- —$(CR^{10}R^{10c})_m$—$Q^1$,
- $C_1$–$C_4$ alkyl substituted with $Q^1$,
- $C_2$–$C_4$ alkenyl substituted with $Q^1$, and
- $C_2$–$C_4$ alkynyl substituted with $Q^1$;

m is 1 or 2;

$Q^1$ is selected from the group:
- —$CO_2R^{11}$, —$SO_2R^{11}$, —$SO_3R^{11}$, —$P(O)_2R^{11}$, —$P(O)_3R^{11}$;
- phenyl substituted with 0–4 $Q^{1a}$; and
- 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $Q^{1a}$;

$Q^{1a}$ is H, F, Cl, Br, I, —$NO_2$, —CN, —NCS, —$CF_3$, —$OCF_3$, —$CO_2R^{19}$, —$C(=O)NR^{19}R^{19a}$, —$NHC(=O)R^{19}$, —$SO_2R^{19}$, $SO_2NR^{19}R^{19a}$, —$NR^{19}R^{19a}$, —$OR^{19}$, —$SR^{19}$, $C_1$–$C_4$ alkyl, $C_1$–$C_4$ alkoxy, $C_1$–$C_4$ haloalkyl, or $C_1$–$C_4$ haloalkoxy;

$R^1$ is selected from the group: H, F;
- $C_1$–$C_6$ alkyl substituted with 0–3 $R^{1a}$;
- $C_2$–$C_6$ alkenyl substituted with 0–3 $R^{1a}$;
- $C_2$–$C_6$ alkynyl substituted with 0–3 $R^{1a}$; and
- $C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH, —$CO_2R^{1b}$, —$SO_2R^{1b}$, —$SO_3R^{1b}$, $P(O)_2R^{1b}$, —$P(O)_3R^{1b}$, —$C(=O)NHR^{1b}$,
—$NHC(=O)R^{1b}$, —$SO_2NHR^{1b}$, —$OR^{1b}$, —$SR^{1b}$, $C_3$–$C_6$ cycloalkyl, $C_1$–$C_6$ alkoxy, —S—($C_1$–$C_6$ alkyl);
$C_1$–$C_4$ alkyl substituted with 0–3 $R^{1c}$;
aryl substituted with 0–5 $R^{1c}$;
—O—$(CH_2)_n$-aryl substituted with 0–5 $R^{1c}$;
—S—$(CH_2)_n$-aryl substituted with 0–5 $R^{1c}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{1c}$;

n is 0, 1 or 2;

$R^{1b}$ is H;
- $C_1$–$C_4$ alkyl substituted with 0–3 $R^{1c}$;
- $C_2$–$C_4$ alkenyl substituted with 0–3 $R^{1c}$;
- $C_2$–$C_4$ alkynyl substituted with 0–3 $R^{1c}$;
- $C_3$–$C_6$ cycloalkyl substituted with 0–5 $R^{1c}$;
- aryl substituted with 0–5 $R^{1c}$;
- aryl-$C_1$–$C_4$ alkyl substituted with 0–4 $R^{1c}$; or
- 5–6 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{1c}$;

$R^{1c}$ is selected at each occurrence from the group:
$C_1$–$C_4$ alkyl, Cl, F, Br, I, OH, SH, —CN, —$NO_2$, —$OR^{1d}$, —$C(=O)OR^{1d}$, —$R^{1d}R^{1d}$, —$SO_2R^{1d}$, —$SO_3R^{1d}$, —$C(=O)NHR^{1d}$, —$NHC(=O)R^{1d}$, —$SO_2NHR^{1d}$, —$CF_3$, —$OCF_3$, $C_3$–$C_6$ cycloalkyl, phenyl, and benzyl;

$R^{1d}$ is selected at each occurrence from the group: H, $C_1$–$C_4$ alkyl, phenyl and benzyl;

$R^2$ is selected from the group: H, $C_1$–$C_4$ alkyl, $C_2$–$C_4$ alkenyl, $C_2$–$C_4$ alkynyl, $C_3$–$C_4$ cycloalkyl, and $C_3$–$C_4$ cycloalkyl($C_1$–$C_4$ alkyl)-; alternatively, $R^1$ and $R^2$ can be combined to form a 4–7 membered cyclic group consisting of carbon atoms; substituted with 0–2 $R^{14}$;

$R^3$ is selected from the group: $R^4$,
- —$(CH_2)_p$—NH—$R^4$,
- —$(CH_2)_p$—NHC(=O)—$R^4$,
- —$(CH_2)_p$—C(=O)NH—$R^4$,
- —$(CH_2)_p$—C(=O)O—$R^4$,
- —$(CH_2)_p$—C(=O)C(=O)—$R^4$,
- —$(CH_2)_p$—C(=O)C(=O)NH—$R^4$,
- —$(CH_2)_p$—NHC(=O)NH—$R^4$,
- —$(CH_2)_p$—NHC(=O)NHC(=O)—$R^4$,
- —$(CH_2)_p$—NHS(=O)$_2$—$R^4$,
- —$(CH_2)_p$—S(=O)$_2$NH—$R^4$,
- —$(CH_2)_p$—C(=O)—$R^4$,
- —$(CH_2)_p$—O—$R^4$, and
- —$(CH_2)_p$—S—$R^4$;

p is 0, 1, or 2;

$R^4$ is selected from the group:
- $C_1$–$C_6$ alkyl substituted with 0–3 $R^{4a}$;
- $C_2$–$C_6$ alkenyl substituted with 0–3 $R^{4a}$;
- $C_2$–$C_6$ alkynyl substituted with 0–3 $R^{4a}$;
- $C_3$–$C_{10}$ cycloalkyl substituted with 0–4 $R^{4b}$;
- $C_3$–$C_{10}$ carbocycle substituted with 0–4 $R^{4b}$;
- aryl substituted with 0–5 $R^{4b}$;
- aryl-$C_1$–$C_4$ alkyl substituted with 0–5 $R^{4b}$; and
- 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, =O, OH, —$CO_2H$, —$C(=NH)NH_2$, —$CO_2R^{11}$, —$C(=O)NR^{11}R^{11a}$, —$NHC(=O)R^{11}$, —$NR^{11}R^{11a}$, —$OR^{11a}$, —$SR^{11a}$, —$C(=O)R^{11a}$, —$S(=O)R^{11a}$, —$SO_2R^{11}$, —$SO_2NR^{11}R^{11a}$, —$NHC(=NH)NHR^{11}$, —$C(=NH)NHR^{11}$, =$NOR^{11}$, —$NR^{11}C(=O)OR^{11a}$, $NR^{11}C(=O)NR^{11}R^{11a}$, —$NR^{11}SO_2NR^{11}R^{11a}$, —$NR^{11}SO_2R^{11a}$, —$OP(O)(OR^{11})_2$;
$C_1$–$C_4$ alkyl substituted with 0–3 $R^{4b}$;
$C_2$–$C_4$ alkenyl substituted with 0–3 $R^{4b}$;
$C_2$–$C_4$ alkynyl substituted with 0–3 $R^{4b}$;
$C_3$–$C_7$ cycloalkyl substituted with 0–4 $R^{4c}$;
$C_3$–$C_{10}$ carbocycle substituted with 0–4 $R^{4c}$;

aryl substituted with 0–5 $R^{4c}$; and

5–10 membered heterocyclic group consisting of carbon atoms and 1–4 heteroatoms selected from the group: O, S, and N; optionally saturated, partially unsaturated or unsaturated; and said 5-10 membered heterocyclic group is substituted with 0–3 $R^{4c}$;

$R^{4b}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, $OR^{11a}$, $SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$C(=O)$OR^{11a}$, OC(=O)$NR^{11}R^{11a}$, $NR^{11}$C(=O)$NR^{11}R^{11a}$, —$NR^{11}SO_2NR^{11}R^{11a}$, —$NR^{11}SO_2R^{11a}$, —OP(O)($OR^{11}$)$_2$;

$C_1$–$C_4$ alkyl substituted with 0–3 $R^{4c}$;

$C_2$–$C_4$ alkenyl substituted with 0–3 $R^{4c}$;

$C_2$–$C_4$ alkynyl substituted with 0–3 $R^{4c}$;

$C_3$–$C_6$ cycloalkyl substituted with 0–4 $R^{4d}$;

aryl substituted with 0–5 $R^{4d}$; and

5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4c}$ is, at each occurrence, independently selected from:

H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=OCO)$R^{11}$, —$NR^{11}R^{11a}$, $OR^{11a}$, $SR^{11a}$, —C(=O)$R^{11a}$, —S(=O)$R^{11a}$, —$SO_2R^{11}$, $SO_2NR^{11}R^{11a}$, $C_1$–$C_4$ haloalkyl, $C_1$–$C_4$ haloalkoxy;

$C_1$–$C_4$ alkyl substituted with 0–3 $R^{4d}$;

$C_2$–$C_4$ alkenyl substituted with 0–3 $R^{4d}$;

$C_2$–$C_4$ alkynyl substituted with 0–3 $R^{4d}$;

$C_3$–$C_6$ cycloalkyl substituted with 0–4 $R^{4d}$;

aryl substituted with 0–5 $R^{4d}$; and

5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4d}$ is, at each occurrence, independently selected from:

H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^8$ is H or $C_1$–$C_4$ alkyl;

$R^{9a}$ is selected from the group: H, —S(=O)$R^{9b}$, —S(=O)$_2R^{9b}$, —S(=O)$_2NHR^{9b}$, —C(=O)$R^{9b}$, —C(=O)$OR^{9b}$, —C(=O)$NHR^{9b}$, —C(=O)NHC(=O)$R^{9b}$;

$C_1$–$C_6$ alkyl substituted with 0–3 $R^{9c}$;

$C_2$–$C_6$ alkenyl substituted with 0–3 $R^{9c}$;

$C_2$–$C_6$ alkynyl substituted with 0–3 $R^{9c}$;

$C_3$–$C_6$ cycloalkyl substituted with 0–3 $R^{9d}$;

$C_3$–$C_{14}$ carbocycle substituted with 0–4 $R^{9d}$;

aryl substituted with 0–5 $R^{9d}$; and

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9b}$ is selected from the group: H;

$C_1$–$C_6$ alkyl substituted with 0–3 $R^{9c}$;

$C_2$–$C_6$ alkenyl substituted with 0–3 $R^{9c}$;

$C_2$–$C_6$ alkynyl substituted with 0–3 $R^{9c}$;

$C_3$–$C_6$ cycloalkyl substituted with 0–3 $R^{9d}$;

$C_3$–$C_{14}$ carbocycle substituted with 0–4 $R^{9d}$;

aryl substituted with 0–5 $R^{9d}$; and

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9c}$ is selected from the group: $CF_3$, $OCF_3$, Cl, F, Br, I, =O, OH, C(O)$OR^{11}$, $NH_2$, NH($CH_3$), N($CH_3$)$_2$, —CN, $NO_2$;

$C_1$–$C_6$ alkyl substituted with 0–3 $R^{9d}$;

$C_2$–$C_6$ alkenyl substituted with 0–3 $R^{9d}$;

$C_2$–$C_6$ alkynyl substituted with 0–3 $R^{9d}$;

$C_3$–$C_6$ cycloalkyl substituted with 0–3 $R^{9e}$;

$C_3$–$C_{14}$ carbocycle substituted with 0–4 $R^{9e}$;

aryl substituted with 0–5 $R^{9e}$; and

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9e}$;

$R^{9d}$ is selected at each occurrence from the group:

$CF_3$, $OCF_3$, Cl, F, Br, I, =O, OH, C(O)$OR^{11}$, $NH_2$, NH($CH_3$), N($CH_3$)$_2$, —CN, $NO_2$;

$C_1$–$C_4$ alkyl substituted with 0–3 $R^{9e}$;

$C_1$–$C_4$ alkoxy substituted with 0–3 $R^{9e}$;

$C_3$–$C_6$ cycloalkyl substituted with 0–3 $R^{9e}$;

aryl substituted with 0–5 $R^{9e}$; and

5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $R^{9e}$;

$R^{9e}$ is selected at each occurrence from the group:

$C_1$–$C_4$ alkyl, $C_1$–$C_4$ alkoxy, $CF_3$, $OCF_3$, Cl, F, Br, I, =O, OH, phenyl, C(O)$O^{11}$, $NH_2$, NH($CH_3$), N($CH_3$)$_2$, —CN, and $NO_2$;

$R^{10}$ is selected from the group: —$CO_2R^{11}$, —$NR^{11}R^{11a}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, $NR^{11}R^{11a}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ and $R^{11a}$ are, at each occurrence, independently selected from the group: H;

$C_1$–$C_6$ alkyl substituted with 0–3 $R^{11b}$;

$C_2$–$C_6$ alkenyl substituted with 0–3 $R^{11b}$;

$C_2$–$C_6$ alkynyl substituted with 0–3 $R^{11b}$;

$C_3$–$C_7$ cycloalkyl substituted with 0–3 $R^{11b}$;

aryl substituted with 0–3 $R^{11b}$; and aryl($C_1$–$C_4$ alkyl)-substituted with 0–3 $R^{11b}$;

$R^{11b}$ is OH, $C_1$–$C_4$ alkoxy, F, Cl, Br, I, $NH_2$, or —NH($C_1$–$C_4$ alkyl);

$R^{12}$ is H or $C_1$–$C_4$ alkyl;

$R^{14}$ is $C_1$–$C_4$ alkyl or $C_2$–$C_4$ alkenyl;

$R^{19}$ and $R^{19a}$ are independently selected from the group: H, $C_1$–$C_4$ alkyl, $C_1$–$C_4$ haloalkyl, aryl, aryl($C_1$–$C_4$ alkyl), $C_3$–$C_6$ cycloalkyl, and $C_3$–$C_6$ cycloalkyl($C_1$–$C_4$ alkyl);

alternatively, $NR^{19}R^{19a}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
 a) —OH,
 b) —F,
 c) —$NR^{28}R^{29}$,
 d) $C_1$–$C_8$ alkoxy, and when taken together, $OR^{26}$ and $OR^{27}$ form:
 e) a cyclic boronic ester where said cyclic boronic ester contains from 2 to 20 carbon atoms, and, optionally, 1, 2, or 3 heteroatoms which can be N, S, or O;

$R^{28}$ and $R^{29}$, are independently selected from: H, $C_1$–$C_4$ alkyl, aryl($C_1$–$C_4$ alkyl)-, and $C_3$–$C_7$ cycloalkyl;

$A^3$, $A^4$, $A^5$, and $A^6$, are independently selected from an amino acid residue; and an amino acid residue, at each occurence, independently comprises a natural amino acid, a modified amino acid or an unnatural amino acid wherein said natural, modified or unnatural amino acid is of either D or L configuration.

[3] In an alternative embodiment, the present invention provides a compound of Formula (I) or a pharmaceutically acceptable salt or prodrug thereof, wherein:

$A^1$ is —$CH_2$— or —$CH_2CH_2$—;
$A^2$ is —C(=O)$R^{9b}$, —S(=O)$R^{9b}$, —S(=O)$_2R^{9b}$, —CONH$R^{9b}$, —S(=O)$_2$NH$R^{9b}$, —C(=O)O$R^{9b}$;
 —$A^3$—$R^{9a}$;
 —$A^3$—$A^4$—$R^{9a}$; or
 —$A^3$—$A^4$—$A^5$—$R^{9a}$;

W is —B(O$R^{26}$)(O$R^{27}$);

$R^1$ is selected from the group: H;
 $C_1$–$C_4$ alkyl substituted with 0–2 $R^{1a}$;
 $C_2$–$C_4$ alkenyl substituted with 0–2 $R^{1a}$;
 $C_2$–$C_4$ alkynyl substituted with 0–2 $R^{1a}$; and $R^{1a}$ is selected at each occurrence from the group:
 Cl, F, Br, $CF_3$, $CHF_2$, OH, $C_3$–$C_6$ cycloalkyl, $C_1$–$C_4$ alkoxy, —S—($C_1$–$C_4$ alkyl);
 $C_1$–$C_4$ alkyl substituted with 0–2 $R^{1c}$;
 aryl substituted with 0–3 $R^{1c}$; and
 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{1c}$;

$R^{1c}$ is selected at each occurrence from the group:
 $C_1$–$C_4$ alkyl, Cl, F, Br, I, OH, SH, —CN, —$NO_2$, —O$R^{1d}$, —C(=O)O$R^{1d}$, —$NR^{1d}R^{1d}$, —$SO_2R^{1d}$, —$SO_3R^{1d}$, —C(=O)NH$R^{1d}$, —NHC(=O)$R^{1d}$, —$SO_2$NH$R^{1d}$, —$CF_3$, —$OCF_3$, $C_3$–$C_6$ cycloalkyl, phenyl, and benzyl;

$R^{1d}$ is selected at each occurrence from the group: H, $C_1$–$C_4$ alkyl, phenyl and benzyl;

$R^2$ is H or $C_1$–$C_4$ alkyl;

$R^3$ is selected from the group: $R^4$,
 —$(CH_2)_p$—NH—$R^4$,
 —$(CH_2)_p$—NHC(=O)—$R^4$,
 —$(CH_2)_p$—C(=O)NH—$R^4$,
 —$(CH_2)_p$—C(=O)O—$R^4$,
 —$(CH_2)_p$—NHC(=O)NH—$R^4$,
 —$(CH_2)_p$—NHC(=O)NHC(=O)—R
 —$(CH_2)_p$—C(=O) —$R^4$,
 —$(CH_2)_p$—O—$R^4$, and
 —$(CH_2)_p$—S—$R^4$;

p is 0, 1, or 2;

$R^4$ is selected from the group:
 $C_1$–$C_4$ alkyl substituted with 0–3 $R^{4a}$;
 $C_2$–$C_4$ alkenyl substituted with 0–3 $R^{4a}$;
 $C_2$–$C_4$ alkynyl substituted with 0–3 $R^{4a}$;
 $C_3$–$C_6$ cycloalkyl substituted with 0–2 $R^{4b}$;
 aryl substituted with 0–5 $R^{4b}$; and
 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{4b}$;

$R^{4a}$ is, at each occurrence, independently selected from:
 H, F, Cl, Br, I, —$NO_2$, —CN, —NCS, —$CF_3$, —$OCF_3$, =O, OH, —$CO_2$H, —C(=NH)$NH_2$, —$CO_2R^{11}$, —C(=O)$NR^{11}R^{11a}$, —NHC(=O)$R^{11}$, —$NR^{11}R^{11a}$, $OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —$NR^{11}C(=O)NR^{11}R^{11a}$, —$NR^{11}SO_2NR^{11}R^{11a}$, —$NR^{11}SO_2R^{11a}$;
 $C_1$–$C_4$ alkyl substituted with 0–2 $R^{4b}$;
 $C_2$–$C_4$ alkenyl substituted with 0–2 $R^{4b}$;
 $C_2$–$C_4$ alkynyl substituted with 0–2 $R^{4b}$;
 $C_3$–$C_7$ cycloalkyl substituted with 0–3 $R^{4c}$; aryl substituted with 0–5 $R^{4c}$; and
 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{4c}$;

$R^{4b}$ is, at each occurrence, independently selected from:
 H, F, Cl, Br, I, —$NO_2$, —CN, —NCS, —$CF_3$, —$OCF_3$, =O, OH, —$CO_2$H, —C (=NH)$NH_2$, —$CO_2R^{11}$, —C(=O)$NR^{11}R^{11a}$, —NHC(=O)$R^{11}$, —$NR^{11}R^{11a}$, —$OR^{11a}$, $SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, $OC(=O)NR^{11}R^{11a}$, —$NR^{11}C(=O)NR^{11}R^{11a}$, —$NR^{11}SO_2NR^{11}R^{11a}$, —$NR^{11}SO_2R^{11a}$, —OP(O)($OR^{11}$)$_2$;
 $C_1$–$C_4$ alkyl substituted with 0–3 $R^{4c}$;
 $C_2$–$C_4$ alkenyl substituted with 0–3 $R^{4c}$;
 $C_2$–$C_4$ alkynyl substituted with 0–3 $R^{4c}$;
 $C_3$–$C_6$ cycloalkyl substituted with 0–4 $R^{4d}$;
 aryl substituted with 0–5 $R^{4d}$; and
 5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4c}$ is, at each occurrence, independently selected from:
 H, F, Cl, Br, I, —$NO_2$, —CN, —NCS, —$CF_3$, —$OCF_3$, =O, OH, —$CO_2$H, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1-C_4$ haloalkyl, $C_1-C_4$ haloalkoxy;
$C_1-C_4$ alkyl substituted with 0–3 $R^{4d}$;
$C_2-C_4$ alkenyl substituted with 0–3 $R^{4d}$;
$C_2-C_4$ alkynyl substituted with 0–3 $R^{4d}$;
$C_3-C_6$ cycloalkyl substituted with 0–4 $R^{4d}$;
aryl substituted with 0–5 $R^{4d}$; and
5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, =O, OH, —$CO_2H$, —$CO_2R^{11}$, —$C(=O)NR^{11}R^{11a}$, —$NHC(=O)R^{11}$, $NR^{11}R^{11a}$, —$OR^{11a}$, $SR^{11a}$, —$C(=O)R^{11a}$, —$S(=O)R^{11a}$, —$SO_2R^{11}$, —$SO_2NR^{11}R^{11a}$, $C_1-C_4$ alkyl, $C_1-C_4$ alkoxy, $C_1-C_4$ haloalkyl, $C_1-C_4$ haloalkoxy, phenyl, and benzyl;

$R^{9a}$ is selected from the group: H, —$S(=O)R^{9b}$, —$S(=O)_2R^{9b}$, —$S(=O)_2NHR^{9b}$, —$C(=O)R^{9b}$, —$C(=O)OR^{9b}$, —$C(=O)NHR^{9b}$, —$C(=O)NHC(=O)R^{9b}$;
$C_1-C_4$ alkyl substituted with 0–3 $R^{9c}$;
$C_2-C_4$ alkenyl substituted with 0–3 $R^{9c}$;
$C_2-C_4$ alkynyl substituted with 0–3 $R^{9c}$;
$C_3-C_6$ cycloalkyl substituted with 0–3 $R^{9d}$;
$C_3-C_{14}$ carbocycle substituted with 0–4 $R^{9d}$;
aryl substituted with 0–5 $R^{9d}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9b}$ is selected from the group: H;
$C_1-C_4$ alkyl substituted with 0–2 $R^{9c}$;
$C_2-C_4$ alkenyl substituted with 0–2 $R^{9c}$;
$C_2-C_4$ alkynyl substituted with 0–2 $R^{9c}$;
$C_3-C_6$ cycloalkyl substituted with 0–2 $R^{9d}$;
$C_3-C_{14}$ carbocycle substituted with 0–3 $R^{9d}$;
aryl substituted with 0–3 $R^{9d}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{9d}$;

$R^{9c}$ is selected from the group: $CF_3$, $OCF_3$, Cl, F, Br, I, =O, OH, $C(O)OR^{11}$, $NH_2$, $NH(CH_3)$, $N(CH_3)_2$, —CN, $NO_2$;
$C_1-C_4$ alkyl substituted with 0–3 $R^{9d}$;
$C_2-C_4$ alkenyl substituted with 0–3 $R^{9d}$;
$C_2-C_4$ alkynyl substituted with 0–3 $R^{9d}$;
$C_3-C_6$ cycloalkyl substituted with 0–3 $R^{9e}$;
$C_3-C_{14}$ carbocycle substituted with 0–4 $R^{9e}$;
aryl substituted with 0–5 $R^{9e}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9e}$;

$R^{9d}$ is selected at each occurrence from the group:
$CF_3$, $OCF_3$, Cl, F, Br, I, =O, OH, $C(O)OR^{11}$, $NH_2$, $NH(CH_3)$, $N(CH_3)_2$, —CN, $NO_2$;
$C_1-C_4$ alkyl substituted with 0–3 $R^{9e}$;
$C_1-C_4$ alkoxy substituted with 0–3 $R^{9e}$;
$C_3-C_6$ cycloalkyl substituted with 0–3 $R^{9e}$;
aryl substituted with 0–5 $R^{9e}$; and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $R^{9e}$;

$R^{9e}$ is selected at each occurrence from the group:
$C_1-C_4$ alkyl, $C_1-C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;

$R^{11}$ and $R^{11a}$ are, at each occurrence, independently selected from the group: H;
$C_1-C_4$ alkyl substituted with 0–1 $R^{11b}$;
phenyl substituted with 0–2 $R^{11b}$; and
benzyl substituted with 0–2 $R^{11b}$;

$R^{11b}$ is OH, $C_1-C_4$ alkoxy, F, Cl, Br, I, $NH_2$, or —$NH(C_1-C_4$ alkyl);

$OR^{26}$ and $OR^{27}$ are independently selected from:
a) —OH,
d) $C_1-C_8$ alkoxy, and
when taken together, $OR^{26}$ and $OR^{27}$ form:
e) a cyclic boronic ester where said cyclic boronic ester contains from 2 to 16 carbon atoms;

$A^3$, $A^4$, and $A^5$, are independently selected from an amino acid residue wherein said amino acid residue, at each occurence, is independently selected from the group:
Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, Homolys, Phe(4-fluoro), Tpa, Asp(OMe), Glu(OMe), Hyp(OMe), Asp (O'Bu), Glu(O'Bu), Hyp(O'Bu), Thr(O'Bu), Asp(OBzl), Glu (OBzl), Hyp(OBzl), Pro(OBzl), Thr(OBzl), cyclohexylglycine, cyclohexylalanine, cyclopropylglycine, t-butylglycine, phenylglycine, and 3,3-diphenylalanine.

[4] In another alternative embodiment, the present invention provides a compound of Formula (I) or a pharmaceutically acceptable salt or prodrug thereof, wherein:
$A^1$ is —$CH_2$—;
$A^2$ is —$C(=O)R^{9b}$, —$S(=O)R^{9b}$, —$S(=O)_2R^{9b}$, —$CONHR^{9b}$, —$S(=O)_2NHR^{9b}$, —$C(=O)OR^{9b}$;
—$A^3$—$R^{9a}$;
—$A^3$—$A^4$—$R^{9a}$; or
—$A^3$—$A^4$—$A^5$—$R^{9a}$;
W is —$B(OR^{26})(OR^{27})$;
$R^1$ is selected from the group: H;
$C_1-C_4$ alkyl substituted with 0–2 $R^{1a}$;
$C_2-C_4$ alkenyl substituted with 0–2 $R^{1a}$;
$C_2-C_4$ alkynyl substituted with 0–2 $R^{1a}$;
$R^{1a}$ is selected at each occurrence from the group:
Cl, F, Br, $CF_3$, or CHF2;
$R^2$ is H or methyl;
$R^3$ is selected from the group: $R^4$,
—$(CH_2)_p$—NH—$R^4$,
—$(CH_2)_p$—NHC(=O)—$R^4$,
—$(CH_2)_p$—C(=O)NH $R^4$,
—$(CH_2)_p$—C(=)O—$R^4$,
—$(CH_2)_p$—NHC(=O)NH—$R^4$,
—$(CH_2)_p$—NHC(=O)NHC(=O)—$R^4$,
—$(CH_2)_p$—C(=O)—$R^4$,
—$(CH_2)_p$—O—$R^4$, and —$(CH_2)_p$—S—$R^4$;

p is 0 or 1;

$R^4$ is selected from the group:

$C_1$–$C_4$ alkyl substituted with 0–3 $R^{4a}$;

$C_2$–$C_4$ alkenyl substituted with 0–3 $R^{4a}$;

$C_2$–$C_4$ alkynyl substituted with 0–3 $R^{4a}$;

$C_3$–$C_4$ cycloalkyl substituted with 0–2 $R^{4b}$;

phenyl substituted with 0–3 $R^{4b}$;

naphthyl substituted with 0–3 $R^{4b}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4b}$;

$R^{4a}$ is, at each occurrence, independently selected from: H, F, Cl, Br, —$NO_2$, —CN, —$CF_3$, —$OCF_3$, OH, —$CO_2H$, —$CO_2R^{11}$, C(=NH)$NH_2$, —NHC(=O)$R^{11}$, $NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —$NR^{11}C(=O)NR^{11}R^{11a}$, —$NR^{11}SO_2R^{11a}$;

$C_1$–$C_4$ alkyl substituted with 0–2 $R^{4b}$;

phenyl substituted with 0–3 $R^{4c}$;

naphthyl substituted with 0–3 $R^{4c}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4c}$;

$R^{4b}$ is, at each occurrence, independently selected from: H, F, Cl, Br, —$NO_2$, —CN, —$CF_3$, —$OCF_3$, OH, —$CO_2H$, —C(=NH)$NH_2$, —$CO_2R^{11}$, —C(=O)$NR^{11}R^{11a}$, —NHC(=O)$R^{11}$, $NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —$NR^{11}C(=O)NR^{11}R^{11a}$, —$NR^{11}SO_2R^{11a}$;

$C_1$–$C_4$ alkyl substituted with 0–1 $R^{4c}$;

phenyl substituted with 0–3 $R^{4d}$;

naphthyl substituted with 0–3 $R^{4d}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4c}$ is, at each occurrence, independently selected from: H, F, Cl, Br, —$NO_2$, —CN, —$CF_3$, —$OCF_3$, OH, —$CO_2H$, —C(=NH)$NH_2$, —$CO_2R^{11}$, —C(=O)$NR^{11}R^{11a}$, —NHC(=O)$R^{11}$, $NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ haloalkyl, $C_1$–$C_4$ haloalkoxy and $C_1$–$C_4$ alkyl;

$R^{4d}$ is, at each occurrence, independently selected from: H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, $NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^{9a}$ is selected from the group: H, —S(=O)$R^{9b}$, —S(=O)$_2R^{9b}$, —S(=O)$_2NHR^{9b}$, —C(=O)$R^{9b}$, —C(=O)O$R^{9b}$, —C(=O)NH$R^{9b}$, —C(=O)NHC(=O)$R^{9b}$;

$C_1$–$C_4$ alkyl substituted with 0–2 $R^{9c}$;

$C_3$–$C_{12}$ carbocycle substituted with 0–3 $R^{9d}$;

phenyl substituted with 0–3 $R^{9d}$;

naphthyl substituted with 0–3 $R^{9d}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{9d}$;

$R^{9b}$ is selected from the group: H;

$C_1$–$C_4$ alkyl substituted with 0–1 $R^{9c}$;

$C_2$–$C_4$ alkenyl substituted with 0–1 $R^{9c}$;

$C_2$–$C_4$ alkynyl substituted with 0–1 $R^{9c}$;

$C_3$–$C_{12}$ carbocycle substituted with 0–3 $R^{9d}$;

phenyl substituted with 0–3 $R^{9d}$;

naphthyl substituted with 0–3 $R^{9d}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{9d}$;

$R^{9c}$ is selected from the group: $CF_3$, $OCF_3$, Cl, F, Br, OH, C(O)$OR^{11}$, $NH_2$, NH($CH_3$), N($CH_3$)$_2$, —CN, $NO_2$;

$C_1$–$C_4$ alkyl substituted with 0–2 $R^{9d}$;

$C_2$–$C_4$ alkenyl substituted with 0–2 $R^{9d}$;

$C_2$–$C_4$ alkynyl substituted with 0–2 $R^{9d}$;

$C_3$–$C_6$ cycloalkyl substituted with 0–2 $R^{9e}$; $C_3$–$C_{12}$ carbocycle substituted with 0–3 $R^{9e}$;

phenyl substituted with 0–3 $R^{9e}$;

naphthyl substituted with 0–3 $R^{9e}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{9e}$;

$R^{9d}$ is selected at each occurrence from the group: $CF_3$, $OCF_3$, Cl, F, Br, OH, $C(O)OR^{11}$, $NH_2$, $NH(CH_3)$, $N(CH_3)_2$, —CN, $NO_2$, $C_1$–$C_4$ alkyl, $C_1$–$C_4$ alkoxy, and phenyl;

$R^{9e}$ is selected at each occurrence from the group:

$C_1$–$C_4$ alkyl, $C_1$–$C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;

$R^{11}$ and $R^{11a}$ are, at each occurrence, independently selected from the group: H, methyl, ethyl, propyl, butyl, phenyl and benzyl;

$OR^{26}$ and $OR^{27}$ are independently selected from:

a) —OH, d) $C_1$–$C_8$ alkoxy, and when taken together, $OR^{26}$ and $OR^{27}$ form:

e) a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanedio, 5,6-decanediol, 1,2-dicyclohexylethanediol, diethanolamine, and 1,2-diphenyl-1,2-ethanediol;

$A^3$ is Val, Glu, Ile, Thr, cyclohexylglycine, or cyclohexylalanine;

$A^4$ is Val, Ile, Leu, cyclohexylglycine, cyclopropylglycine, t-butylglycine, phenylglycine, or 3,3-diphenylalanine; and $A^5$ is (D or L stereochemistry) Asp, Clu, Val, Ile, t-butylglycine, and Gla.

[5] In another alternative embodiment, the present invention provides a compound of Formula (I) or a pharmaceutically acceptable salt or prodrug thereof, wherein:

$A^1$ is —$CH_2$—;

$A^2$ is H, —C(=O)$R^{9b}$, —CONHR$^{9b}$, —C(=O)OR$^{9b}$;

—$A^3$—$R^{9a}$; or

—$A^3$—$A^4$—$R^{9a}$;

W is pinanediol boronic ester;

$R^1$ is H, ethyl, allyl, or 2,2-difluoro-ethyl;

$R^2$ is H;

$R^3$ is selected from the group: $R^4$,

—(CH$_2$)$_p$—NH—$R^4$,

—(CH$_2$)$_p$—NHC(=O)—$R^4$,

—(CH$_2$)$_p$—C(=O)NH—$R^4$,

—(CH$_2$)$_p$—C(=O)O—$R^4$,

—(CH$_2$)$_p$—NHC(=O)NH—$R^4$,

—(CH$_2$)$_p$—NHC(=O)NHC(=O) —$R^4$,

—(CH$_2$)$_p$—C(=O)—$R^4$,

—(CH$_2$)$_p$-o-$R^4$, and

—(CH$_2$)$_p$—S—$R^4$;

p is 0 or 1;

$R^4$ is selected from the group: H, methyl, isopropyl, t-butyl, phenyl, benzyl, phenethyl, Ph-propyl, 3-Ph-2-propenyl, phenyl, 2-benzoic acid, 5-isophthalate dimethyl ester, triphenylmethyl, 1-(1-naphthyl)ethyl, 2-methylphenyl, 4-methylphenyl, 4-ethylphenyl, 2-isopropylphenyl, 4-isopropylphenyl, 4-tert-butylphenyl, 2-methoxyphenyl, 3-methoxyphenyl, 4-methoxyphenyl, 2-ethoxyphenyl, 4-ethoxyphenyl, 2-F-phenyl, 3-F-phenyl, 4-F-phenyl, 2-Cl-phenyl, 4-Cl-phenyl, 2-CF$_3$-phenyl, 3-CF$_3$-phenyl, 4-CF$_3$-phenyl, 4-(trifluoromethoxy)phenyl, 4-(hydroxymethyl)phenyl, 3-cyanophenyl, 3-(acetyl) phenyl, 2-phenoxyphenyl, 3-phenoxyphenyl, 4-(acetyl) phenyl, 2-(methoxycarbonyl)-phenyl, 3-(methoxycarbonyl)-phenyl, 4-(methoxycarbonyl)-phenyl, 2-(ethoxycarbonyl)-phenyl, 3-(ethoxycarbonyl)-phenyl, 4-(ethoxycarbonyl)phenyl, 2-(butoxycarbonyl)phenyl, 2-(tert-butoxycarbonyl) phenyl, 4-(dimethylamino)phenyl, 2-(methylthio) phenyl, 3-(methylthio)phenyl, 4-(methylthio)phenyl, 2-(methylsulfonyl)phenyl, 3-CF$_3$S-phenyl, 2-nitrophenyl, 4-nitrophenyl, 2-aminophenyl, 4-(benzyloxy)phenyl, 2-biphenyl, 4-biphenyl, 2,6-diisopropylphenyl, 2,4-diF-phenyl, 2,5-diF-phenyl, 2,6-diF-phenyl, 3,4-dichlorophenyl, 2,4-dimethoxyphenyl, 2,5-dimethoxyphenyl, 5-Cl-2-methoxyphenyl, 4-F-2-nitrophenyl, 3,4,5,-trimethoxyphenyl, 5-Cl-2,4-dimethoxyphenyl, 5-F-2, 4-dimethoxyphenyl, Trans-2-phenylcyclopropyl, 1-naphthyl, 2-naphthyl, 2-pyridinyl, 3-pyridinyl, 2-quinolinyl, 5-quinolinyl, 1-isoquinolinyl, 2-phenyl-4-quinolinyl, 2-phenyl-4-quinolinyl-methyl, 2-methyl-6-quinolinyl, 2-anilino-2-oxoethyl and 2-3-methylbutyric acid methyl ester;

$R^{9a}$ is selected from the group: H, —S(=O)$R^{9b}$, —S(=O)$_2$ $R^{9b}$, —S(=O)$_2$NHR$^{9b}$, —C(=O)$R^{9b}$, —C(=O)OR$^{9b}$, —C(=O)NHR$^{9b}$, —C(=O)NHC(=O)$R^{9b}$;

$C_1$–$C_4$ alkyl substituted with 0–2 $R^{9c}$;

$C_3$–$C_{12}$ carbocycle substituted with 0–2 $R^{9d}$;

phenyl substituted with 0–2 $R^{9d}$; naphthyl substituted with 0–2 $R^{9d}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–2 $R^{9d}$;

$R^{9b}$ is selected from the group: H;

$C_1$–$C_4$ alkyl substituted with 0–1 $R^{9c}$;

$C_3$–$C_{12}$ carbocycle substituted with 0–2 $R^{9d}$;

phenyl substituted with 0–2 $R^{9d}$;

naphthyl substituted with 0–2 $R^{9d}$; and

5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–2 $R^{9d}$;

$R^{9c}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$;

$C_1$–$C_4$ alkyl substituted with 0–1 $R^{9d}$;

$C_2$–$C_4$ alkenyl substituted with 0–1 $R^{9d}$;

$C_2$–$C_4$ alkynyl substituted with 0–1 $R^{9d}$; and $R^{9d}$ is selected at each occurrence from the group:
$CF_3$, $OCF_3$, Cl, F, Br, OH, $C(O)OR^{11}$, $NH_2$, $NH(CH_3)$, $N(CH_3)_2$, —CN, $NO_2$, $C_1$–$C_4$ alkyl, $C_1$–$C_4$ alkoxy, and phenyl;

$R^{11}$ is selected from the group: H, methyl, ethyl, propyl, butyl, phenyl and benzyl;

$A^3$ is Val, Glu, Ile, Thr, cyclohexylglycine, or cyclohexylalanine; and $A^4$ is Val, Ile, Leu, cyclohexylglycine, cyclopropylglycine, t-butylglycine, phenylglycine, or 3,3-diphenylalanine.

[6] In another alternative embodiment, the present invention provides a compound of Formula (I) or a pharmaceutically acceptable salt or prodrug thereof, wherein:

$A^1$ is —$CH_2$—;

$A^2$ is —$C(=O)OR^{9b}$ or —$A^3$—$R^{9a}$;

W is pinanediol boronic ester;

$R^1$ is H, ethyl or allyl;

$R^2$ is H;

$R^3$ is $R^4$;

$R^4$ is selected from the group: Ph-propyl, 3-Ph-2-propenyl, 2-phenyl-4-quinolinyl, 2-phenyl-4-quinolinyl-methyl, 2-methyl-6-quinolinyl, and 2-anilino-2-oxoethyl;

$R^{9a}$ is selected from the group: —$S(=O)_2R^{9b}$, —$C(=O)R^{9b}$, —$C(=O)OR^{9b}$, and —$C(=O)NHR^{9b}$;

$R^{9b}$ is selected from the group: t-butyl, fluorenylmethyl, fluorenyl, benzyl;

phenyl substituted with 0–2 $R^{9d}$;

naphthyl substituted with 0–2 $R^{9d}$; and pyridinyl substituted with 0–2 $R^{9d}$;

$R^{9d}$ is selected at each occurrence from the group:
$CF_3$, $OCF_3$, Cl, F, Br, OH, $C(O)OR^{11}$, $NH_2$, $NH(CH_3)$, $N(CH_3)_2$, —CN, $NO_2$, $C_1$–$C_4$ alkyl, $C_1$–$C_4$ alkoxy, and phenyl; and $A^3$ is Val.

It is understood that any and all embodiments of the present invention may be taken in conjunction with any other embodiment to descibe additional even more preferred embodiments of the present invention.

[7] In another alternative embodiment, the present invention provides a compound, or a stereoisomer or a pharmaceutically acceptable salt form or prodrug thereof, selected from:

(4S)-N-{[[(1R)-1-[(3αS,4S,6S,7α(R)-hexahydro-3α,5,5-trimethyl-4,6-methano-1,3,2-benzodioxaborol-2-yl]propyl}-3-{(2S)-3-methyl-2-[(phenylacetyl)-amino]-butanoyl)-2-oxo-1-(3-phenylpropyl)-4-imidazolidinecarboxamide;

tert-butyl (1S)-N-{[[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl)imidazolidinyl]carbonyl}-2-methylpropylcarbamate;

(4S)-N-{[[(1R)-1-[(3αS,4S,6S,7αR)-hexahydro-3,α5,5-trimethyl-4,6-methano-1,3,2-benzodioxaborol-2-yl]propyl}-3-{(2S)-2-[(anilinocarbonyl)amino]-3-methylbutanoyl}-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[(9H-fluoren-1-ylcarbonyl)aminol]-3-methylbutanoyl)-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-((2S)-2-{[(4-methoxyphenyl)acetyl]amino}-3-methylbutanoyl)-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]-3-butenyl}-3-{(2S)-2-[(9H-fluoren-1-ylcarbonyl)amino]-3-methylbutanoyl)-2-oxo-1-(3-phenylpropyl)-4-imidazolidinecarboxamide;

9H-fluoren-9-ylmethyl (1S)-N-{[[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl)imidazolidinyl]carbonyl}-2-methylpropylcarbamate;

(4S)-N-({[(1R)-1-[(3αS,4S,6S,7αR)-hexahydro-3α,5,5-trimethyl-4,6-methano-1,3,2-benzodioxaborol-2-yl]propyl}-3-((2S)-3-methyl-2-{[3-(trifluoromethyl)benzyl]amino}butanoyl)-2-oxo-1-(3-phenylpropyl)-4-imidazolidinecarboxamide;

(4S) —N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[([1,1'-biphenyl]-4-ylmethyl)amino]-3-methylbutanoyl}-2-oxo-1-(3-phenylpropyl)-4-imidazolidinecarboxamide; 9H-fluoren-9-ylmethyl (1S)-1-({(5S)-5-[({(1R)-1-[(3αS,4S,6S,7αR)-hexahydro-3α,5,5-trimethyl-4,6-methano 1,3,2-benzodioxaborol-2-yl]propyl}amino)carbonyl]-2-oxo-3-[(2-phenyl-4-quinolinyl)methyl]imidazolidinyl)carbonyl)-2-methylpropylcarbamate;

N-((1S)-1-{[(5S)-5-{[[(1R)-1-[(3αS,4S,6S,7αR)-hexahydro-3α,5,5-trimethyl-4,6-methano-1,3,2-benzodioxaborol-2-yl]propyl)-amino)carbonyl]-2-oxo-3-(3-phenylpropyl)imidazolidinyl]carbonyl}-2-methylpropyl)-2-chloronicotinamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[(4-butylbenzoyl)amino]-3-methylbutanoyl}-2-oxo-1-(3-phenylpropyl)-4-imidazolidinecarboxamide;

isobutyl (1S)-1-{[(5S)-5-([[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl)imidazolidinyl]carbonyl}-2-methylpropylcarbamate;

(4S)-N-{([[(1R)-1-[(3αS,4S,6S,7αR)-hexahydro-3α,5,5-trimethyl-4,6-methano-1,3,2-benzodioxaborol-2-yl]propyl}-3-((2S)-2-([(benzoylamino)carbonyl]amino}-3-methylbutanoyl)-2-oxo-1-(3-phenylpropyl)-4-imidazolidinecarboxamide;

(4S)-N-{[(1R)-1-[(3αS,4S,6S,7αR)-hexahydro-3α,5,5-trimethyl-4,6-methano-1,3,2-benzodioxaborol-2-yl]propyl}-3-[(2S)-3-methyl-2-(1-naphthoylamino)butanoyl]-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl)-3-[(2S)-2-(acetylamino)-3-methylbutanoyl]-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-[(2S)-2-(benzoylamino)-3-methylbutanoyl]-2-oxo-1-(3-phenylpropyl)-4-imidazolidinecarboxamide;

benzyl (5S)-5-[({(1R)-1-[(3αS,4S,6S,7αR)-hexahydro-3α,5,5-trimethyl-4,6-methano-1,3,2-benzodioxaborol-2-yl]-3-butenyl}amino)carbonyl]-2-oxo-3-[(2E)-3-phenyl-2-propenyl]-1-imidazolidinecarboxylate; and benzyl (5S)-5-[({(1R)-1-[(3αS,4S,6S,7αR)-hexahydro-3α,5,5-trimethyl-4,6-methano-1,3,2-benzodioxaborol-2-yl]-3-butenyl}amino)carbonyl]-3-(2-anilino-2-oxoethyl)-2-oxo-1-imidazolidinecarboxylate.

This invention also provides compositions comprising one or more of the foregoing compounds and methods of using such compositions in the treatment of hepatitis C virus, such as inhibition of hepatitis C virus protease, in mammals or as reagents used as inhibitors of hepatitis C virus protease in the processing of blood to plasma for diagnostic and other commercial purposes.

In another embodiment, the present invention provides a pharmaceutical composition comprising a compound of Formula (I) and a pharmaceutically acceptable carrier.

In another embodiment, the present invention provides a method of treating a viral infection which comprises administering to a host in need of such treatment a therapeutically effective amount of compounds of Formula (I) or pharmaceutically acceptable salt forms or prodrug thereof.

In another embodiment, the present invention provides A method of treating HCV which comprises administering to a host in need of such treatment a therapeutically effective amount of compounds of Formula (I) or pharmaceutically acceptable salt forms or prodrug thereof.

DEFINITIONS

As used throughout the specification, the following abbreviations for amino acid residues or amino acids apply:

Abu is L-aminobutyric acid;
Ala is L-alanine;
Alg is L-2-amino-4-pentenoic acid;
Ape is L-2-aminopentanoic acid;
Arg is L-arginine;
Asn is L-asparagine;
Asp is L-aspartic acid;
Aze is azedine-2-carboxlic acid;
Cha is L-2-amino-3-cyclohexylpropionic acid;
Cpa is L-2-amino-3-cyclopropylpropionic acid
Cpg is L-2-amino-2-cyclopropylacetic acid;
Cys is L-cysteine;
Dfb is L-4,4'-difluoro-1-amino-butyric acid;
Dpa is L-2-amino-3,3-diphenylpropionic acid;
Gla is gamma-carboxyglutamic acid;
Gln is L-glutamine;
Glu is L-glutamic acid;
Gly is glycine;
H is is L-histidine;
HomoLys is L-homolysine;
Hyp is L-4-hydroxyproline;
Ile is L-isoleucine;
Irg is isothiouronium analog of L-Arg;
Leu is L-leucine;

Lys is L-lysine;
Met is L-methionine;
Orn is L-ornithine;
Phe is L-phenylalanine;
Phe(4-fluoro) is para-fluorophenylalanine;
Pro is L-proline;
Sar is L-sarcosine;
Ser is L-serine;
Thr is L-threonine;
Tpa is L-2-amino-5,5,5-trifluoropentanoic acid;
Trp is L-tryptophan;
Tyr is L-tyrosine; and
Val is L-valine.

The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic ester. For example, if $R^1$ is isopropyl and $Y^1$ and $Y^2$ are OH, the C-terminal residue is abbreviated "boroVal-OH" where "—OH" indicates the boronic acid is in the form of the free acid. The pinanediol boronic ester and the pinacol boronic ester are abbreviated "—$C_{10}H_{16}$" and "—$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Analogs containing sidechain substituents are described by indicating the substituent in parenthesis following the name of the parent residue. For example the analog of borophenylalanine containing a meta cyano group is -boroPhe(mCN)—.

The following abbreviations may also be used herein and are defined as follows. The abbreviation "DIBAL" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate. Other abbreviations are: "BSA", benzene sulfonic acid; "THF", tetrahydrofuran; "DMF", dimethylformamide; "EDCI", 1-dimethylaminopropyl-3-ethylcarbodiimide hydrochloride; "HOAt", 1-hydroxy-7-azabenzotriazole; "DIEA", N,N-diisopropylethylamine; "Boc-", t-butoxycarbonyl-; "Ac-", acetyl; "pNA", p-nitro-aniline; "DMAP", 4-N,N-dimethylaminopyridine; "Tris", Tris (hydroxymethyl)aminomethane; "PyAOP", 7-azabenzotriazol-1-yloxytris(pyrrolidino)phosphonium hexafluorophosphate; "MS", mass spectrometry; "FAB/MS", fast atom bombardment mass spectrometry. LRMS ($NH_3$-CI)and HRMS($NH_3$-CI)are low and high resolution mass spectrometry, respectively, using $NH_3$ as an ion source.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then two hydrogens on the atom are replaced.

When any variable (e.g., $R^{4a}$ or $R^{11}$) occurs more than one time in any constituent or formula for a compound, its definition at each occurrence is independent of its definition at every other occurrence. Thus, for example, if a group is shown to be substituted with 0–3 $R^{4a}$, then said group may optionally be substituted with up to three $R^{4a}$ groups and $R^{4a}$ at each occurrence is selected independently from the definition of $R^{4a}$. Also, combinations of substituents and/or variables are permissible only if such combinations result in stable compounds. By stable compound it is meant herein a compound that is sufficiently robust to survive isolation to a useful degree of purity from a reaction mixture.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

"Amino acid residue" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, H is, Hyp, Ile, Leu, Lys, Met, Orn, Phe, Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,β-disubstituted amino acids. Included in the scope of the present invention are N-alkyl, aryl, and alkylaryl analogs of both in chain and N-terminal amino acid residues. Similarly, alkyl, aryl, and alkylaryl maybe substituted for the alpha hydrogen. Illustrated below are examples of N-alkyl and alpha alkyl amino acid residues, respectively.

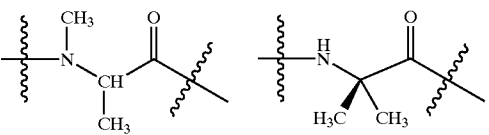

Modified amino acids which can be used to practice the invention include, but are not limited to, D-amino acids, hydroxylysine, 4-hydroxyproline, 3-hydroxyproline, an N-CBZ-protected amino acid, 2,4-diaminobutyric acid, homoarginine, norleucine, N-methylaminobutyric acid, 3,3-diphenylalanine, naphthylalanine, phenylglycine, β-phenylproline, tert-leucine, cyclohexylalanine, 4-aminocyclohexylalanine, N-methyl-norleucine, 3,4-dehydroproline, t-butylglycine, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, 2-benzyl-5-aminopentanoic acid.

A list of unnatural amino acids that fall within the scope of this invention is disclosed in a PCT application PCT/US00/18655. The disclosure of which is hereby incorporated by reference. "Amino acid residue" also refers to various amino acids where sidechain functional groups are modified with appropriate protecting groups known to those skilled in the art. "The Peptides", Vol 3, 3–88 (1981) discloses numerous suitable protecting groups and is incorporated herein by reference for that purpose. Examples of amino acids where sidechain functional groups are modified with appropriate protecting groups include, but are not limited to, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), and Thr(OBzl); wherein OMe is methoxy, O'Bu is tert-butoxy, and OBzl is benzyloxy.

A preferred list of "amino acid residue" in the present invention includes, but is not limited to, Ala, Arg, Asn, Asp, Aze, Cys, Gln, Glu, Gly, H is, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, Homol.ys, Phe(4-fluoro), Tpa, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine.

A preferred scope of substituent $A^3$ is Val, Clu, Ile, Thr, cyclohexylglycine, and cyclohexylalanine.

A preferred scope of substituent $A^4$ is Val, Ile, Leu, cyclohexylglycine, cyclopropylglycine, t-butylglycine, phenylglycine, and 3,3-diphenylalanine.

A preferred scope of substituent $A^5$ is (D or L stereochemistry) Asp, Glu, Val, Ile, t-butylglycine, and Gla.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon—carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon—carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$CVFw$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

As used herein, "carbocycle", "carbocyclic ring", "carbocyclic group", or "carbocyclic ring system" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle", "heterocyclic group", "heterocyclic ring" "heterocyclic ring system" or "Het" is intended to mean a stable 5- to 7-membered monocyclic or bicyclic or 7- to 14-membered bicyclic heterocyclic ring which is saturated, partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, benzo[1,3]dioxol-yl, 2,3-dihydro-benzo[1,4]dioxin-yl, carbazolyl, 4αH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyrimidopyrimidin-yl, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5–10 membered heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

The term "Het-(lower alkyl)-" as used herein, means a heterocyclic ring as defined above linked through a chain or branched $C_1$–$C_6$ alkyl group.

As used herein, the term "aryl", or aromatic residue, is intended to mean an aromatic moiety containing the specified number of carbon atoms, such as phenyl and naphthyl.

"$NH_2$-blocking group" as used herein, refers to various acyl, thioacyl, alkyl, sulfonyl, phosphoryl, and phosphinyl groups comprised of 1 to 20 carbon atoms. Substitutes on these groups maybe either alkyl, aryl, alkylaryl which may contain the heteroatoms, O, S, and N as a substituent or in-chain component. A number of $NH_2$-blocking groups are recognized by those skilled in the art of organic synthesis. By definition, an $NH_2$-blocking group may be removable or may remain permanently bound to the $NH_2$. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meinhoffer, eds., The Peptides, Vol 3; 3–88 (1981), Academic Press, New York, and Greene and Wuts Protective Groups in Organic Synthesis, 315–405 (1991), J. Wiley and Sons, Inc., New York disclose numerous suitable amine protecting groups and they are incorporated herein by reference for that purpose. Amine protecting groups may include, but are not limited to the following: 2,7-di-t-butyl-[9-(10,10-dioxo-10,10,10,10-tetrahydrothioxanthyl)]methylo xycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzylsoxazolylmethyloxycarbonyl; p-(dihydroxyboryl) benzyloxycarbonyl; m-nitrophenyloxycarbonyl; o-nitrobenzyloxycarbonyl; 3,5-dimetboxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, "cyclic boronic ester" is intended to mean a stable cyclic boronic moiety of general formula —B(OR)(OR) wherein the two R substituents taken together contain from 2 to 20 carbon atoms, and optionally, 1, 2, or 3 heteroatoms which can be N, S, or O. Cyclic boronic esters are well known in the art. Examples of cyclic boronic ester include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 2-diisopropylethanediol boronic ester, 5,6-decanediol boronic ester, 1,2-dicyclohexylethanediol boronic ester, diethanolamine boronic ester, and 1,2-diphenyl-1,2-ethanediol boronic ester.

As used herein, "cyclic boronic amide" is intended to mean a stable cyclic boronic amide moiety of general formula —B(NR)(NR) wherein the two R substituents taken together contain from 2 to 20 carbon atoms, and optionally, 1, 2, or 3 heteroatoms which can be N, S, or O. Examples of cyclic boronic amide include, but are not limited to, 1,3-diaminopropane boronic amide and ethylenediamine boronic amide.

As used herein, "cyclic boronic amide-ester" is intended to mean a stable cyclic boronic amide-ester moiety of general formula —B(OR)(NR) wherein the two R substituents taken together contain from 2 to 20 carbon atoms, and optionally, 1, 2, or 3 heteroatoms which can be N, S, or O. Examples of cyclic boronic amide include, but are not limited to, 3-amino-1-propanol boronic amide-ester and ethanolamine boronic amide-ester.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p.1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

The term "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the s disease, disorder and/or condition.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Schemes 1-6 illustrate the synthesis of inhibitors of structure 1-9. In Schemes 1-6, $A^1$, $R^3$ and $R^{9a}$ are as defined above; L is a linker; R' and $R^{1'}$ are H or simple alkyl or aryl, preferably methyl, ethyl, t-butyl, phenyl, or benzyl; $P_1$, $P_2$, $P_3$ and $P_4$ are nitrogen protecting groups, wherein such protecting groups are known to one skilled in the art.

In Scheme 1, substituted 2-imidazolidinone 4-carboxylic acids or esters, tetrahydro 2-pyrimidone 4-carboxylic acids or esters, and 1,3-diazepane 4-carboxylic acids or esters (1-2) can be prepared by cyclizations of commercially available materials or materials that may be easily prepared from commercially available ones (1-1). The cyclizations can be carried out with carbonyl diimidazole (Giudice, M. R.; Gatta, F.; Settimj, G.; *J. Heterocycl. Chem.* 1990, 27, 967), phosgene (Ellis, F.; et. al.; *J. Chem. Soc., Perkin Trans* 1, 1972, 1560), hexachloroacetone (Koenigsberger, K.; Prasad, K.; Repic, O.; Blacklock, T. J.; *Tetrahedron: Asymmetry*, 1997, 8 (14), 2347–2354), S,S-dimethyl dithiocarbonate (Leung, M.; Lai, J. -L.; Lau, K. -H.; Yu, H.; Hsiao, H. -J.; *J. Org. Chem.*, 1996, 61 (12), 4175–4179), diphenyl carbonate or its derivatives (*Eur. Pat. Appl.* 629612, 21 Dec 1994), or urea (Kulinski, T.; Tkaczynski, T.; *Pharmazie*, 1995, 50 (12), 821–822). If R' in 1-2 is a proton, acids 1-2 need to be converted to their corresponding esters 1-2 with the reaction conditions will be readily apparent to one skilled in the art and alternate methods must then be used Alkylations or acylations of 1-2 with various halides or acyl halides under basic conditions can provide 1-3 (a. Jordan, T. E.; Ginsburg, S.; *J. Am. Chem. Soc.*, 1949, 71, 2258; b. Roos, G. H. P.; Balasubramaniam, S.; Doyle, M. P.; Raab, C. E.; *Synth. Commun.*, 1996, 26 (11), 2165–2175). An alternative way to make 1-3 from 1-2 via O-silyl ethers is treatment of 1-2 with trialkylsilyl triflate in the presence of a base, such as $Et_3N$ or lutidine, and then alkylations or acylations of the O-silyl ether intermediates with various halides or acyl halides (a. Sakaitani, Masahiro; Ohfune, Yasufumi. *J. Org. Chem.* 1990, 55(3), 870–6; b. Sakaitani, Masahiro; Ohfune, Yasufumi. *J. Am. Chem. Soc.* 1990, 112(3), 1150–8). Deprotections of P3 of 1-3 can afford 1-4 (Greene, T. W. in Protective Groups in *Organic Synthesis, Ch. 7, Protection for the Amino Group*, John Wiley & Sons, 2nd Ed, 1991) As described in the preparations of 1-3, alkylations or acylations of 1-4 can provide 1-5. Hydrolyses of the ester groups of 1-5 can provide acids 1-6 (Greene, T. W. *Protective Groups in Organic Synthesis, Ch. 5, Protection for the Carbonyl Group*, John Wiley & Sons, 2nd Ed, 1991). Peptide coupling reactions of acids 1-6 with serine traps 1-10 can afford the inhibitors 1-7 (Larock, R. C. in *Comprehensive Organic Transformations: A Guide to Functional Organic Preparations*, VCH Publishers, 1989, Carboxylic Acids to Amides, 972). Deprotections of $P_1$ on the N-terminus of L provide 1-8, which can undergo peptide coupling reactions to afford the inhibitors 1-9.

Scheme 1

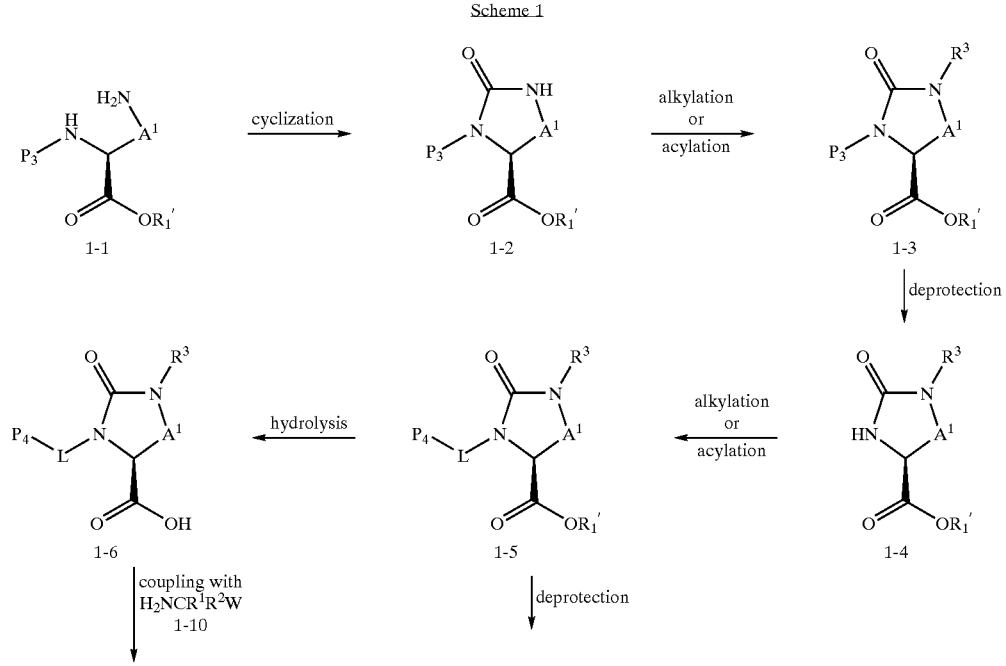

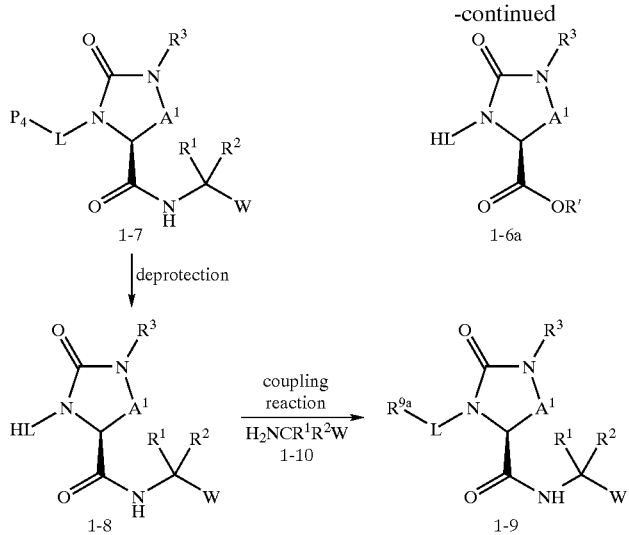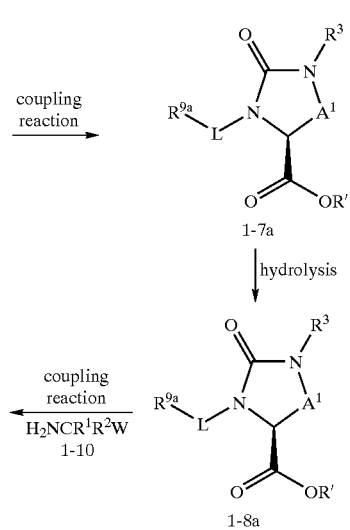

The following methods for the cyclizations, alkylations, acylations, selective protections and deprotections, hydrolyses, and coupling reactions are similar to those described above.

The inhibitors 1-9 can also be prepared from an alternative route starting from 1-5 (Scheme 1). Deprotections of the $P_4$ in 1-5 can provide 1-6a, which can undergo peptide coupling afford the inhibitors 1-7a. Hydrolyses of the ester group in 1-7a can provide acids 1-8a, which coupled with serine traps 1-10 can afford the inhibitors 1-9.

An alternative sequence for preparing 1-5 is shown in Scheme 2. Compounds 2-2 can be prepared from N-protections of 1-2 or cyclizations of commercially available 2-2a. Selective deprotections of 2-2 or 2-2a provide 2-3 or 2-3a, respectively. 2-3a can then be converted to 2-3 by cyclizations. 1-5 can be obtained from alkylations or acylations of 2-3, followed by selective deprotections of 2-4 and then alkylations or acylations of 2-5.

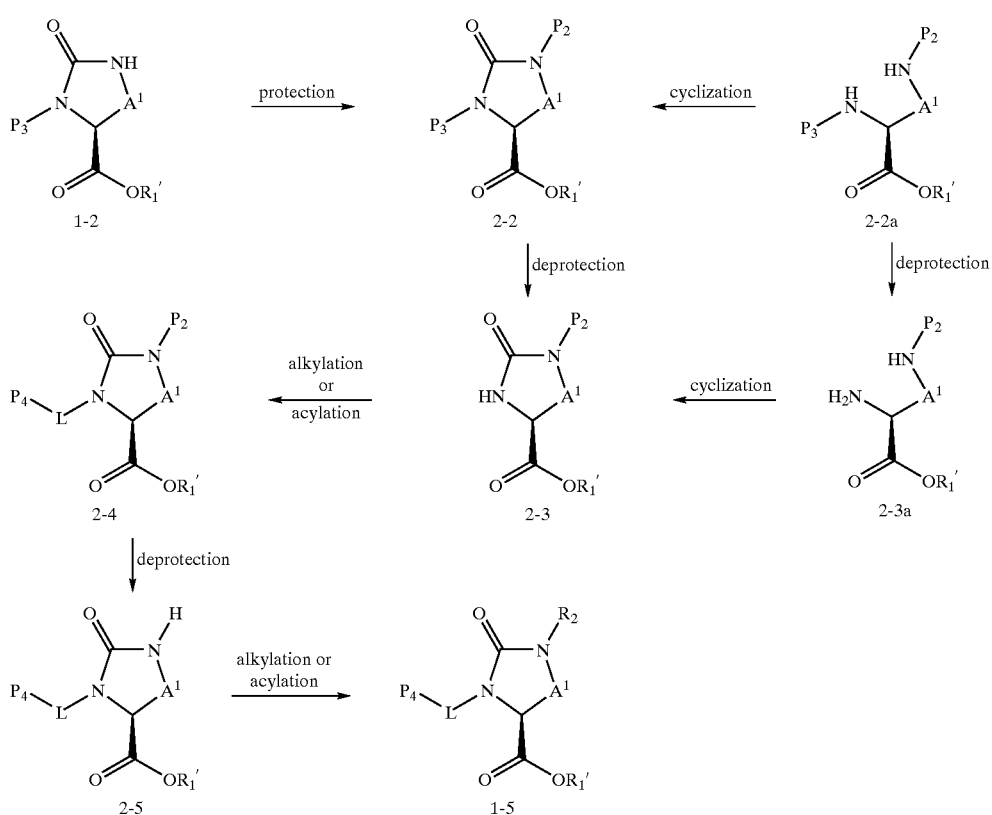

Scheme 2

The inhibitors 1-7 can also be prepared from peptide coupling reactions of the free acids 2-2 with serine traps 1-10 as shown in Scheme 3. 3-2 can be prepared from peptide coupling reactions of 2-2 with 1-10. Amides 3-2 can be converted to imides 3-3 with (Boc)$_2$O or CbzCl in the presence of base (Evans, D. A.; Carter, P. H.; Carreirra, A. B.; Prunet, J. A.; Lautens, M. *J. Am. Chem. Soc.* 1999, 121, 7540–7552). Selective deprotections of 3-3 can give either 3-4 or 3-4a, which can be further acylated or alkylated to give 3-5 or 3-5a, respectively. 3-7 can be obtained from selective deprotections of 3-5 or 3-5a, followed by acylations or alkylations of 3-6 or 3-6a, respectively. Selective deprotections of 3-7 can provide inhibitors 1-7.

Scheme 4 depicts an alternative synthesis of 2-4, 1-5, and 1-3. Selective alkylations, acylations, or reductive aminations of 1-1 or 2-3a can give 4-1 or 4-1a, respectively. Selective deprotections, followed by alkylations, acylations, or reductive aminations of 4-1 or 4-1a, can provide 4-2. Compounds 2-4, 1-5, and 1-3 can be obtained from cyclizations of 4-1a, 4-2, and 4-1, respectively.

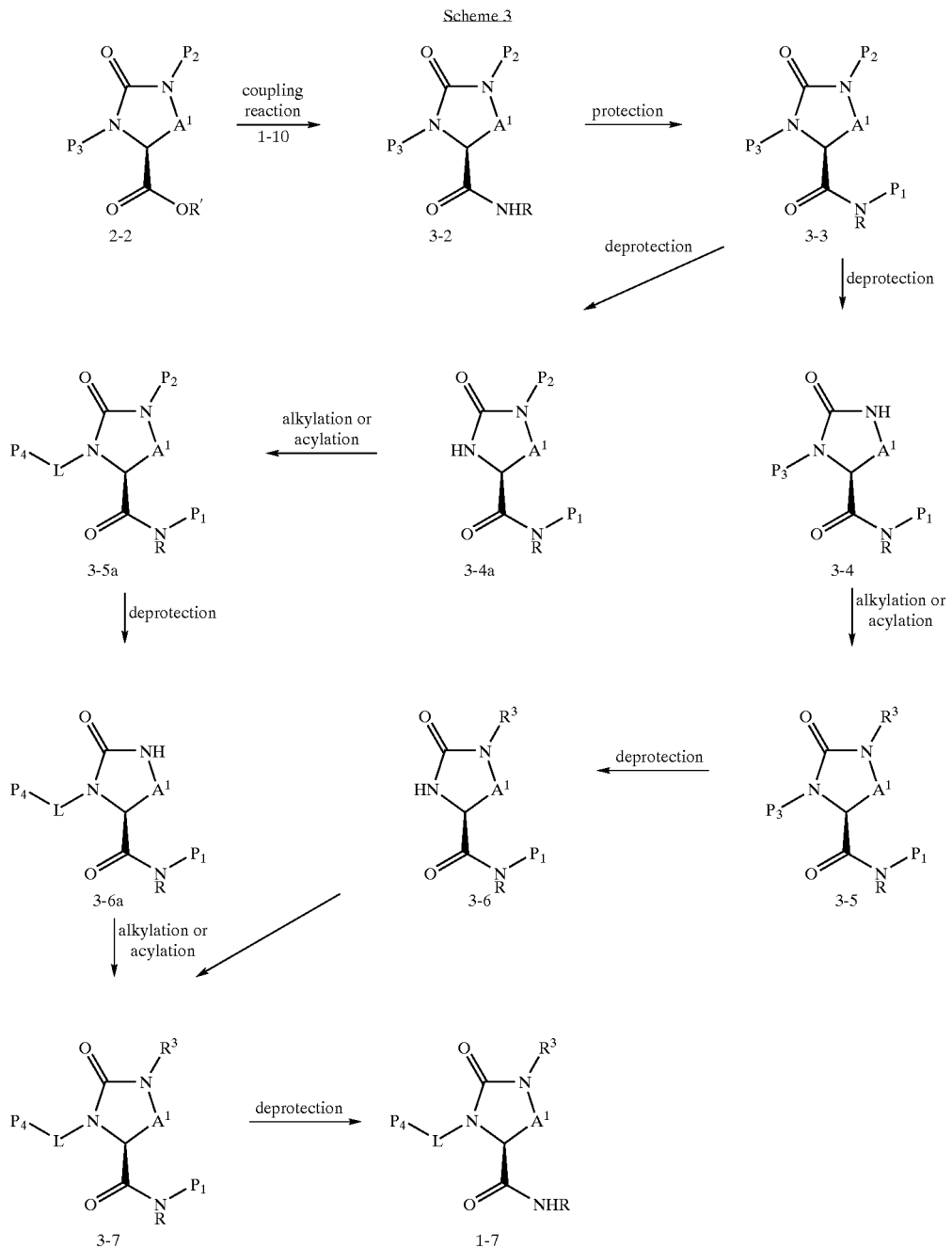

Scheme 3

Scheme 4

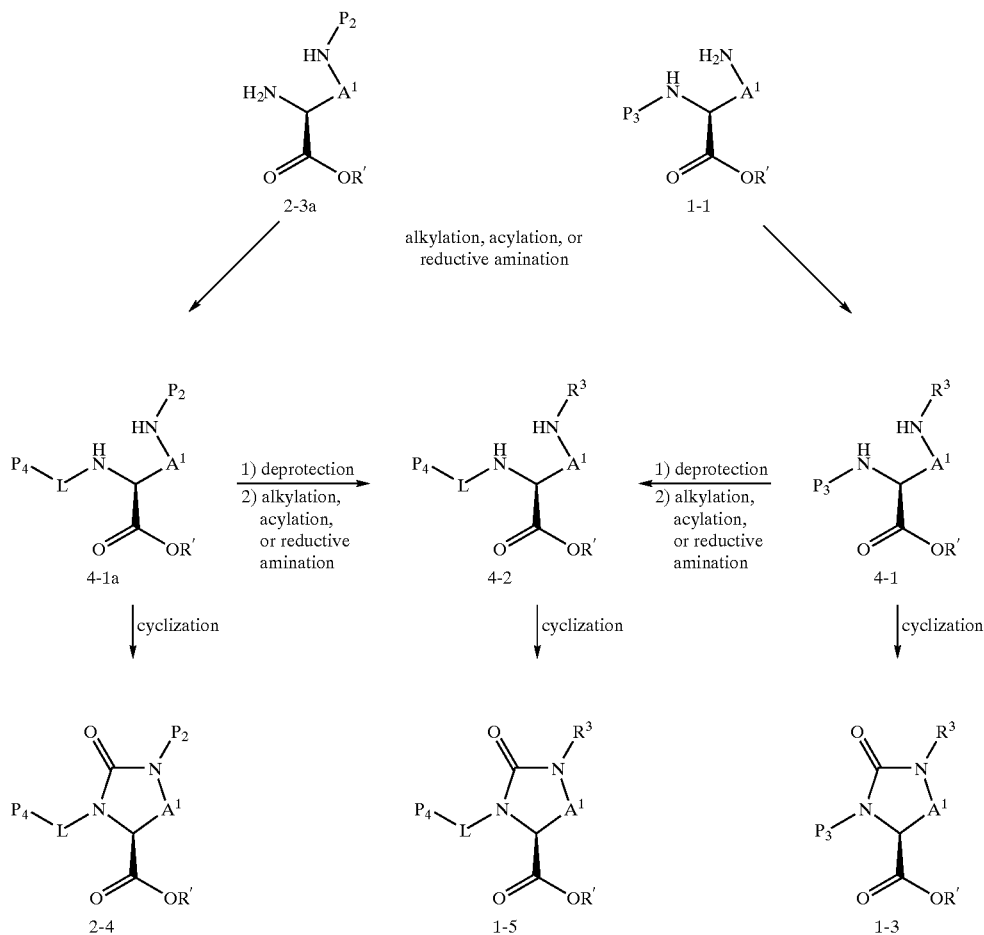

Other synthetic sequences for preparing 1-6 are summarized in Schemes 5 and 6. Shown in Scheme 5, coupling reactions of 2-2a with aniline can provide phenyl amides 5-1 (Evans, D. A.; Carter, P. H.; Carreirra, A. B.; Prunet, J. A.; Lautens, M. *J. Am. Chem. Soc.* 1999, 121, 7540–7552). Selective deprotections of 5-1 can provide 5-2 or 5-2a. 5-4 can be obtained by conversions of 5-2 to 5-3 or 5-2a to 5-3a by alkylations, acylations, or reductive aminations, followed by selective deprotections and then by additional alkylations, acylations, or reductive aminations. Cyclizations of 5-3a, 5-4, or 5-3 can provide 5-5a, 5-6, or 5-5, respectively. 5-6 can also be obtained from selective deprotections and then alkylations or acylations of 5-5a or 5-5. An alternative way to prepare amides 5-5a or 5-5 can be via coupling reactions of aniline with 2-4 or 1-3, respectively. Amides 5-6 can be converted to the imides with $Boc_2O$/$DMAP$/$CH_3CN$, and treatment the imides with $LiOH$/$H_2O_2$/$THF$/$H_2O$ can provide the acids 1-6 (a. Evans, D. A.; Carter, P. H.; Carreirra, A. B.; Prunet, J. A.; Lautens, M. *J. Am. Chem. Soc.* 1999, 121, 7540–7552; b. Gage, J. R.; Evans, D. A. *Organic Syntheses* 1989, 68, 83–91).

Scheme 5

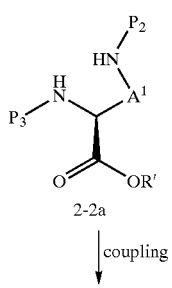

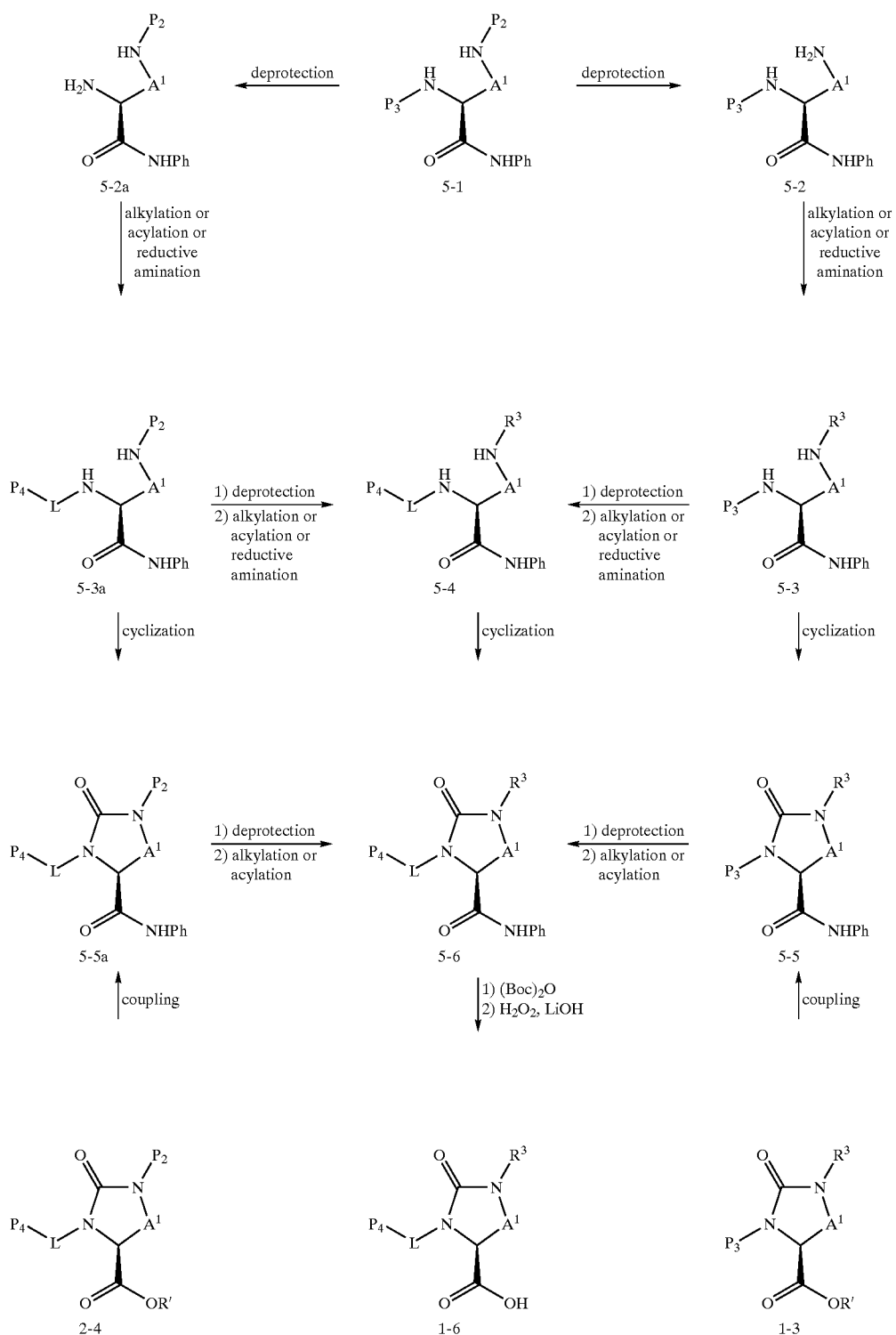

Scheme 6 is similar to Scheme 5 Coupling reactions of 2-2 with aniline, followed by treatment of the resulting amides with (Boc)$_2$O in the presence of a base, can provide 6-1. Selective deprotections of 6-1 can give 6-2 or 6-2a, which can undergo alkylations or acylations to form 6-3 or 6-3a, respectively. Selective deprotections of 6-3 and 6-3a can give 6-4 and 6-4a, respectively, which can then undergo additional alkylations or acylations to provide 6-5. Acids 1-6 can be obtained by treatment of imides 6-5 with LiOH/ H$_2$O$_2$/THF/H$_2$O.

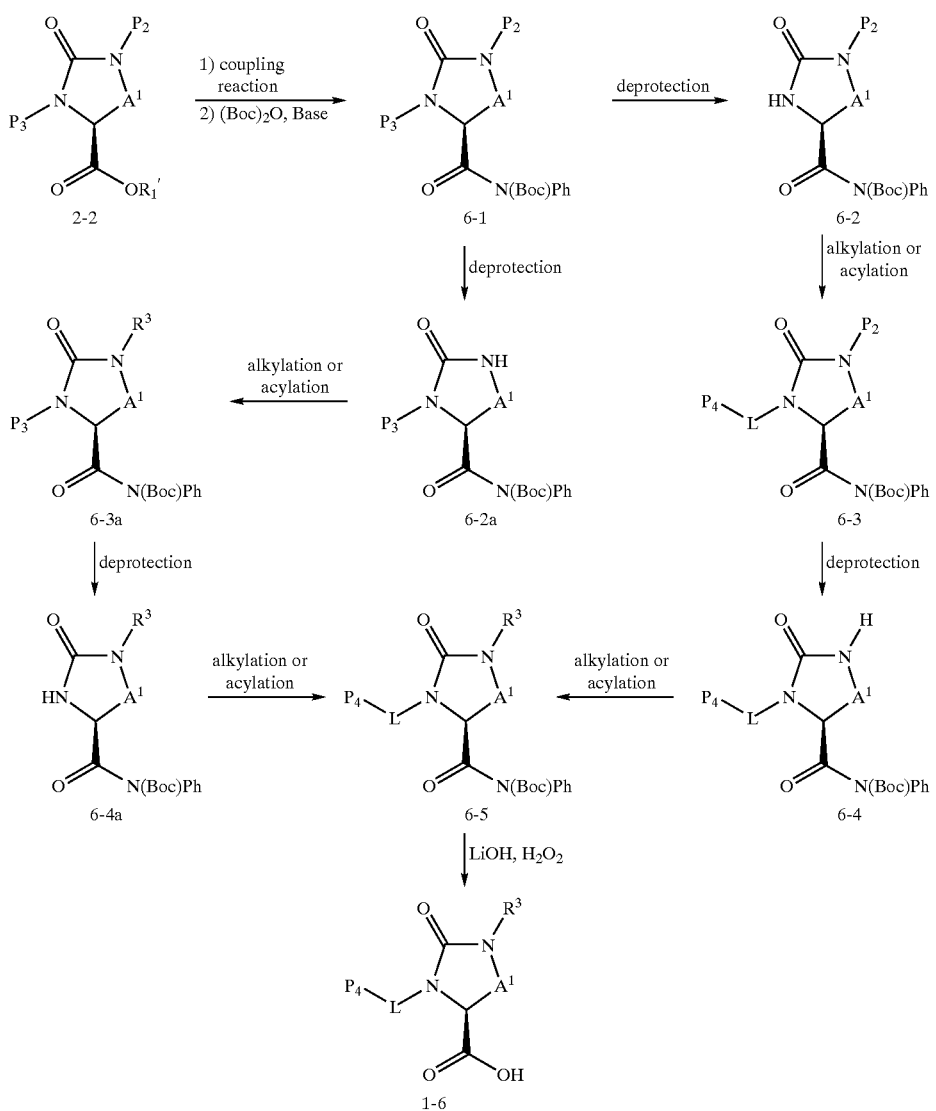

Scheme 6

Compounds of the present invention containing peptide segments in $A^2$ can be prepared from commercially available 10 materials by methods known to one skilled in the art of peptide synthesis. More preferably, see techniques disclosed in copending commonly assigned U.S. Provisional Patent Application U.S. Ser. No. 60/242,557, filed Oct. 23, 2000; herein incorporated in its entirety by reference.

Compounds of the present invention with other $R^3$ can be prepared from commercially available materials by methods known to one skilled in the art of peptide synthesis. More preferably, see techniques disclosed in the U.S. Provisional Patent Application, assigned to DuPont Pharmaceuticals Co., identified as PH-7225-P1, filed simultaneously as this application.

Synthesis of Serine Traps of Structure 1-10.

a) Synthesis of α-amino Boronic Ester

Scheme 7 outlines a route to mono-substituted amino boronic esters. In Scheme 7, a Grignard reagent can be reacted with a borate ester 7-1, which can be prepared by the reaction of pinanediol with trialkylborate (Elgendy, S.; Claeson, G.; Kakkar, V. V.; Green, D.; Patel, G.; Goodwin, C. A.; Baban, J. A.; Scully, M. F.; Deadman, J.; *Tetrahedron* 1994, 50 (12), 3803–3812), can provide boronate 7-2. Homologation of 7-2 with the anion of dichloromethane can give the α-chloro boronic ester 7-3 (Matteson, D. S.; Majumdar, D. Organometallics 1983, 2, 1529–1535). Displacement of the chloride by lithium bis(trimethylsilyl) amide can give silyl amine 7-4, which is converted to the amine hydrochloride salt 7-5 with anhydrous HCl. (Matteson, D. S.; Sadhu, K. M. Organometallics 1984, 3, 1284–1288). Notice that 7-5 is shown protected as the pinanediol ester. This is the preferred protecting group, but other diol protecting groups, for example but not limited to the scope of workable and known diol protecting groups, such as pinacol, 1,2-ethanediol, 1,2-propanediol, 1,3-propanediol, 2,3-butanediol, 1,2-diisopropylethanediol, 5,6-decanediol, 1,2-dicyclohexylethanediol, and others known to those skilled in the art are acceptable.

Peptide boronic esters can be prepared from commercially available materials by methods known to one skilled in the art of organic synthesis. Peptide boronic acids and esters are generally well known in the art; however, for a general reference to synthesis of peptide boronic esters, see Kettner, C; Forsyth, T. *Houben-Weyl Methods of Organic Chemistry* 1999, in press; for a reference to synthesis of fluorinated peptide residues see Matassa, V. et. al., PCT Application WO 9964442, published Dec. 12, 1999. More preferably, see techniques disclosed in copending commonly assigned U.S. Provisional Patent Application U.S. Ser. No. 60/142,561, filed Jul. 7, 1999; herein incorporated in its entirety by reference; as well as copending commonly assigned U.S. Provisional Patent Application U.S. Ser. No. 60/145,631, filed Jul. 26, 1999; herein incorporated in its entirety by reference.

Scheme 7

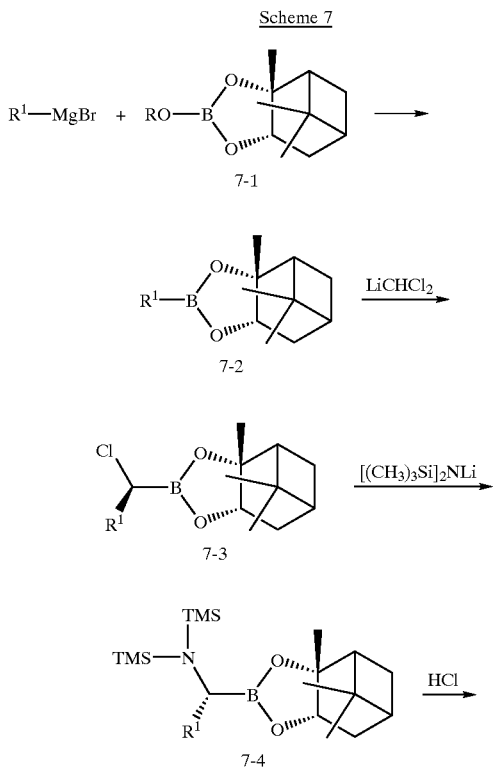

-continued

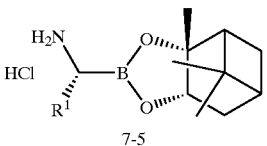

7-5 b) Synthesis of α-ketoamide, α-ketoester and α-diketone

α-Ketoamides and other α-keto derivatives are generally introduced in the hydroxy form and then oxidized to the active ketone form in the final synthetic step after coupling to the carboxylic acids 1-6 or 1-8a. Scheme 8 illustrates the synthesis of α-hydroxy esters and α-hydroxy amides. In Scheme 8, substituted acrylate ester 8-1 can be aminohydroxylated using Sharpless's procedure (Tao, B.; Sharpless, K. B., et. al. Tetrahedron Lett. 1998, 39, 2507–2510) to form Cbz-protected amino alcohol 8-2. Catalytic hydrogenation of 8-2 can give a-hydroxy ester 8-3. Alternatively, 8-2 can be hydrolyzed to tree acid 8-4 and coupled to amine $H_2N$-Q to give Cbz-protected amino α-hydroxy amide 8-5. Catalytic hydrogenation of 8-5 can give α-hydroxy ketoamide 8-6. For other methods to prepare α-keto esters, amides or other electrophilic carbonyl derivatives, see a. Wasserman, H. H. et al., *J. Org. Chem.* 1994, 59, 4364; b. Peet, N., et. al. *Tetrahedron Lett.* 1988, 3433-3436; Edwards, P. D.; Bernstein, P. R. *Medicinal Res. Reviews* 1994, 14, 127–194, and references cited therein; Sharpless, K. B.; et. al., *Angew. Chem. Int. Ed. Engl.* 1996, 35, 451; and Sharpless, K. B. et. al., *Angew. Chem. Int. Ed. Engl.* 1996, 35, 2813. Many of the α,β-unsaturated esters, 8-1, are commercially available or may be easily prepared from commercially available materials.

Amines of the formula $H_2N$-Q can be prepared from commercially available materials by methods known to one skilled in the art of organic synthesis. More preferably, see techniques disclosed in copending commonly assigned U.S. Provisional Patent Application U.S. Ser. No. 60/168,998, filed Dec. 3, 1999; herein incorporated in its entirety by reference.

Scheme 8

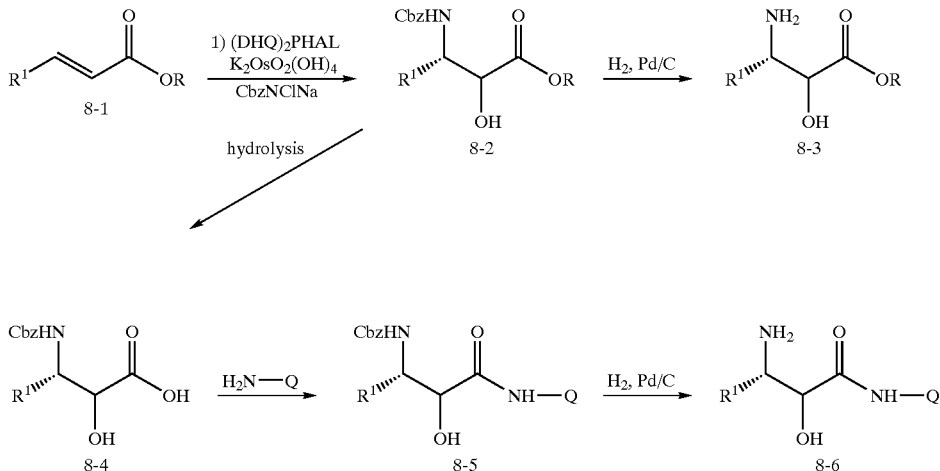

α-Hydroxyl β-amino esters can also be prepared by the method outlined in Scheme 8A. Treatment of phosphonoglycine trimethyl ester 8-7, wherein Z″ is an amino protecting group such as CBZ, with difluoroacetaldehyde hemiacetal 8-8 in the present of KO$^t$Bu yields α,β-unsaturated esters 8-9. Hydrogenation of 8-9 in the present of a chiral Rh catalyst, such as Duphos, can selectively reduce the double bond and afford 8-10 in high enantiomeric excess. DIBAL reduction of methyl esters 8-10 can give corresponding aldehyde 8-11, which under the treatment of lithium tris (methylthhio)methane to provide α-hydroxyl compound 8-12. Finally, α-hydroxyl β-amino esters of formula 8-13 can be obtained when 8-12 is treated with Hg$^{2+}$ (Kaneko, S. K.; et. al., *J. Org. Chem.* 1993, 58, 2302). Free amine 8-14 can be formed by deprotection of Cbz group under hydrogenation conditions.

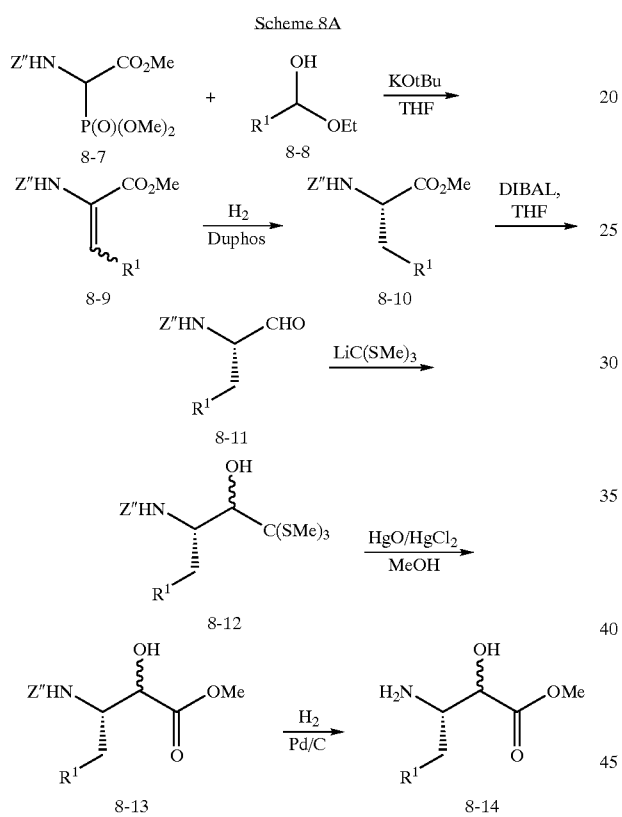

Scheme 8A c) Synthesis of Amino Trifluoromethyl and Pentafluoroethyl Ketones.

Similar to α-ketoamides and other α-keto derivatives, the trifluoromethyl or pentafluoroethyl ketone functionality is also introduced in the hydroxy form and oxidized to the active ketone form in the final step. Scheme 9 illustrates the synthesis of amino trifluoromethyl alcohol (Skiles, J. W.; et. al. *J. Med. Chem.* 1992, 35, 641–662) and amino pentafluoroethyl alcohol (Ogilvie, W. et. al *J. Med. Chem.* 1997, 40, 4113–4135). In Scheme 9, a Henry reaction between a nitroalkane R$^1$NO$_2$ and trifluoroacetaldehyde ethyl hemiacetal can afford nitro alcohol 9-1, which can be hydrogenated over Ra—Ni. The resulting amino alcohol 9-2 can be converted to the N-Boc derivative 9-3. Alternative ways to make 9-3 include treatment of 9-3a with trifluoromethyl trimethylsilane, phenyl trifluoromethyl sulphide, or trifluoromethyl halide. (a. Walter, M. W.; Adlington, R. M.; Baldwin, J. E.; Schofield, C. J. Tetrahedron 1997, 53 (21), 7275-7290; b. Yokoyama, Y.; Mochida, K.; Synlett 1996, 12, 1191–1192; c. Kitazume, T.; Ishikawa, N.; J Am Chem Soc 1985, 107, 5186). Many α-aminoaldehydes, 9-3a, are commercially available or may be easily prepared from commercially available materials by methods known to one skilled in the art of organic synthesis (For preparation of α-aminoaldehydes, see Fukuyama, T., et. al. *J. Am. Chem. Soc.* 1990, 112, 7050–7051 and Scheidt, K. A., et. al. *Bioorg. Med. Chem.* 1998, 6, 2477–2499). Treatment of the Boc-amine, 9-3, with anhydrous HCl affords the hydrochloric acid salt 9-4. A solid-phase synthesis of peptidyl trifluoromethyl ketones is also known (Poupart, M. -A., et. al. *J. Org. Chem.* 1999, 64, 1356–1361).

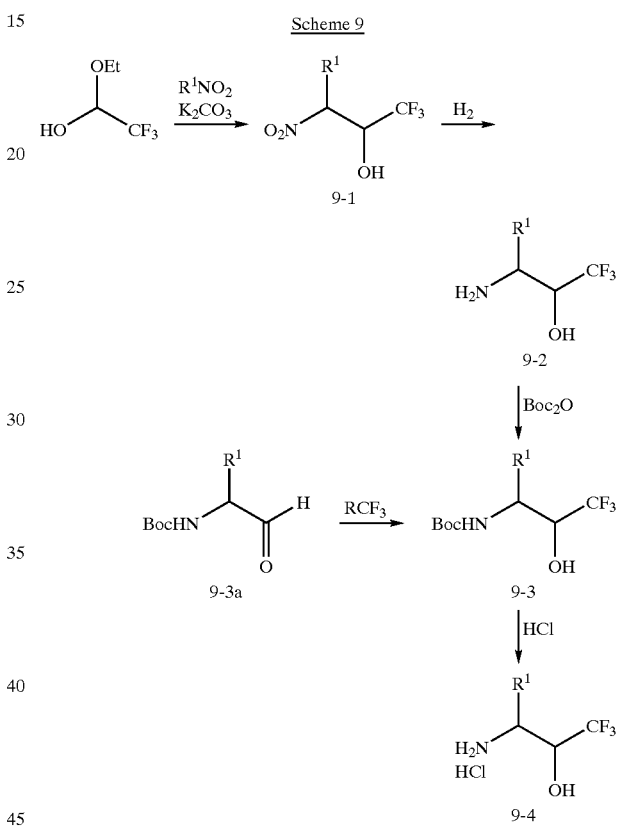

Scheme 9

Alternatively, condensation of the Weinreb amide 9-5 with CF$_3$CF$_2$Li followed by reduction with NaBH$_4$ can give pentafluoroethyl substituted alcohol 9-6 (Scheme 9A). Deprotection of 9-6 can gives the amino alcohol salt 9-7. Similar to the trifluoromethyl analogs, 9-6 can also be prepared from 9-6a by treatment with trifluoromethyl trimethylsilane, phenyl trifluoromethyl sulphide, or trifluoromethyl halide (Watanabe, S.; Fujita, T.; Sakamoto, M.; Mino, Y.; Kitazume, T. *J. Fluorine Chem.* 1995, 73 (1), 21–26).

Scheme 9A

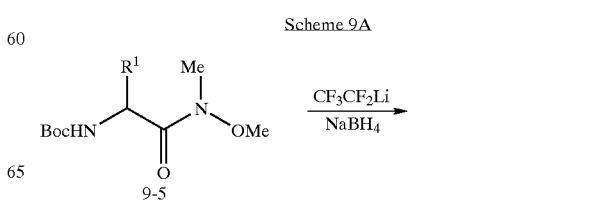

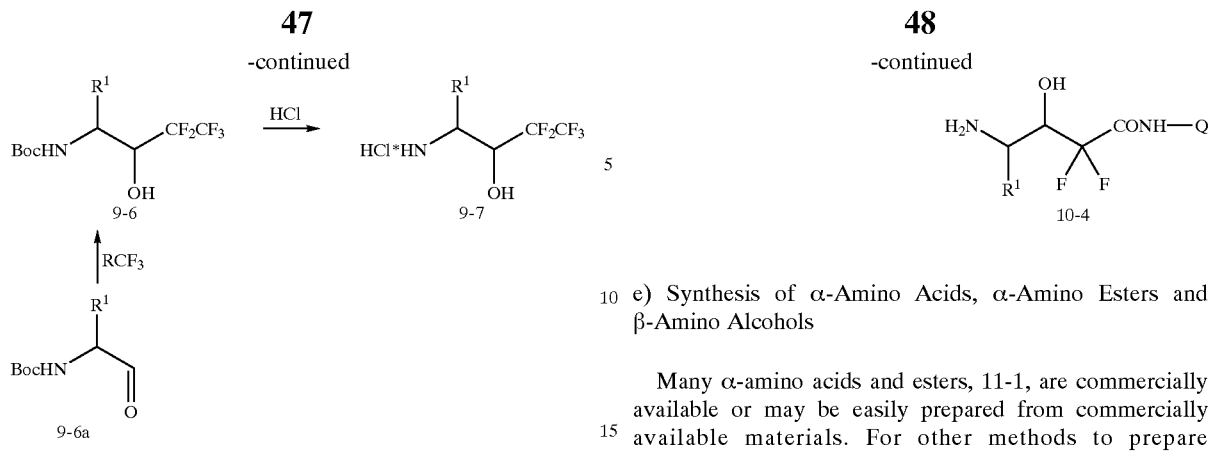

d) Synthesis of Difluoro β-ketoamide

Scheme 10 outlines the synthesis of hydroxy difluoro β-ketoamides (Veale, C. A., et. al. *J. Med. Chem.* 1997, 40, 3173–3181; Wolfe, M. S., et. al. *J. Med. Chem* 1998, 41, 6–9). In Scheme 10, protected aminoaldehyde 10-1 (see preparation of 9-3a described above) is reacted with 2-bromo-2,2-difluoroacetate to produce difluoro alcohol 10-2. The alcohol 10-2 can be hydrolyzed to the acid and coupled to an amine H$_2$N-Q to give 10-3. The nitrogen protecting group Pg can be removed according to procedures known to one skilled in the art (Greene, T. W. in Protective Groups in Organic Synthesis, John Wiley & Sons, 2$^{nd}$ Ed, 1991), producing the difluoro β-hydroxyamide 10-4.

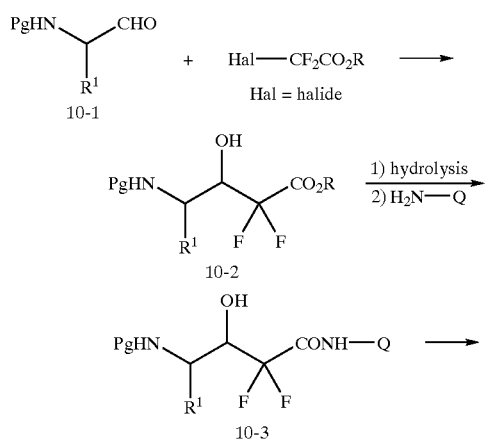

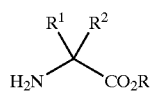

e) Synthesis of α-Amino Acids, α-Amino Esters and β-Amino Alcohols

Many α-amino acids and esters, 11-1, are commercially available or may be easily prepared from commercially available materials. For other methods to prepare α-aminoacids or esters, see WO 200009543 and WO 200009558, filed Aug. 9, 2000; herein incorporated in their entirety by reference.

11-1 R = H, alkyl, allyl, phenyl, benzyl

When R in 11-1 is not a proton, the resulting inhibitors 1-7 to 1-9 from the peptide coupling, such as 1-7 with 11-1, can be obtained from conversions of the esters of structures 1-7 to 1-9 to the corresponding acids (Greene, T. W. in *Protective Groups in Organic Synthesis*, John Wiley & Sons, 2$^{nd}$ Ed, 1991).

Scheme 11 outlines the synthesis of β-amino alcohols and O-protected β-amino alcohols. The nitrogen protecting group Pg can be added and removed, as well as the oxygen protecting group Pg' can be added and removed, according to procedures known to one skilled in the art (Greene, T. W. in *Protective Groups in Organic Synthesis*, John Wiley & Sons, 2$^{nd}$ Ed, 1991). N-protections of 11-1 can provide 11-2, which can be reduced to alcohols 11-3 (Larock, R. C. in Comprehensive Organic Transformations: A Guide to Functional Group Preparations, VCH Publishers, Inc, 1989 and references therein). O-protections of 11-3 can provide 11-4, which can undergo N-deprotections afford O-protected β-amino alcohols 11-5. N-Deprotections of 11-3 can produce β-amino alcohols 11-6.

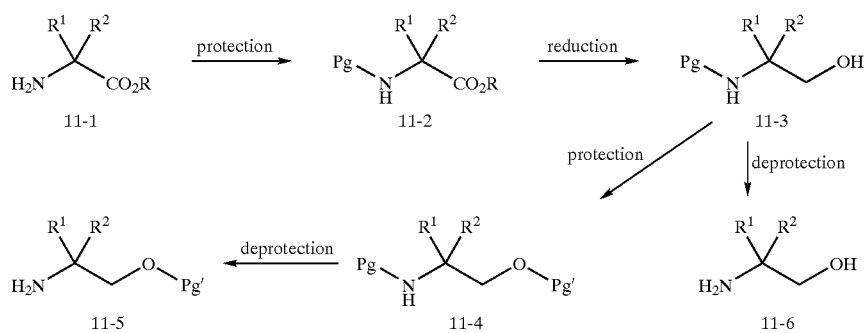

The serine traps described above are generally coupled to the free acids 1-6,1-8a, 2-2,2-2a, 1-3, or 2-4 using known peptide coupling procedures (Carpino, et. al. *J. Chem. Soc., Chem. Commun.* 1994, 201–203). The alcohol functionality of the hydroxy serine trap is oxidized by procedures known to those skilled in the art, such as Dess-Martin periodinane method (Dess, D. 1; Martin, J. C. *J. Org. Chem.* 1983, 48, 4155–4156) in the final step to give a compound of structures 1-7 to 1-9 wherein W contains an activated carbonyl. The alcohol functionality of the hydroxy serine trap in some of structures 1-7 and 3-2 needs to be protected and then deprotected in order to prepare the final compounds 1-7 and 1-9.

When required, separation of racemic materials can be achieved by HPLC using a chiral column or by a resolution using a resolving agent such as camphonic chloride (Steven D. Young, et. al., *Antimicrobial Agents and Chemotheraphy* 1995, 2602-2605). Chiral compouns may also be directly synthesized using chiral catalysts or chiral ligands (Andrew S. Thompson, et. al., *Tet. Lett.* 1995, 36, 8937–8940).

Other features of the invention will become apparent in the course of the following descriptions of exemplary embodiments which are given for illustration of the invention and are not intended to be limiting thereof.

EXAMPLES

Solution ratios express a volume relationship, unless stated otherwise. NMR chemical shifts (δ) are reported in parts per million. Flash chromatography was carried out on silica gel according to Still's method (Still, W. C., et. al., *J. Org. Chem.* 1978, 43, 2923). Abbreviations used in the Examples are defined as follows: "° C." for degrees Celsius, "MS" for mass spectrometry, "CIMS" for chemical ionization mass spectroscopy, "ESMS" for electrospray ionization mass spectroscopy, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "psi" for pond per square inch. "α", "β", "R", and "S" are stereochemical designations familiar to one skilled in the art. As used throughout the specification, the following abbreviations for chemical reagents apply:

Boc is tertbutoxycarbonyl,
Cbz is benzyloxycarbonyl,
(DHQ)$_2$PHAL is hydroquinine 1,4-phthalazinediyl diether,
Fmoc: 9-fluorenylmethoxycarbonyl,
Fmoc-Val-Cl: 9-fluorenylmethoxycarbonyl valine chloride,
DIBAL is diisobutylaluminum hydride,
DIEA is dipropylethyl amine,
DMAP is dimethylaminopyridine,
EDC is 1-(3-dimethylaminopropyl)-3-ethylcarbodiimide hydrochloride,
PyAOP is 7-azabenzotriazol-1-yloxytris(pyrrolidino)-phosphonium-hexafluorophosphate,
EDCI is 1-(3-dimethylaminopropyl)-3-ethylcarbodiimide hydrochloride,
HOAT is 1-hydroxy-7-azabenzotriazole,
TFA is trifluoroacetic acid,
TMSCN is trimethylsilyl cyanide,
p-TsOH is p-toluenesulphonic acid,
EtOAc is ethyl acetate,
CH$_2$Cl$_2$ is dichloromethane,
THF is tetrahydrofuran,
MeOH is methanol,
DMF is dimethylformamide
Cs$_2$CO$_3$ is Cesium Carbonate,
NaH is sodium hydride,
Na$_2$CO$_3$ sodium carbonate,
NaHCO$_3$ is sodium bicarbonate,
MgSO$_4$ is magnesium sulfate,
Na$_2$SO$_4$ is sodium sulfate.

Example 1

(4S)-N-{[(1R)-1-[(3αS,4S,6S,7αR)-Hexahydro-3α, 5,5-trimethyl-4,6-methano-1,3,2-benzodioxaborol-2-yl] propyl}-3-{(2S)-3-methyl-2-[(phenylacetyl)-amino]-butanoyl}-2-oxo-1-(3-phenylpropyl)-4-imidazolidinecarboxamide

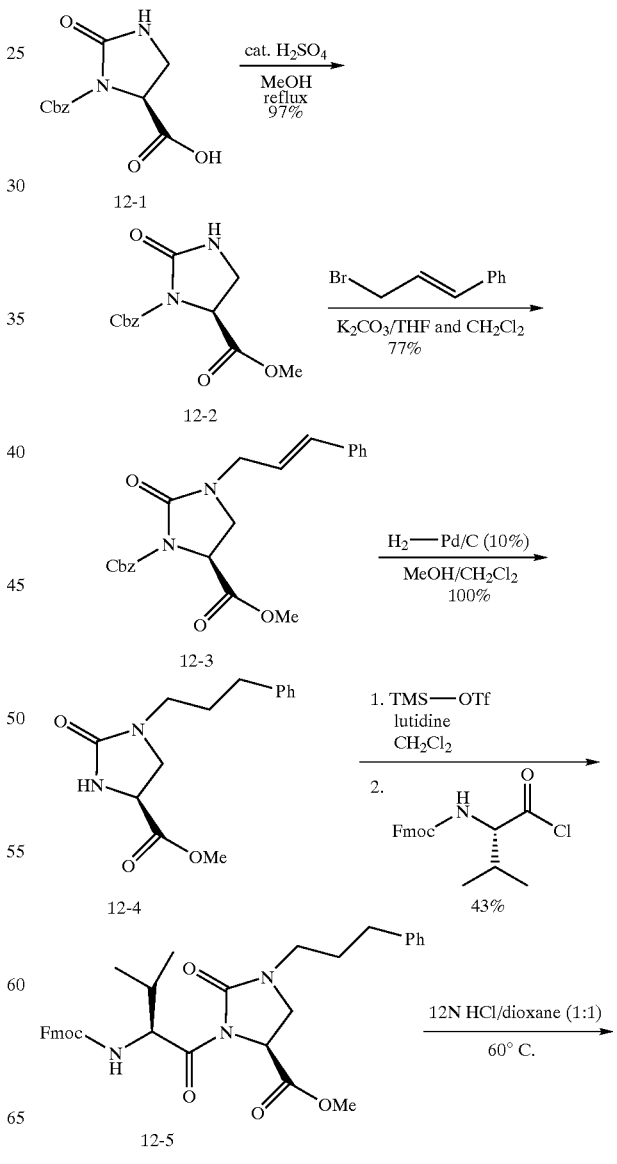

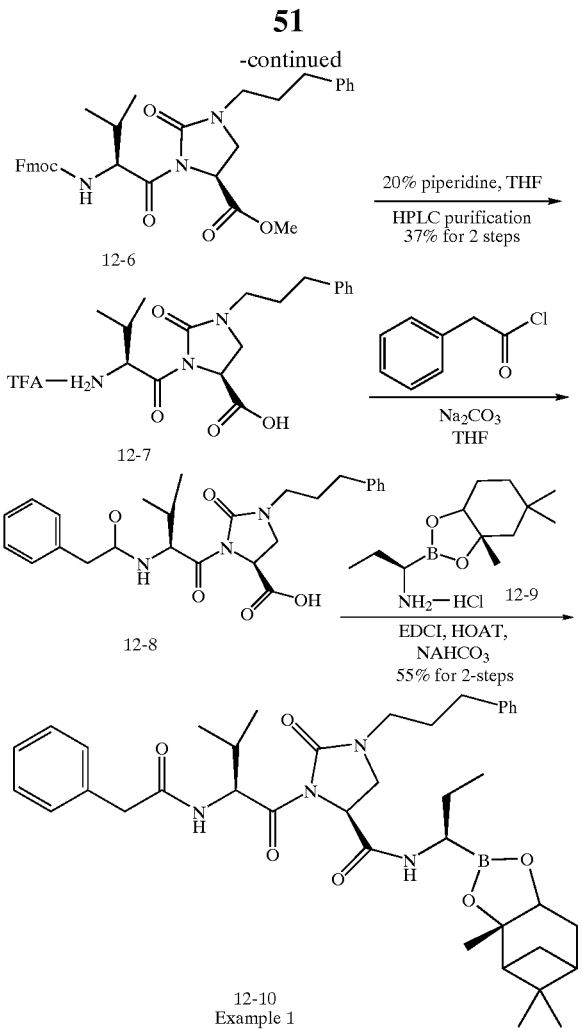

12-10
Example 1

Step 1. Formation of Methyl Ester 12-2:
To a solution of (S)-(−)-2-Oxo-1,5-imidazolidinedicarboxylic acid 1-benzyl ester (100 mmol, 26.4 g) in MeOH (500 mL) was added a catalytic amount of $H_2SO_4$ (2 ml). The reaction was refluxed overnight. After removal of MeOH, the crude product was redissolved in $CH_2Cl_2$ and washed with aqueous $NaHCO_3$. After the organic layer was dried over $Na_2SO_4$ and concentrated under full vacuum, product 12-2 (27.8 g, 100% yield) was obtained. ESMS: 279.3 $(M+H)^+$.

Step 2. Alkylation with Cinnamyl Bromide:
Several different conditions were tried for the alkylation:
a) With $K_2CO_3$/18-crown-6 as Base in THF:
To a solution of 12-2 (21.9 mmol, 6.08 g) in THF (40 mL) was added $K_2CO_3$ (26.24 mmol, 3.63 g), 18-crown-6 (0.363 g), and cinnamyl bromide (26.24 mmol, 5.2 g). The reaction mixture was stirred at 60° C. for 7 days. The reaction was diluted with EtOAc, and washed with water. After the organic layer was concentrated under vacuum and purified by flash column chromatography eluted with a gradient solvent (hexane-EtOAc), product 12-3 (6.67 g, 77%) was obtained. ESMS: 395.4 $(M+H)^+$.

b) With NaH as Base in THF:
95% Sodium Hydride (22 mmol, 0.528 g) was suspended in THF (10 mL) and cooled to 0° C. A solution of 12-2 (18 mmol, 5 g) in THF (40 mL) was added, and the mixture was allowed to warm to room temperature and stir for 1 h. To the mixture was added cinnamyl bromide (19.8 mmol, 3.9 g), and the resulting mixture was stirred at rt for 60 h. The reaction mixture was quenched with water at 0° C. and diluted with EtOAc. After the organic layer was separated, concentrated under vacuum, and purified by flash column chromatography eluted with a gradient solvent (hexane-EtOAc), 12-3 (2.1 g, 31%) was obtained. ESMS: 395.4 $(M+H)^+$.

c) With $CS_2CO_3$ as Base, in $CH_2Cl_2$:
To a solution of 12-2 (36 mmol, 10 g) in $CH_2Cl_2$ (500 mL) were added $Cs_2CO_3$ (43 mmol, 14.06 g) and then cinnamyl bromide (43 mmol, 8.5 g), and the resulting mixture was stirred at rt for 24 h. The mixture was diluted with $CH_2Cl_2$ and washed with water. After the organic layer was concentrated under vacuum and purified by flash column chromatography eluted with a gradient solvent (hexane-EtOAc), 12-3 (6.95 g, 49%) was obtained. ESMS: 395.4 $(M+H)^+$.

Step 3. Reduction of Double Bond and Deprotection of Cbz Group:
To a solution of 12-3 (2.21 g, 5.6 mmol) in a 1:1 mixture of MeOH/$CH_2Cl_2$ (250 mL total) was slowly added 10% Pd-C (0.2 g) and the mixture was treated with hydrogen on a Parr Shaker at 45 psi overnight. After filtration and concentration under vacuum, product 12-4 (1.46 g, 100%) was obtained. ESMS: 263.3 $(M+H)^+$.

Step 4. Acylation with Fmoc-Val-Cl:
To a solution of 12-4 (10.84 mmol, 2.84 g) in $CH_2Cl_2$ (25 mL) were added 2,6-lutidine (16.26 mmol, 1.89 mL) and trimethylsilyl trifluoromethanesulfonate (16.26 mmol, 2.9 mL). The solution was stirred for 30 minutes, at that time the disappearance of 12-4 was confirmed by HNMR and the formation of the TMS-intermediate was confirmed by MS spectrum. The $CH_2Cl_2$ was evaporated, and the residue was dissolved in THF (25 mL). Fmoc-Val-Cl (21.68 mmol, 7.76 g) was added, and the reaction was stirred overnight. After being diluted with EtOAc and washed with water, the organic layer was dried over $MgSO_4$ and concentrated to give crude product. The crude was purified by flash column chromatography eluted with a gradient solvent (hexane-EtOAc) to provide 12-5 (2.68 g, 43% for the two reactions). ESMS: 584.7 $(M+H)^+$.

Step 5. Hydrolysis of the Ester:
To a solution of 12-5 (2.67 mmol, 1.56 g) in dioxane (20 mL) was added 12M HCl (20 mL), and the resulting mixture was stirred at 80° C. overnight. The excess HCl and dioxane were removed by rotary evaporation followed by high vacuum, and the crude was purified by flash column chromatography eluted with a gradient solvent (hexane-EtOAc-MeOH). The product 12-6 (0.64 g) was not clean by NMR, but was taken on to the next step, after which the compound would be purified by HPLC. ESMS: 570.7 $(M+H)^+$.

Step 6. Deprotection of the Fmoc:
The partially purified 12-6 (0.64 g) was dissolved in a 20% solution of piperidine in THF (10 mL), and the resulting solution was stirred overnight. After purification by reverse-phase HPLC, pure TFA-salt 12-7 (0.344 g, 37% for two-step) was obtained. ESMS: 347.5 $(M+H)^+$.

Step 7. Coupling to Phenylacetylchloride:
To a solution of 12-7 (0.020 g, 0.058 mmol) in THF (1 mL) was added $Na_2CO_3$ (0.015 g, 0.14 mmol) and phenylacetyl chloride (0.011 g, 0.07 mmol). The reaction was allowed to stir for 3 h. The reaction mixture was loaded directly onto a preparative TLC plate and eluted with EtOAc. Product 12-8 (0.014 g, 53%) was obtained. ESMS: 466.6 $(M+H)^+$.

Step. 8. Coupling to the Boronic Ester:
To a solution of 12-8 (0.014 g, 0.031 mmol) in $CH_2Cl_2$-DMF (5:1, total 2 mL) were added (1S)-N-[(1R)-1-[(3αS,4S,6S,7α(R)-hexahydro-3α,5,5-trimethyl-4,6-methano-1,3,2-benzodioxaborol-2-yl]propyl]amine hydrochloride (12-9, 0.031 mmol, 0.085 g), HOAT (0.034 mmol, 0.046 g), EDCI (0.043 mmol, 0.082 g) and $NaHCO_3$ (0.078 mmol, 0.066 g). After stirred for 1 h, the reaction mixture was concentrated and the residue was purified by reverse-phase HPLC to give product Example 1 (12-10, 0.012 g, 55%). ESMS: 685.5 (M+H)⁺. ¹H NMR (CD₃OD) δ 7.21–7.20 (m, 4H), 7.16–7.13 (m, 5H), 7.07–7.00 (m, 1H), 5.62 (d, J=5.1 Hz, H), 4.62 (dd, J=9.9 Hz, J=4.4 Hz, 1H), 4.04 (dd, J=8.4 Hz, J=1.9 Hz, 1H), 3.56 (t, J=10.0 Hz, 1H), 3.50 (s, 2H), 3.32–3.29 (m, 2H), 3.19–3.14 (m, 1H), 2.68–2.61 (m, 1H), 2.58–2.51 (m, 2H), 2.20–2.13 (m, 2H), 2.02–1.97 (m, 1H), 1.85–1.77 (m, 2H), 1.75–1.64 (m, 2H), 1.58–1.36 (m, 2H), 1.29–1.23 (m, 2H), 1.20 (s, 3H), 1.15 (s, 3H), 0.93 (t, J=7.3 Hz, 3H), 0.90 (d, J=6.6 Hz, 3H), 0.80 (d, J=6.6 Hz, 3H), 0.71 (s, 3H).

The procedure for making the following compound is similar to preparing Example 1.

Example 2 tert-Butyl (1S)-N-{[[(1R)-1-[(3αS,4S,6S,7αR)-hexahydro-3α,5,5-trimethyl-4,6-methano-1,3,2-benzodioxaborol-2-yl]propyl)amino)carbonyl]-2-oxo-3-(3-phenylpropyl)imidazolidinyl]carbonyl}-2-methylpropylcarbamate. APMS: 667.7 (M+H)⁺. ¹H NMR (CD₃OD) δ 7.28–7.24 (m, 4H), 7.17–7.13 (m, 1H), 5.44 (d, J=4.8 Hz, 1H), 4.76 (dd, J=9.9 Hz, J=4.4 Hz, 1H), 4.12 (d, J=7.0 Hz, 1H), 3.68 (t, J=10.0 Hz, 1H), 3.43–3.36 (m, 2H), 3.27–3.14 (m, 1H), 2.74–2.57 (in, 3H), 2.29–2.06 (m, 3H), 1.93–1.88 (m, 2H), 1.85–1.73 (m, 2H), 1.66–1.47 (m, 2H), 1.42 (s, 9H), 1.37–1.24 (m, 2H), 1.29 (s, 3H), 1.24 (s, 3H), 1.00 (d, J=6.6 Hz, 3H), 0.92 (t, J=7.3 Hz, 3H), 0.87 (d, J=6.6 Hz, 3H), 0.79 (s, 3H).

Example 3

(4S)-N-{[(1R)-1-[(3αS,4S,6S,7αR)-Hexahydro-3α,5,5-trimethyl-4,6-methano-1,3,2-benzodioxaborol-2-yl]propyl}-3-{(2S)-2-[(anilinocarbonyl)amino]-3-methylbutanoyl)-2-oxo-1-(3-phenylpropyl)-4-imidazolidinecarboxamide. ESMS: 686.7 (M+H)⁺. ¹H NMR (CD₃OD) δ 7.31 (dd, J=8.8 Hz, J=15 Hz, 2H), 7.24–7.10 (m, 7H), 6.93 (t, J=7.3 Hz, 1H), 5.60 (d, J=4.0 Hz, 1H), 4.78 (dd, J=8.4 Hz, J=4.4 Hz, 1H), 4.10 (dd, J=8.4 Hz, J=1.9 Hz, 1H), 3.69 (t, J=10.0 Hz, 1H), 3.45–3.38 (m, 2H), 3.26–3.09 (m, 1H), 2.75–2.56 (m, 3H), 2.31–2.20 (m, 2H), 2.10–2.01 (m, 1H), 1.91–1.89 (m, 2H), 1.86–1.72 (m, 2H), 1.65–1.51 (m, 2H), 1.35–1.27 (m, 2H), 1.28 (s, 3H), 1.22 (s, 3H), 1.06 (d, J=6.6 Hz, 3H), 0.97 (t, J=7.3 Hz, 3H), 0.88 (d, J=6.6 Hz, 3H), 0.78 (s, 3H)

Example 4

(4S)-N-{[[(1R)-1-[(3αS,4S,6S,7αR)-Hexahydro-3α,5,5-trimethyl-4,6-methano-1,3,2-benzodioxaborol-2-yl]propyl}-3-((2S)-3-methyl-2-{[(4-methylphenyl)sulfonyl]amino}butanoyl)-2-oxo-1-(3-phenylpropyl)-4-imidazolidinecarboxamide. APMS: 721.7 (M+H)⁺. ¹H NMR (CD₃OD) δ 7.62 (d, J=8.1 Hz, 2H), 7 26 (d, J=8.8 Hz, 2H), 7.23–7.20 (m, 4H), 7.18–7.10 (m, 1H), 5.15 (d, J=5.9 Hz, 1H), 4.18 (dd, J=10.0 Hz, J=4.4 Hz, 1H), 4.05 (d, J=8.4 Hz, 1H), 3.39 (t, J=10.0 Hz, 1H), 3.35–3.28 (m, 2H), 3.20–3.13 (m, 1H), 2.69–2.58 (m, 3H), 2.37 (s, 3H), 2.22–2.15 (m, 1H), 2.02–1.93 (m, 1H), 1.89–1.70 (m, 5H), 1.57–1.43 (m, 2H), 1.33–1.22 (m, 2H), 1.21 (s, 3H), 1.18 (s, 3H), 0.92 (t, J=7.3 Hz, 3H), 0.90 (d, J=6.6 Hz, 3H), 0.84 (d, J=6.6 Hz, 3H), 0.73 (s, 3H).

Example 5

(4S)-N-{[[(1R)-1-[(3αS,4S,6S,7αR)-Hexahydro-3,5,5-trimethyl-4,6-methano-1,3,2-benzodioxaborol-2-yl]propyl}-3-((2S)-2-[(9H-fluoren-1-ylcarbonyl)amino]-3-methylbutanoyl)-2-oxo-1-(3-phenylpropyl)-4-imidazolidinecarboxamide. ESMS: 781.8 (M+Na)⁺. ¹H NMR (CD₃OD) δ 7.95 (dd, J=7.7 Hz, J=0.9 Hz, 1H), 7.83 (d, J=6.6 Hz, 1H), 7.56 (td, J=7.7 HZ, J=0.8 Hz, 2H), 7.46 (t, J=7.7 Hz, 1H), 7.38–7.27 (m, 3H), 7.25–7.45 (m, 4H), 7.17–7.11 (m, 1H), 5.96 (d, J=5.9 Hz, 1H), 4.81 (dd, J=8.4 Hz, J=4.4 Hz, 1H), 4.12 (dd, J=8.8 Hz, J=1.8 Hz, 1H), 4.09 (s, 2H), 3.71 (t, J=10.0 Hz, 1H), 3.49–3.40 (m, 2H), 3.34–3.30 (m, 1H), 2.76–2.61 (m, 3H), 2.37–2.33 (m, 1H), 2.08–2.01 (m, 1H), 1.97–1.90 (m, 3H), 1.88–1.80 (m, 2H), 1.77–1.48 (m, 2H), 1.35–1.31 (m, 2H), 1.28 (s, 3H), 1.22 (s, 3H), 1.14 (d, J=7.0 Hz, 3H), 1.02 (d, J=7.0 Hz, 3H), 0.98 (t, J=7.3 Hz, 3H), 0.78 (s, 3H)

Example 6

(4S)-N-{[[(1R)-1-[(3αS,4S,6S,7αR)-Hexahydro-3α,5,5-trimethyl-4,6-methano-1,3,2-benzodioxaborol-2-yl]propyl}-3-((2S)-2-([(4-methoxyphenyl)acetyl]amino}-3-methylbutanoyl)-2-oxo-1-(3-phenylpropyl)-4-imidazolidinecarboxamide. ESMS (−): 814.7 (M+TFA-H)—. ¹H NMR (CD₃OD) δ 7.18–7.15 (m, 6H), 7.10–7.06 (m. 1H), 6.81 (d, J=8.4 Hz, 2H), 5.66 (d, J=4.8 Hz, 1H), 4.66 (dd, J=10.2 Hz, J=4.4 Hz, 1H), 4.08 (d, J=8.4 Hz, 1H), 3.72 (s, 3H), 3.61 (t, J=10.0 Hz, 1H), 3.47 (s, 2H), 3.39–3.32 (m, 2H), 3.23–3.16 (m, 1H), 2.73–2.53 (m, 3H), 2.25–2.18 (m, 2H), 2.10–2.02 (m, 1H), 1.89–1.82 (m, 2H), 1.77–1.69 (m, 2H), 1.58–1.45 (m, 2H), 1.33–1.27 (m, 1H), 1.25 (s, 3H), 1.20 (s, 3H), 0.95 (t, J=7.3 Hz, 3H), 0.93 (d, J=6.6 Hz, 3H), 0.83 (d, J=6.6 Hz, 3H), 0.75 (s, 3H).

Example 7

(4S)-N-{[(1R)-1-[(3αS,4S,6S,7αR)-Hexahydro-3α,5,5-trimethyl-4,6-methano-1,3,2-benzodioxaborol-2-yl]-3-butenyl}-3-((2S)-2-[(9H-fluoren-1-ylcarbonyl)amino]-3-methylbutanoyl)-2-oxo-1-(3-phenylpropyl)-4-imidazolidinecarboxamide To a solution of 12-6 (0.010 g, 0.018 mmol) in CH₂Cl₂-DMF (5:1, total 2 mL) were added N-[(1R)-1-[(3αS,4S,6S,7αR)-hexahydro-3α,5,5-trimethyl-4,6-methano-1,3,2-benzodioxaborol-2-yl]-3-butenyl]amine (1-9, 0.020 mmol, 0.0052 g), HOAT (0.020 mmol, 0.0027 g), EDCI (0.025 mmol, 0.0048 g) and NaHCO₃ (0.045 mmol, 0.0038 g). After stirred for 1 h, the reaction mixture was concentrated and the residue was purified by reverse-phase HPLC to give the title product (0.0038 g, 26%). ESMS: 801.8 (M+H)⁺. ¹H NMR (CDCl₃) δ 7.77 (d, J=7.3 Hz, 2H), 7.61 (d, J=7.0 Hz, 2H), 7.40 (t, J=7.3 Hz, 2H), 7.31 (t, J=7.0 Hz, 2H), 7.24–7.17 (m, 5H), 6.55 (d, J=5.5 Hz, 1H), 5.78–5.72 (m 1H), 5.58 (bs, 1H), 5.10 (d, J=10.6 Hz, 1H), 5.06 (s, 1H), 4.68 (dd, J=8.8 Hz, J=2.9 Hz, 1H), 4.38–4.26 (m, 4H), 3.48 (t, J=10.0 Hz, 1H), 3.42–3.26 (m, 3H), 2.69–2.61 (m, 3H), 2.33–2.28 (m, 2H), 2.23–2.11 (m, 1H), 2.04–1.65 (m, 3H), 1.56–1.54 (m, 4H), 1.40 (bs, 2H), 1.37 (s, 3H), 1.28 (s, 3H), 1.09 (d, J=6.6 Hz, 3H), 0.87 (d, J=6.6 Hz, 3H), 0.83 (s, 3H).

Example 8

9H-Fluoren-9-ylmethyl(1S)-N-{[[(1R)-1-[(3αS,4S,6S,7αR)-hexahydro-3α,5,5-trimethyl-4,6-methano-1,3,2-benzodioxaborol-2-yl]propyl]amino)carbonyl]-2-oxo-3-(3-phenylpropyl)imidazolidinyl]carbonyl}-2-methylpropylcarbamate The procedure for coupling 12-6 with (1S)-N-[(1R)-1-[(3αS,4S,6S,7αR)-hexahydro-3α,5,5-trimethyl-4,6-methano-1,3,2-benzodioxaborol-2-yl]propyl]amine hydrochloride (12-9) to make the title compound is the same as for preparing Example 7. ESMS: 789.8 (M+H)⁺. ¹H NMR (CD₃OD) δ 7.75 (d, J=7.3 Hz, 2H), 7.63 (d, J=7.0 Hz, 2H), 7.34 (t, J=7.3 Hz, 2H), 7.26 (t, J=7.3 Hz, 2H), 7.18–7.11 (m, 5H), 5.49 (d, J=4.8 Hz, 1H), 4.71 (dd, J=10.2 Hz, J=4.4 Hz, 1H), 4.29 (d, J=6.9 Hz, 1H), 4.19 (d, J=6.9 Hz, 1H), 4.09 (d, J=6.9 Hz, 1H), 3.63 (t, J=10.0 Hz, 1H), 3.38–3.30 (m, 2H), 3.23–3.22 (m, 1H), 2.72–2.56 (m, 3H), 2.21–2.18 (m, 2H), 2.06–1.99 (m, 1H), 1.89–1.69 (m, 3H), 1.61–1.46 (m, 2H), 1.33–1.31 (m, 2H), 1.25 (s, 3H), 1.20 (s, 3H), 0.97 (t, J=7.3 Hz, 3H), 0.96 (d, J=7.0 Hz, 3H), 0.87 (d, J=7.0 Hz, 3H), 0.75 (s, 3H).

Example 9

(4S)-N-{[[(1R)-1-[(3αS,4S,6S,7αR)-Hexahydro-3α,5,5-trimethyl-4,6-methano-1,3,2-benzodioxaborol-2-yl]

propyl}-3-((2S)-3-methyl-2-{[3-(trifluoromethyl)benzyl]amino} butanoyl)-2-oxo-1-(3-phenylpropyl)-4-imidazolidinecarboxamide To a solution of Example 7 (14 mg, 0.018 mmol) in THF (0.8 mL) was added piperidine (0.2 mL) and the mixture was stirred at rt for 1 h and then concentrated under full vacuum. To a solution of the residue in MeOH (0.1 mL) were added 3-(trifluoromethyl)benzaldehyde (3.1 mg, 0.018 mmol) and NaBH$_4$ (0.7 mg, 0.018 mmol). The mixture was stirred at 65° C. for 1.5 h and then at rt for 18 h. The mixture was purified by HPLC to provide pure title compound (4.5 mg, 34.5%). ESMS: 725.8 (M+H)$^+$. $^1$H NMR (CD$_3$OD) δ 8.29–8.20 (m, 1H), 7.81–7.72 (m, 2H), 7.64 (t, J=7.3 Hz, 1H), 7.40–7.35 (m, 1H), 7.26–7.14 (m, 4H), 5.29 (d, J=4.1 Hz, 1H), 4.68 (dd, J=10.2 Hz, J=4.4 Hz, 1H), 4.31 (s, 2H), 4.16 (d, J=6.6 Hz, 1H), 3 67 (t, J=10.0 Hz, 1H), 3.47–3.31 (m, 2H), 3.20–3.14 (m, 1H), 2.89–2.84 (m, 1H), 2.70–2.59 (m, 2H), 2.39–2.09 (m, 3H), 2.01–1.90 (m, 2H), 1.87–1.79 (in, 5H), 1.61–1.46 (m, 2H), 1.31–1.29 (m, 2H), 1.29 (s, 3H), 1.23 (s, 3H), 1.10 (d, J=7.0 Hz, 3H), 1.05 (d, J=7.0 Hz, 3H), 0.99 (t, J=7.3 Hz, 3H), 0.79 (s, 3H).

Example 10

(4S)-N-{[[(1R)-1-(3αS,4S,6S,7αR)-Hexahydro-3α,5,5-trimethyl-4,6-methano-1,3,2-benzodioxaborol-2-yl]propyl}-3-{(2s)-2-[([1,1'-biphenyl]-4-ylmethyl)amino]3-methylbutanoyl}-2-oxo-1-(3-phenylpropyl)-4-imidazolidinecarboxamide The procedure to make the title compound is the same as for preparing Example 9. ESMS: 733.8 (M+H)$^+$. $^1$H NMR (CD$_3$OD) δ 8.10–7.95 (m, 1H), 7.69–7.612 (m, 3H), 7.52–7.49 (m, 1H), 7.43–7.40 (m, 5H), 7.25–7.23 (m, 1H), 7.19–7.14 (m, 3H), 5.27 (d, J=4.0 Hz, 1H), 4.86 (dd, J=10.2 Hz, J=4.0 Hz, 1H), 4.31 (d, J=10.0 Hz, 1H), 4.26 (s, 2H), 3.48 (t, J=10.0 Hz, 1H), 3.25–3.17 (m, 3H), 2.58–2.53 (m, 1H), 2.41–2.25 (m, 3H), 2.00–1.85 (m, 6H), 1.55–1.47 (m, 2H), 1.30 (s, 3H), 1.29–1.24 (m, 2H), 1.09 (d, J=7.0 Hz, 3H), 1.05 (d, J=7.0 Hz, 3H), 0.97 (d, J=7.0 Hz, 3H), 0.92 (t, J=7.3 Hz, 3H), 0.85 (s, 3H).

Example 11

9H-Fluoren-9-ylmethyl (1S)-1-(((5S)-5-[({(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-[(2-phenyl-4-quinolinyl)methyl]imidazolidinyl}carbonyl)-2-methylpropylcarbamate The procedure to make the title compound is similar to the preparation of Example 1 if cinnamyl bromide is by replaced with 4-(bromomethyl)-2-phenylquinoline in step 2 and if NaH is used as the base in THF as solvent. ESMS: 888.9 (M+H)$^+$. $^1$H NMR (CD$_3$OD) δ 8.34 (d, J=8.1 Hz, 1H), 8.28–8.23 (m, 2H), 8.18–8.05 (m, 2H), 7.99 (t, J=7.7 Hz, 1H), 7.79 (d, J=7.7 Hz, 2H), 7.66 (d, J=6.6 Hz, 2H), 7.61–7.58 (m, 3H), 7.51–7.40 (m, 1H), 7.37 (t, J=7.3 Hz, 2H), 7.29 (t, J=7.3 Hz, 2H), 5.61 (d, J=6.4 Hz, 1H), 5.33 (d, J=12.4 Hz, 1H), 4.96 (d, J=12.1 Hz, 1H), 4.32 (d, J=7.3 Hz, 1H), 4.22 (t, J=7.0 Hz, 1H), 4.16 (t, J=10.0 Hz, 1H), 4.01 (t, J=10.2 Hz, 1H), 3.87–3.83 (m, 1H), 2.62–2.58 (m, 1H), 2.25–2.10 (m, 2H), 2.10–2.00 (m, 1H), 1.90–1.87 (m, 1H), 1.73–1.62 (m, 2H), 1.53–1.35 (m, 2H), 1.27–1.259 (m, 2H), 1.20 (s, 3H), 1.18 (s, 3H), 1.01 (d, J=6.6 Hz, 3H), 0.92 (d, J=6.8 Hz, 3H), 0.76 (t, J=7.3 Hz, 3H), 0.74 (s, 3H).

Example 12

N-((1S)-1-{[(5S)-5-{[[(1R)-1-[(3αS,4S,6S,7αR)-Hexahydro-3α,5,5-trimethyl-4,6-methano-1,3,2-benzodioxaborol-2-yl]propyl}-amino)carbonyl]-2-oxo-3-(3-phenylpropyl)imidazolidinyl]carbonyl}-2-methylpropyl)-2-chloronicotinamide. ESMS: 706.2 (M+H)$^+$. $^1$H NMR (CD$_3$OD) δ 8.42 (dd, J=4.8 Hz, J=1.9 Hz, 1H), 7.85 (dd, J=7.7 Hz, J=1.8 Hz, 1H), 7.44 (dd, J=7.7 Hz, J=5.2 Hz, 1H), 7.25–7.23 (m, 4H), 7.13–7.05 (m, 1H), 5.93 (dd, J=9.8 Hz, J=4.7 Hz, 1H), 4.75 (dd, J=10.6 Hz, J=5.8 Hz, 1H), 4.12 (d, J=7.3 Hz, 1H), 3.69 (t, J=9.9 Hz, 1H), 3.43–3.33 (m, 2H), 3.21–3.15 (m, 1H), 2.82–2.60 (m, 3H), 2.44–2.08 (m, 3H), 1.99–1.84 (m, 3H), 1.78–1.72 (m, 2H), 1.66–1.49 (m, 2H), 1.36–1.30 (m, 2H), 1.27 (s, 3H), 1.23 (s, 3H), 1.11 (d, J=7.0 Hz, 3H), 0.97 (t, J=7.3 Hz, 3H), 0.96 (d, J=6.8 Hz, 3H), 0.78 (s, 3H).

Example 13

(4S)-N-{[[(1R)-1-[(3αS,4S,6S,7αR)-Hexahydro-3α,5,5-trimethyl-4,6-methano-1,3,2-benzodioxaborol-2-yl]propyl}-3-{(2S)-2-[(4-butylbenzoyl)amino]-3-methylbutanoyl}-2-oxo-1-(3-phenylpropyl)-4-imidazolidinecarboxamide. ESMS: 727.4 (M+H)$^+$. $^1$H NMR (CD$_3$OD) δ 7.66 (d, J=8.4 Hz, 2H), 7.20 (d, J=8.4 Hz, 2H), 7.17–7.16 (m, 4H), 7.13–7.06 (m, 1H), 5.82 (d, J=6.2 Hz, 1H), 4.71 (dd, J=10.3 Hz, J=4.1 Hz, 1H), 4.04 (d, J=8.4 Hz, 1H), 3.63 (t, J=10.3 Hz, 1H), 3.41–3.24 (m, 2H), 3.18–3.15 (m, 1H), 2.69–2.50 (m, 5H), 2.28–2.13 (m, 2H), 2.01–1.97 (m, 1H), 1.88–1.81 (m, 3H), 1.73–1.65 (m, 1H), 1.56–1.40 (m, 5H), 1.31–1.26 (m, 4H), 1.20 (s, 3H), 1.15 (s, 3H), 1.02 (d, J=6.6 Hz, 3H), 0.93 (d, J=6.6 Hz, 3H), 0.91 (t, J=7.3 Hz, 3H), 0.85 (t, J=7.3 Hz, 3H), 0.71 (s, 3H).

Example 14

Isobutyl (1S)-1-{[(5S)-5-{[[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl)imidazolidinyl]carbonyl}-2-methylpropylcarbamate. ESMS: 667.2 (M+H)$^+$. $^1$H NMR (CDCl$_3$) δ 7 24-7.22 (m, 2H), 7 17-7.13 (m, 2H), 6.54 (d, J=5 9 Hz, 1H), 5.51 (bs, 1H), 5.24 (bs, 1H), 4.68 (dd, J=9.5 Hz, J=3.2 Hz, 1H), 4.26 (dd, J=6.6 Hz, J=3.0 Hz, 1H), 3.82–3.77 (m, 3H), 3.41 (t, J=9.5 Hz, 1H), 3.37–3.29 (m, 1H), 3.25–3.18 (m, 2H), 2.69–2.57 (m, 2H), 2.34–2.24 (m, 2H), 2.23–2.13 (m, 1H), 1.99 (t, J=5.7 Hz, 1H), 1.88–1.86 (m, 3H), 1.68–1.54 (m, 3H), 1.40–1.34 (m, 2H), 1.25 (s, 3H), 1.23 (s, 6H), 1.03 (d, J=6.8 Hz, 3H), 0.90–0.87 (m, 6H), 0.82 (d, J=7.1 Hz, 3H), 0.80 (s, 3H).

Example 15

(4S)-N-{[[(1R)-1-[(3αS,4S,6S,7αR)-Hexahydro-3α,5,5-trimethyl-4,6-methano-1,3,2-benzodioxaborol-2-yl]propyl}-3-((2S)-2-{[(benzoylamino)carbonyl]amino}-3-methylbutanoyl)-2-oxo-1-(3-phenylpropyl)-4-imidazolidinecarboxamide. ESMS: 714.3 (M+H)$^+$. $^1$H NMR (CDCl$_3$) δ 9.34 (d, J=8.6 Hz, 1H), 8.80 (s, 1H), 7.90 (dd, J=7.0 Hz, J=1.5 Hz, 2H), 7.60 (t, J=7.3 Hz, 1H), 7.51 (t, J=7.3 Hz, 2H), 7.29–7.28 (m, 3H), 7.21–7.19 (m, 2H), 6.69 (d, J=5.9 Hz, 1H), 5.80 (dd, J=7.3 Hz, J=37 Hz, 1H), 4.75 (dd, J=9.5 Hz, J=3.2 Hz, 1H), 4.31 (dd, J=8.8 Hz, J=1.9 Hz, 1H), 3.84 (dd, J=9.3 Hz, J=3.0 Hz, 1H), 3.46 (t, J=9.5 Hz, 1H), 3.40 (t, J=7.2 Hz, 1H), 3.29 (t, J=7.3 Hz, 1H), 3.25–3.20 (m, 1H), 2.74–2.60 (m, 2H), 2.48–2.41 (m, 1H), 2.36–2.26 (m, 2H), 2.02–1.99 (m, 1H), 1.95–1.81 (m, 3H), 1.74–1.65 (m, 1H), 1.62–1.54 (m. 1H), 1.40 (s, 2H), 1.28–1.26 (m. 6H), 1.13 (d, J=6.6 Hz, 3H), 0.96 (d, J=6.6 Hz, 3H), 0.94 (t, J=7.5 Hz, 3H), 0 83 (s, 3H)

Example 16

(4S)-N-{[[(1R)-1-[(3αS,4S,6S,7αR)-Hexahydro-3,5,5-trimethyl-4,6-methano-1,3,2-benzodioxaborol-2-yl]propyl}-3-[(2S)-3-methyl-2-(1-naphthoylamino)butanoyl]-2-oxo-1-(3-phenylpropyl)-4-imidazolidinecarboxamide. ESMS: 721.3 (M+H)$^+$. $^1$H NMR (CDCl$_3$) δ 8.37 (d, J=8.3 Hz, 1H), 7.93 (d, J=8.3 Hz, 1H), 7.87 (dd, J=7.4 Hz, J=1.5 Hz, 1H), 7.69

(dd, J=7.1 Hz, J=1.1 Hz, 1H), 7.57–7.50 (m, 2H), 7.47 (t, J=7.2 Hz, 1H), 7.34–7.27 (m, 2H), 7.22–7.17 (m, 3H), 6.61 (d, J=5.6 Hz, 2H), 6.08 (bs, 1H), 4.76 (dd, J=9.5 Hz, J=3.2 Hz, 1H), 4.29 (dd, J=8.8 Hz, J=2.2 Hz, 1H), 3.83 (dd, J=9.3 Hz, J=3.3 Hz, 1H), 3.52 (t, J=9.5 Hz, 1H), 3.46–3.41 (m, 1H), 3.33–3.29 (m, 1H), 3.24–3.21 (m, 1H), 2.75–2.63 (m, 3H), 2.51–2.45 (m, 1H), 2.39–2.28 (m, 1H), 2.19–2.15 (m, 1H), 2.04–2.00 (m, 1H), 1.96–1.92 (m, 3H), 1.90–1.80 (m, 1H), 1.72–1.68 (m, 1H), 1.59–1.54 (m, 1H), 1.27 (d. J=5.6 Hz, 3H), 1.21 (d. J=6.6 Hz, 3H), 1.18 (d, J=6.6 Hz, 3H), 0.92 (d, J=6.6 Hz, 3H), 0.90 (t, J=7.3 Hz, 3H), 0.82 (s, 3H).

Example 17

(4S)-N-{[[(1R)-1-[(3αS,4S,6S,7αR)-Hexahydro-3α,5,5-trimethyl-4,6-methano-1,3,2-benzodioxaborol-2-yl]propyl}-3-[(2S)-2-(acetylamino)-3-methylbutanoyl]-2-oxo-1-(3-phenylpropyl)-4-imidazolidinecarboxamide. ESMS: 631.6 (M+Na)$^+$. $^1$H NMR (CD$_3$OD) δ 7.26–7.21 (m, 4H), 7.20–7.10 (m, 1H), 5.68 (d, J=5.1 Hz, 1H), 4.73 (dd, J=9.5 Hz, J=3.7 Hz, 1H), 4.10 (d, J=8.8 Hz, 1H), 3.67 (t, J=10.3 Hz, 1H), 3.41–3.34 (m, 2H), 3.26–3.24 (m, 1H), 2.76–2.55 (m, 3H), 2.35–2.10 (m, 2H), 2.08–2.00(m, 1H), 1.96 (s, 3H), 1.91–1.88 (m, 3H), 1.83–1.76 (m, 2H), 1.71–1.56 (m, 2H), 1.53–1.44 (m, 2H), 1.27 (s, 3H), 1.22 (s, 3H), 1.01 (d. J=7.0 Hz, 3H), 0.97 (t, J=7.3 Hz, 3H), 0.91 (d. J=7.0 Hz, 3H), 0.77 (s, 3H).

Example 18

(4S)-N-{[[(1R)-1-[(3αS,4S,6S,7αR)-Hexahydro-3α,5,5-trimethyl-4,6-methano-1,3,2-benzodioxaborol-2-yl]]propyl}-3-[(2S)-2-(benzoylamino)-3-methylbutanoyl]-2-oxo-1-(3-phenylpropyl)-4-imidazolidinecarboxamide. ESMS: 671.5

(M+H)$^+$. $^1$H NMR (CD$_3$OD) δ 7.81 (d, J=7.0 Hz, 2H), 7.52 (t, J=7.0 Hz, 1H), 7.43 (t, J=7.0 Hz, 2H), 7.24–7.22 (d, J=4.0 Hz, 4H), 7.17–7.11 (m, 1H), 5.91 (d, J=5.9 Hz, 1H), 4.76 (dd, J=8.6 Hz, J=4.4 Hz, 1H), 4.12 (d, J=8.4 Hz, 1H), 3.69 (t, J=10.0 Hz, 1H), 3.521–3.38 (m, 2H), 3.24–3.22 (m, 1H), 2.77–2.61 (m, 3H), 2.38–2.19 (m, 2H), 2.10–2.00(m, 1H), 1.98–1.80 (m, 3H), 1.79–1.72 (m, 2H), 1.66–1.47 (m, 2H), 1.38–1.34 (m, 2H), 1.287 (s, 3H), 1.22 (s, 3H), 1.09 (d. J=6.6 Hz, 3H), 1.00 (d. J=6.6 Hz, 3H), 0.97 (t, J=7.3 Hz, 3H), 0.77 (s, 3H).

Example 19

Benzyl (5S)-5-[({(1R)-1-[(3αS,4S,6S,7αR)-hexahydro-3α,5,5-trimethyl-4,6-methano-1,3,2-benzodioxaborol-2-yl]-3-butenyl}amino)carbonyl]-2-oxo-3-[(2E)-3-phenyl-2-propenyl]-1-imidazolidinecarboxylate To a solution of 12-3 (1 g, 2.53 mmol) in THF (5 mL) was added LiOH—H$_2$O (0.319 g, 7.6 mmol) at −10° C., and the resulting mixture was stirred at −10 to 0° C. for 30 min. The mixture was concentrated and the residue was dissolved in EtOAc and neutralized with 12M HCl. The organic layer was concentrated to yield the corresponding acid (0.868 g, 90%). The procedure to make the title compound via peptide coupling of this acid with N-[(1R)-1-[(3αS,4S,6S,7αR)-hexahydro-3α,5,5-trimethyl-4,6-methano-1,3,2-benzodioxaborol-2-yl]-3-butenyl]amine (1-9) is similar to that for preparation of Example 7. ESMS: 612.5 (M+H)$^+$. $^1$H NMR (CDCl$_3$) δ 7.39–7.19 (m, 10H), 6.57 (d, J=15.7 Hz, 1H), 6.07 (td, J=15.7 Hz, J=6.6 Hz, 1H), 5.76–5.67 (m, 1H), 5.30 (d, J=12.1 Hz, 1H), 5.21 (d, J=12.1 Hz, 1H), 5.00–4.99 (m, 1H), 4.95 (bs, 1H), 4.75 (d, J=10.0 Hz, J=3.7 Hz, 1H), 4.25 (dd, J=8.8 Hz, J=2.2 Hz, 1H), 4.11–3.96 (m, 1H), 3.69 (t, J=10.0 Hz, 1H), 3.59 (dd, J=10.0 Hz, J=3.7 Hz, 1H), 3.14–3.10 (m, 1H), 2.40–2.10 (m, 4H), 1.98 (t, J=5.6 Hz, 1H), 1.87–1.77 (m, 2H), 1.41 (s, 2H), 1.26 (s, 6H), 0.81 (s, 3H).

Example 20

Benzyl (5S)-5-[({(1R)-1-[(3αS,4S,6S,7αR)-hexahydro-3α,5,5-trimethyl-4,6-methano-1,3,2-benzodioxaborol-2-yl]-3-butenyl}amino)carbonyl]-3-(2-anilino-2-oxoethyl)-2-oxo-1-imidazolidinecarboxylate

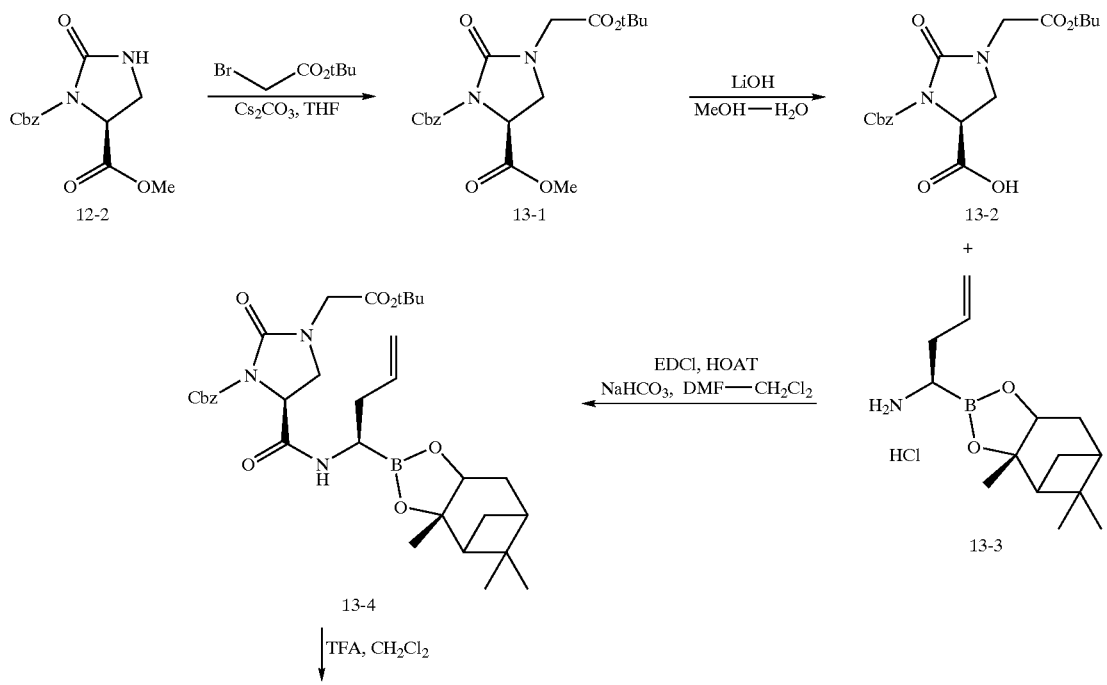

-continued

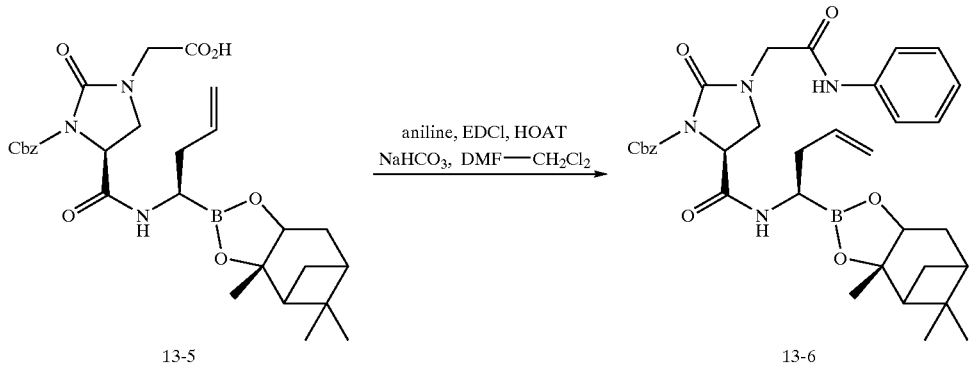

To a solution of 12-2 (20 mmol, 5.56 g) in CH₂Cl₂ (80 mL) were added Cs₂CO₃ (24 mmol, 7.82 g) and tert-butyl-2-bromoacetate (24 mmol, 3.5 mL) and the resulting mixture was stirred at rt for 24 h. The reaction mixture was diluted with EtOAc (100 mL) and washed with water and brine. The organic layer was dried over MgSO₄ and concentrated under full vacuum to give 13-1 (8.15 g, 100%). ESMS: 393.4 (M+H)⁺.

The procedures for hydrolysis of 13-1 and peptide coupling of acid 13-2 with N-[(1R)-1-[(3αS,4S,6S,7αR)-Hexahydro-3α,5,5-trimethyl-4,6-methano-1,3,2-benzodioxaborol-2-yl]-3-butenyl]amine (1-9) are similar to that preparation of Example 12. Hydrolysis of tert-butyl ester of 13-4 with 20% TFA in CH₂Cl₂ at rt for 3 h provide {(4S)-4-[({(1R)-1-[(3αS)-3α,5,5-trimethylhexahydro-1,3, 2-benzodioxaborol-2-yl]-3-butenyl}amino) carbonyl]-3 [(benzyloxy)carbonyl]-2-oxoimidazolidinyl)acetic acid. The procedure of coupling acid 13-5 with aniline is the same as described above as the peptide coupling reaction. ESMS: 612.5 (M+H)⁺. ¹H NMR (CD₃OD) δ 9.79 (s, 1H), 8.94 (s, 1H), 7.57 (d, J=8.4 Hz, 2H), 7.40 (d, J=6.2 Hz, 2H), 7.37–7.26 (m, 5H), 7.08 (t, J=7.3 Hz, 1H), 5.86–5.73 (m, 1H), 5.24 (d, J=12.1 Hz, 1H), 5.18 (d, J=12.1 Hz, 1H), 5.00 (d, J=14.7 Hz, 1H), 4.96 (d, J=9.1 Hz, 1H), 4.80 (dd, J=10.3 Hz, J=3.7 Hz, 1H), 4.21 (dd, J=8.8 Hz, J=1.8 Hz, 1H), 4.08 (d, J=7.7 Hz, 1H), 3.87 (t, J=9.8 Hz, 1H), 3.44 (dd, J=9.6 Hz, J=3.7 Hz, 1H), 2.94–2.88 (m, 1H, 2.33-2.20 (m, 3H), 2.13–2.08 (m, 1H), 1.93 (t, J=5.1 Hz, 1H), 1.82–1.74 (m, 2H), 1.35–1.27 (m, 2H), 1.30 (s, 3H, 1.25 (s, 3H), 0.82 (s, 3H).

TABLE 1

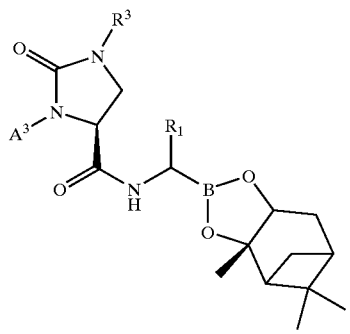

| Ex. | R¹ | A³ | R³ | Mass Spec (M + H, 100%) |
|---|---|---|---|---|
| 1 | Et | PhCH₂C(=O)—Val— | Ph(CH₂)₃— | ES+: 685.5 |
| 2 | Et | Boc—Val— | Ph(CH₂)₃— | AP+: 667.7 |
| 3 | Et | PhNHC(=O)—Val— | Ph(CH₂)₃— | ES+: 686.7 |
| 4 | Et | Me—C₆H₄—S(O)₂—Val— | Ph(CH₂)₃— | AP+: 721.7 |
| 5 | Et | Fluorenyl-C(=O)—Val— | Ph(CH₂)₃— | ES+: 781.8 (M + Na, 100%) |

TABLE 1-continued
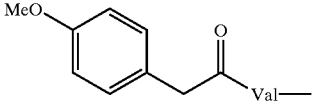
| Ex. | R¹ | A³ | R³ | Mass Spec (M + H, 100%) |
|---|---|---|---|---|
| 6 | Et | 4-MeO-C₆H₄-CH₂-C(O)-Val— | Ph(CH₂)₃— | ES−: 814.7 (M + TFA-H, 100%) |
| 7 | allyl | Fmoc—Val— | Ph(CH₂)₃— | ES+: 801.8 |
| 8 | Et | Fmoc—Val— | Ph(CH₂)₃— | ES+: 789.8 |
| 9 | Et | 3-F₃C-C₆H₄-CH₂-Val— | Ph(CH₂)₃— | ES+: 725.8 |
| 10 | Et | 4-Ph-C₆H₄-CH₂-Val— | Ph(CH₂)₃— | ES+: 733.8 |
| 11 | Et | Fmoc—Val— | 2-phenyl-quinolin-4-yl-CH₂CH₂— | AP+: 666.8 (M − Fmoc + 1, 100%); 888.9 (M + 1, 10%) |
| 12 | Et | 2-chloro-pyridin-3-yl-C(O)-Val— | Ph(CH₂)₃— | ES+: 706.2 |
| 13 | Et | 4-butyl-C₆H₄-C(O)-Val— | Ph(CH₂)₃— | ES+: 727.4 |
| 14 | Et | iBuO-C(O)-Val— | Ph(CH₂)₃— | ES+: 667.2 |

TABLE 1-continued

[Structure: imidazolidinone with R³ on one N, A³ on other N, connected via C(=O)NH-CH(R₁)-B(pinanediol boronate)]

| Ex. | R¹ | A³ | R³ | Mass Spec (M + H, 100%) |
|---|---|---|---|---|
| 15 | Et | PhC(=O)NHC(=O)-Val— | Ph(CH₂)₃— | ES+: 714.3 |
| 16 | Et | (1-Naphthyl)C(=O)-Val— | Ph(CH₂)₃— | ES+: 721.3 |
| 17 | Et | CH₃C(=O)-Val— | Ph(CH₂)₃— | ES+: 631.6 |
| 18 | Et | PhC(=O)-Val— | Ph(CH₂)₃— | ES+: 733.8 |
| 19 | allyl | CBz— | PhCH=CHCH₂— | ES+: 612.5 |
| 20 | Allyl | CBz— | PhNHC(=O)CH₂— | ES+: 628.54 |

Utility

The compounds of Formula (I) are expected to inhibit the activity of Hepatitis C Virus NS3 protease and, therefore, to possess utility in the cure and prevention of HCV infections. The NS3 protease inhibition is demonstrated using assays for NS3 protease activity, for example, using the assay described below for assaying inhibitors of NS3 protease. The compounds of Formula (I) are expected to show activity against NS3 protease in cells, as demonstrated by the cellular assay described below. A compound is considered to be active if it has an $IC_{50}$ value of less than about 100 uM in this assay. It is more preferred if it has an $IC_{50}$ value of less than about 60 uM. It is even more preferred if it has an $IC_{50}$ value of less than about 1 □M. It is most preferred if it has an IC50 value of less than about 0.1uM. Compounds of the present invention have been shown to have an $IC_{50}$ value of less than about 10 uM in this assay.

Expression and Purification of NS3 Protease

The plasmid cf1SODp60O, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (serving as a expression tag) and a 15 amino acid H is tag MRGSHHHHHHMGAQH. The NS3 protease constructs were cloned in the bacterial expression vector under the control of the T7 promoter and transformed in E. coli BL 21 (DE3) cells. Expression of the NS3 protease was obtained by addition of 1 mM IPTG and cells were growing for additional 3 h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 mL/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/mL and cell lysate was incubated at 4° C. for 20 min. After centrifugation at 18,000 rpm for 30 min at 40° C. supernatant was applied on SP Sepharose column (Pharmacia), previously equilibrated at a flow rate 3 mL/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 mL/min, the column was then washed with a buffer A at a flow rate 2 mL/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 mL/min. Enzyme was eluted by applying 20 column volumes of a linear 0.1–0.5 M NaCl gradient. Based on SDS-PAGE analysis as well as HPLC analysis and active site titration, the purity of the HCV NS3a protease was greater than 95%. The enzyme was stored at −70° C. and diluted just prior to use.

Enzyme Assays

Concentrations of protease were determined in the absence of NS4a by using the peptide ester substrate Ac-DED(Edans)EEAbuψ[COO]ASK(Dabcyl)-NH$_2$ (Taliani et al. Anal. Biochem. 240, 60–67, 1996.) and the inhibitor, H-Asp-Glu-Val-Val-Pro-boroAlg-OH (administered as a hydrolyzed compound to the boronic acid), and by using tight binding reaction conditions (Bieth, *Methods Enzymol.* 248, 59–85, 1995). Best data was obtained for an enzyme level of 50 nM. Alternately, protease (63 µg/mL) was allowed to react with 3 µM NS4a, 0.10 mM Ac-Clu-Glu-Ala-Cys-pNA, and varying level of H-Asp-Glu-val-Val-Pro-boroAlg-OH (0–6 µM). Concentrations of protease were determined from linear plots of Activity vs.[inhibitor]. Molar concentrations of proteases were determined from the x-intercept.

$K_m$ values were determined measuring the rate of hydrolysis of the ester substrate over a range of concentrations from 5.0 to 100 µM in the presence of 3 µM KKNS4a (KKGSVVIVGRIVLSGKPAIIPKK). Assay were run at 25° C., by incubating ~1 nM enzyme with NS4a for 5 min in 148 µL of buffer (50 mM Tri buffer, pH 7.0, 50% glycerol, 2% Chaps, and 5.0 mM DTT. Substrate (2.0 1L) in buffer was added and the reaction was allowed to proceed for 15 min. Reactions were quenched by adding 3.0 µL of 10% TFA, and the levels of hydrolysis were determined by HPLC. Aliquots (50 µL) were injected on the HPLC and linear gradients from 90% water, 10% acetonitrile and 0.10% TFA to 10% water, 90% acetonitrile and 0.10% TFA were run at a flow rate of 1.0 mL/min over a period of 30 min. HPLCs were run on a HP1090 using a Rainin 4.6×250 mm C18 column (cat # 83-201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 µm sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 µM was used for all fluorogenic assays run on the spectrometer.

Inhibitor Evaluation In vitro

Inhibitor effectiveness was determined by measuring enzyme activity both in the presence and absence of inhibitor. Velocities were fit to the equation for competitive inhibition for individual reactions of inhibitors with the enzyme using $$v_i/v_o=[K_m(1+I/K_i)+S]/[K_m+S].$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the $IC_{50}$ and $K_i$s are comparable measures of inhibitor effectiveness.

Using the methodology described above, a number of compounds of the present invention were found to exhibit a $K_i$ of $\leq 60$ µM, thereby confirming the utility of the compounds of the present invention as effective NS3 protease inhibitors.

Inhibitor Evaluation in Cell Assay.

The following method was devised to assess inhibitory action of test compounds on the HCV NS3 protease in cultured cells. Because it is not possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease. When installed in cultured cells by one of a variety of standard methods, the substrate plasmid produces a stable polypeptide of approximately 50 KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The general organization of the two plasmids is disclosed in a PCT application PCT/US00/18655. The disclosure of which is hereby incorporated by reference. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 □L of 1% sodium dodecyl sulfate in 0.10 M Tris HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Preparation of H-Asp-Glu-Val-Val-Pro-boroAlg Pinanediol Ester.Trifluoroacetate

Preparation of Boc-Asp(O'Bu)-Glu(O'Bu)-Val-Val-Pro-OH.

Boc-Val-Pro-OBzl was prepared by dissolving H-Pro-OBzl (20 g, 83 mmol) in 50 mL of chloroform and adding Boc-Val-OH (18.0 g, 83 mmol), HOBt (23.0 g, 165 mmol), NMM (9.0 mL, 83 mmol) and DCC (17.0 g, 83 mmol). The reaction mixture was stirred overnight at room temperature. The mixture was filtered and solvent was evaporated. Ethyl acetate was added and insoluble material was removed by filtration. The filtrate was washed with 0.2N HCl, 5% NaHCO$_3$, and saturated aqueous NaCl. It was dried over Na$_2$SO$_4$, filtered and evaporate to give a white solid (30 g, 75 mmol, 90%). ESI/MS calculated for $C_{22}H_{32}N_2O_5$+H: 405.2. Found 405.6.

Boc-Val-Val-Pro-OBzl was prepared by dissolving Boc-Val-Pro-OBzl (14.0 g, 35.0 mmol) in 4N HCl in dioxane (20 mL) and allowing the reaction to stir for 2 h under an inert atmosphere at room temperature. The reaction mixture was concentrated by evaporation in vacuo and ether was added to yield a precipitate. It was collected by filtration under nitrogen. After drying in vacuo with P205, H-Val-Pro-OBzl was obtained as a white solid (22.6 g, 30.3 mmol, 89%). (ESI/MS calculated for $C_{17}H_{24}N_2O_3$+H: 305.2. Found: 305.2.) H-Val-Pro-OBzl (9.2 g, 27 mmol) was dissolved in 50 mL of CH$_2$Cl$_2$ and Boc-Val-OH (7.3 g, 27 mmol), HOBt (7.3 g, 54 mmol), NMM (3.0 mL, 27 mmol) and DCC (5.6 g, 27 mmol) were added. The reaction mixture stirred overnight at room temperature. The mixture was filtered and the filtrate was evaporated. The residue was dissolved in ethyl acetate and the solution was re-filtered. The filtrate was washed with 0.2N HCl, 5% NaHCO$_3$, and saturated aqueous NaCl. It was dried over Na$_2$SO$_4$, filtered and evaporated to give a yellow oil (10.6 g, 21.1=mol, 78%). ESI/MS calculated for $C_{27}H_{41}N_3O_6$+Na: 526.3 Found: 526.4. Z-Glu(O'Bu)-Val-Val-Pro-OBzl was also prepared by DCC coupling. H-Val-Val-Pro-OBzl-hydrochloride was obtained in a 100% yield by treating the corresponding Boc compound with anhydrous HCl using the procedure described for H-Val-Pro-OBzl (ESI/MS calculated for $C_{22}H_{33}N_3O_4$+H: 404.2. Found 404.3.). The amine hydrochloride (7.40 g, 16.8 mmol) was dissolved in 185 mL DMF and 25 mL THF. Z-Glu(O'Bu)—OH (5.60 g, 16.8 mmol), HOBT (4.60 g, 33.6 mmol), NMM (1.85 mL, 16.8 mmol) and DCC (3.5 g, 16.8 mmol) were added. The reaction was run and the product was isolated by the procedure described for Boc-Val-Val-Pro-OBzl. The tetrapeptide was obtained as a white foam (12.0 g, 16.1 mmol, 96%). ESI/MS calculated for $C_{39}H_{54}N_4O_9$+Na: 745.4. Found: 745.4.

H-Glu(O'Bu)-Val-Val-Pro-OH was prepared by dissolving Z-Glu(O'Bu)-Val-Val-Pro-OBzl (2.90 g, 3.89 mmol) in 100 mL methanol containing 1% acetic acid. Pearlman's catalyst, Pd(OH)$_2$, (100 mg) was added and the flask was placed on the Parr hydrogenation apparatus with an initial H$_2$ pressure of 34 psi. After three hours, the catalyst was removed by filtration through a celite pad and the filtrate was evaporated in vacuo to yield a yellow oil (1.30 g, 2.61 mmol. 67%). ESI/MS calculated for $C_{24}H_{42}N_4O_7$+H: 499.3 Found: 499.4.

Boc-Asp(O'Bu)-Glu(O'Bu)-Val-Val-Pro-OH was prepared by active ester coupling. Boc-Asp(O'Bu)—N-hydroxysuccinimide ester was prepared by coupling Boc-Asp(O'Bu)—OH (3.00 g, 10.4 mmol) to N-hydroxysuccinimide (1.19 g, 10.4 mmol) in 50 mL of ethylene glycol dimethyl ether. The reaction flask was placed in an ice bath at 0° C. and DCC was added. The reaction mixture was slowly allowed to warm to room temperature and to stir overnight. The mixture was filtered and the filtrate was evaporated in vacuo. The residue was dissolved in ethyl acetate and re-filtered. The filtrate was evaporated give a white solid. Recrystallized from ethyl acetate:hexane gave the activated ester (3.38 g, 8.80 mmol, 84%). (ESI/MS calculated for $C_{17}H_{26}N_2O_8$+H: 387.2. Found: 387.4.) H-Glu(O'Bu)-Val-Val-Pro-OH (5.40 g, 10.8 mmol) was dissolved in 100 mL of water. Sodium bicarbonate (0.92 g, 11.0 mmol) was added followed by triethylamine (2.30 mL, 16.5 mmol). The N-hydroxysuccinimide ester (3.84 g, 10.0 mmol) was dissolved in 100 mL dioxane and was added to the H-Glu(O'Bu)-Val-Val-Pro-OH solution. The mixture stirred overnight at room temperature. Dioxane was removed in vacuo and 1.0 M HCl was added to give pH ~1. The product was extracted into ethyl acetate. The ethyl acetate solution was washed with 0.2 N HCl, dried over sodium sulfate, filtered, and evaporated to yield a yellow oil (7.7 g, 10.0 mmol, 100%). ESI/MS calculated for $C_{37}H_{63}NSO_{12}$+Na: 792.4. Found: 792.4.

Boc-Asp(O'Bu)-Glu(O'Bu)-Val-Val-Pro-boroAlg-pinanediol was prepared by coupling the protected pentapeptide to H-boroAlg-pinanediol. Boc-Asp(O'Bu)-Glu(O'Bu)-Val-Val-Pro-OH (1.8 g, 2.3 mmol) was dissolved 10 mL THF and was cooled to −20° C. Isobutyl chloroformate (0.30 mL, 2.3 mmol) and NMM (0.25 mL, 2.3 mmol) were added. After 5 minutes, this mixture was added to H-boroAlg-pinanediol (0.67 g, 2.3 mmol) dissolved in THF (8 mL) at −20° C. Cold THF (~5 mL) was used to aid in the transfer. Triethylamine (0.32 mL, 2.3 mmol) was added and the reaction mixture was allowed to come to room temperature and to stir overnight. The mixture was filtered and solvent was removed by evaporation. The residue was dissolved in ethyl acetate, washed with 0.2 N HCl, 5% NaHCO$_3$, and saturated NaCl. The organic phase was dried with Na$_2$SO$_4$, filtered, and evaporated to yield a yellow oil. Half of the crude product (1.5 g) was purified in 250 mg lots by HPLC using a 4 cm×30 cm Rainin C-18 reverse phase column. A gradient from 60:40 acetonitrile: water to 100% acetonitrile was run over a period of 28 minutes at a flow rate of 40 mL/min. The fractions containing the desired product were pooled and lyophilized to yield a white solid (46 mg). $^1$H-NMR (CD$_3$OD) δ 0.9–1.0 (m, 15H), 1.28 (s, 3H), 1.3 (s,3H), 1.44 (3s, 27H), 1.6–2.8 (20H), 3.7(m, 1H), 3.9(m, 1H), 4.1–4.7 (7H), 5.05(m, 2H), 5.9(m, 1H). High res (ESI/MS) calculated for $C_{51}H_{86}N_6O_{13}B1$+H: 1001.635. Found 1001.633.

Preparation of H-Asp-Glu-Val-Val-Pro-boroAlg pinanediol ester.trifluoroacetate: The hexapeptide analog, Boc-Asp(O'Bu)-Glu(O'Bu)-Val-Val-Pro-boroAlg-pinanediol, (22.5 mg, 0.023 mmol) was treated with 2 mL of TFA: CH$_2$Cl$_2$ (1:1) for 2 h. The material was concentrated in vacuo and purified by HPLC using C-18 Vydac reverse phase (2.2×25 cm) column with a gradient starting at 60:40 acetonitrile/water with 0.1%TFA going to 95:5 over 25 minutes with a flow rate of 8 mL/min. The product eluted at 80% acetonitrile. The fractions were evaporated and dried under high vacuum to give 8.9 mg (49%) of the desired product as white amorphous solid. $^1$H-NMR (CD$_3$OD) δ 5.82 (m, 1H), 5.02 (m, 2H), 4.58(m, 1H), 4.42 (m, 3H), 4.18 (m, 4H), 3.90 (m, 1H), 3.62 (m, 1H), 3.01 (dd, 1H), 2.78 (m, 1H), 2.62 (m, 1H), 2.41–1.78 (m, 17H), 1.31 (s, 3H), 1.28 (s, 3H), 1.10–0.82 (m, 15H). ESI/MS calculated for C$_{38}$H$_{62}$N$_{6}$O$_{11}$B+H: 789.2. Found: 789.2.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

Dosage and Formulation

The HCV protease inhibitor compounds of this invention can be administered as treatment for the control or prevention of hepatitis C virus infections by any means that produces contact of the active agent with the agent's site of action, i.e., the NS3 protease, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed:

1. A compound of Formula (I):

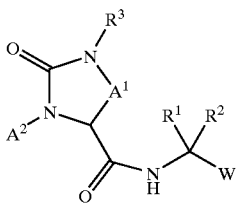

or a stereoisomer, or pharmaceutically acceptable salt form thereof, wherein:

$A^1$ is $C_1$–$C_3$ alkylene substituted by 0–2 $C_1$–$C_4$ alkyl;

$A^2$ is —$A^3$–$R^9a$;

W is -B($OR^{26}$) ($OR^{27}$);

$R^1$ is selected from the group: H, F;
$C_1$–$C_6$ alkyl substituted with 0–3 $R^{1a}$;
$C_2$–$C_6$ alkenyl substituted with 0–3 $R^{1a}$;
$C_2$–$C_6$ alkynyl substituted with 0–3 $R^{1a}$; and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH;

$R^2$ is selected from the group: H, $C_1$–$C_4$ alkyl, $C_2$–$C_4$ alkenyl, $C_2$–$C_4$ alkynyl, $C_3$–$C_4$ cycloalkyl, and $C_3$–$C_4$ cycloalkyl($C_1$–$C_4$ alkyl)-;

$R^3$ is selected from the group: $R^4$,
—$(CH_2)_p NHR^4$,
—$(CH_2)_p$—NHC(=O)—$R^4$,
—$(CH_2)_p$—C(=O)NH—$R^4$,
—$(CH_2)_p$—C(=O)O—$R^4$,
—$(CH_2)_p$—C(=O)C(=O)—$R^4$,
—$(CH_2)_p$—C(=O)C(=O)NH—$R^4$,
—$(CH_2)_p$—NHC(=O)NH—$R^4$,
—$(CH_2)_p$—NHC(=O)NHC(=O)—$R^4$,
—$(CH_2)_p$—NHS(=O)$_2$$R^4$,
—$(CH_2)_p$—S(=O)$_2$NHR$^4$,
—$(CH_2)_p$—C(=O)—$R^4$,
—$(CH_2)_p$—O—$R^4$, and
—$(CH_2)_p$—S—$R^4$;

p is 0, 1, or 2;

$R^4$ is selected from the group:
$C_1$–$C_6$ alkyl substituted with 0–3 $R^{4a}$;
$C_2$–$C_6$ alkenyl substituted with 0–3 $R^{4a}$;
$C_2$–$C_6$ alkynyl substituted with 0–3 $R^{4a}$; and
$C_3$–$C_{10}$ carbocycle substituted with 0–4 $R^{4b}$;

$R^{4a}$ is, at each occurrence, independently selected from: H,
$C_1$–$C_4$ alkyl substituted with 0–3 $R^{4b}$;
$C_2$–$C_4$ alkenyl substituted with 0–3 $R^{4b}$;
$C_2$–$C_4$ alkynyl substituted with 0–3 $R^{4b}$; and
$C_3$–$C_{10}$ carbocycle substituted with 0–4 $R^{4c}$;

$R^{4b}$ is, at each occurrence, independently selected from: H,
$C_1$–$C_4$ alkyl substituted with 0–3 $R^{4c}$;
$C_2$–$C_4$ alkenyl substituted with 0–3 $R^{4c}$;
$C_2$–$C_4$ alkynyl substituted with 0–3 $R^{4c}$;
$C_3$–$C_6$ cycloalkyl substituted with 0–4 $R^{4d}$; and
aryl substituted with 0–5 $R^{4d}$;

$R^{4c}$ is, at each occurrence, independently selected from: H,
$C_1$–$C_4$ alkyl substituted with 0–3 $R^{4d}$;
$C_2$–$C_4$ alkenyl substituted with 0–3 $R^{4d}$;
$C_2$–$C_4$ alkynyl substituted with 0–3 $R^{4d}$;
$C_3$–$C_6$ cycloalkyl substituted with 0–4 $R^{4d}$; and
aryl substituted with 0–5 $R^{4d}$;

$R^{4d}$ is, at each occurrence, independently selected from:
H, F, Cl, Br, I, —$NO_2$, —CN, —NCS, —$CF_3$, —$OCF_3$, =O, OH, $R^{9a}$ is selected from the group: H,
—C(=O)$R^{9b}$, —C(=O)O$R^{9b}$, —C(=O)NH$R^{9b}$, —C(=O)NHC(=O)$R^{9b}$;
$C_1$–$C_6$ alkyl substituted with 0–3 $R^{9c}$;
$C_2$–$C_6$ alkenyl substituted with 0–3 $R^{9c}$; and
$C_2$–$C_6$ alkynyl substituted with 0–3 $R^{9c}$;

$R^{9b}$ is selected from the group: H;
$C_1$–$C_6$ alkyl substituted with 0–3 $R^{9c}$;
$C_2$–$C_6$ alkenyl substituted with 0–3 $R^{9c}$;
$C_2$–$C_6$ alkynyl substituted with 0–3 $R^{9c}$; and
$C_3$–$C_{14}$ carbocycle substituted with 0–4 $R^{9d}$;

$R^{9c}$ is selected from the group:
$C_1$–$C_6$ alkyl substituted with 0–3 $R^{9d}$;
$C_2$–$C_6$ alkenyl substituted with 0–3 $R^{9d}$;
$C_2$–$C_6$ alkynyl substituted with 0–3 $R^{9d}$; and
$C_3$–$C_{14}$ carbocycle substituted with 0–4 $R^{9e}$;

$R^{9d}$ is selected at each occurrence from the group:
$C_1$–$C_4$ alkyl substituted with 0–3 $R^{9e}$;
$C_1$–$C_4$ alkoxy substituted with 0–3 $R^{9e}$;
$C_3$–$C_6$ cycloalkyl substituted with 0–3 $R^{9e}$; and
aryl substituted with 0–5 $R^{9e}$;

$R^{9e}$ is selected at each occurrence from the group:
$C_1$–$C_4$ alkyl, $C_1$–$C_4$ alkoxy, $CF_3$, $OCF_3$, Cl, F, Br, I, =O, OH, phenyl, C(O)O$R^{11}$, $NH_2$, NH($CH_3$), N($CH_3$)$_2$, —CN, and $NO_2$;

$R^{11}$ is selected from the group: H;
$C_1$–$C_6$ alkyl substituted with 0–3 $R^{11b}$;
$C_2$–$C_6$ alkenyl substituted with 0–3 $R^{11b}$;
$C_2$–$C_6$ alkynyl substituted with 0–3 $R^{11b}$;
$C_3$–$C_7$ cycloalkyl substituted with 0–3 $R^{11b}$;
aryl substituted with 0–3 $R^{11b}$; and
aryl($C_1$–$C_4$ alkyl)- substituted with 0–3 $R^{11b}$;

$R^{11b}$ is OH, $C_1$–$C_4$ alkoxy, F, Cl, Br, I, $NH_2$, or —NH($C_1$–$C_4$ alkyl);

$OR^{26}$ and $OR^{27}$, taken together, form a cyclic boronic ester where said cyclic boronic ester contains from 2 to 20 carbon atoms; and $A^3$ is valine.

2. A compound of claim 1, or a stereoisomer, or a pharmaceutically acceptable salt form thereof, wherein:

$A^7$ is —$CH_2$—; $R^1$ is selected from the group: H,
$C_1$–$C_6$ alkyl;
$C_2$–$C_6$ alkenyl; and
$C_2$–$C_6$ alkynyl;

$R^2$ is H;

$R^3$ is selected from the group:
$C_1$–$C_6$ alkyl substituted with phenyl,
$C_1$–$C_6$ alkenyl substituted with phenyl, and
—$CH_2$CONHPh;

and $OR^{26}$ and $OR^{27}$ taken together form pinanediol.

3. A compound of claim 1, or a stereoisomer or pharmaceutically acceptable salt form thereof, selected from the group consisting of (4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-3-methyl-2-[(phenylacetyl)-amino]-butanoyl}-2-oxo-1-(3-phenylpropyl)-4-imidazolidinecarboxamide;

tert-butyl (1S)-N-{[[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl)imidazolidinyl]carbonyl}-2-methylpropylcarbamate;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[(anilinocarbonyl)amino]-3-methylbutanoyl}-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[(9H-fluoren-1-ylcarbonyl) amino]-3-methylbutanoyl}-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-{[(4-methoxyphenyl)acetyl]amino}-3-methylbutanoyl}-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]-3-butenyl}-3-{(2S)-2[(9H-fluoren-1-ylcarbonyl) amino]-3-methylbutanoyl)-2-oxo-1-(3-phenylpropyl)-4-imidazolidinecarboxamide;

9H-fluoren-9-ylmethyl (1S)-N-{[[(1R)-1-[(3αS,4S,6S,7αR) -hexahydro-3α,5,5-trimethyl-4,6-methano-1,3,2-benzodioxaborol-2-yl]propyl)amino)carbonyl]-2-oxo-3-(3-phenylpropyl)imidazolidinyl]carbonyl{-2-methylpropylcarbamate;

(4S)-N-{[[(1R)-1-[(3αS,4S,6S,7αR)-hexahydro-3α,5,5-trimethyl-4,6-methano-1,3,2-benzodioxaborol-2-yl]propyl}-3-((2S)-2-2-{([3- (trifluoromethyl)benzyl]amino}butanoyl)-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[([1,1'-biphenyl]-4-ylmethyl)amino]-3-methylbutanoyl)-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-[(4-butylbenzoyl) amino[-3-methylbutanoyl}-2-oxo-1-(3-phenylpropyl)-4-imidazolidinecarboxamide;

isobutyl (1S)-1-{[(5S)-5-{[[(1R)-1-[(3αS,4S,6S,7αR)-hexahydro-3α,5,5-trimethyl-4,6-methano-1,3,2-benzodioxaborol-2-yl]propyl}amino)carbonyl]-2-oxo-3-(3-phenylpropyl) imidazolidinyl]carbonyl}-2-methylpropylcarbamate;

(4S)-N-{[[(1R)-1-[(3αS,4S,6S,7αR)-hexahydro-3α,5,5-trimethyl-4,6-methano-1,3,2-benzodioxaborol-2-yl)propyl}-3-((2S)-2-{[(benzoylamino)carbonyl]amino}-3-methylbutanoyl)-2-oxo-1-(3--phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-3-methyl-2-(1-naphthoylamino)butanoyl]-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-(acetylamino)-3-methylbutanoyl]-2-oxo-1-(3-phenylpropyl)-4-imidazolidinecarboxamide;

(4S)-N-{[[(1R)-1-[(3αS,4S,6S,7αR)-hexahydro-3α,5,5-trimethyl-4,6-methano-1,3,2-benzodioxaborol-2-yl]propyl}-3-{(2S)-2-(benzoylamino)-3-methylbutanoyl]-2-oxo-1-(3-phenylpropyl)-4-imidazolidinecarboxamide;

benzyl(5S)-5-[({(1R)-1-[(3αS,4S,6S,7αR)-hexahydro-3α,5,5-trimethyl-4,6-methano-1,3,2-benzodioxaborol-2-yl]-3-butenyl}amino)carbonyl]-2-oxo-3-[(2E)-3-phenyl-2-propenyl]-1-imidazolidinecarboxylate; and benzyl (5S)-5-[({(1R)-1-((3αS,4S,6S,7αR)-hexahydro-3α,5,5-trimethyl-4,6-methano-1,3,2-benzodioxaborol-2-yl]-3-butenyl}amino)carbonyl]-3-(2-anilino-2-oxoethyl)-2-oxo-1-imidazolidinecarboxylate.

4. A pharmaceutical composition comprising a pharmaceutically acceptable carrier and a therapeutically effective amount of a compound of claim 1, or a pharmaceutically acceptable salt form thereof.

* * * * *

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 1

Met Gly Ala Gln His
1               5

<210> SEQ ID NO 2
<211> LENGTH: 15
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 2

Met Arg Gly Ser His His His His His His Met Gly Ala Gln His
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Peptide ester substrate synthesized by methods
      disclosed in Taliani et al., Anal. Biochem., 240, 60-67, 1996.
<220> FEATURE:
<221> NAME/KEY: ACETYLATION
<222> LOCATION: (1)..(1)
<223> OTHER INFORMATION: acetyl group
<220> FEATURE:
<221> NAME/KEY: MOD_RES
<222> LOCATION: (3)..(3)
<223> OTHER INFORMATION: Aspartic acid modified with EDANS,
      5-[(2'-aminoethyl)amino]naphthylene sulfonic acid
<220> FEATURE:
<221> NAME/KEY: MISC_FEATURE
<222> LOCATION: (6)..(6)
<223> OTHER INFORMATION: 2-amino butyric acid bonded through an ester
      group
<220> FEATURE:
<221> NAME/KEY: MOD_RES
<222> LOCATION: (9)..(9)
<223> OTHER INFORMATION: Lysine modified by Dabcyl;
      4-[[4'(dimethylamino)phenyl]azo]benzoic acid

<400> SEQUENCE: 3

Asp Glu Asp Glu Glu Xaa Ala Ser Lys
1               5

<210> SEQ ID NO 4
<211> LENGTH: 4
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: ACETYLATION
<222> LOCATION: (1)..(1)

```
<223> OTHER INFORMATION: Acetylation
<220> FEATURE:
<221> NAME/KEY: AMIDATION
<222> LOCATION: (4)..(4)
<223> OTHER INFORMATION: para-nitroanaline

<400> SEQUENCE: 4

Glu Glu Ala Cys
1

<210> SEQ ID NO 5
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MISC_FEATURE
<222> LOCATION: (6)..(6)
<223> OTHER INFORMATION: Boro-allylglyycine

<400> SEQUENCE: 5

Asp Glu Val Val Pro Xaa
1               5

<210> SEQ ID NO 6
<211> LENGTH: 23
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 6

Lys Lys Gly Ser Val Val Ile Val Gly Arg Ile Val Leu Ser Gly Lys
1               5                   10                  15

Pro Ala Ile Ile Pro Lys Lys
            20

<210> SEQ ID NO 7
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MISC_FEATURE
<222> LOCATION: (6)..(6)
<223> OTHER INFORMATION: Boro-allylglycine pinanediol ester

<400> SEQUENCE: 7

Asp Glu Val Val Pro Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: t-Butoxycarbonyl
      Delta-Carboxy Ester: t-Butyl
<220> FEATURE:
```

```
<221> NAME/KEY: MOD_RES
<222> LOCATION: (2)..(2)
<223> OTHER INFORMATION: Gamma-Carboxy Ester: t-Butyl

<400> SEQUENCE: 8

Asp Glu Val Val Pro
1               5

<210> SEQ ID NO 9
<211> LENGTH: 4
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: benzyloxycarbonyl
      Gamma-Carboxy Ester: t-Butyl
<220> FEATURE:
<221> NAME/KEY: MOD_RES
<222> LOCATION: (4)..(4)
<223> OTHER INFORMATION: Benzyl Esterfication

<400> SEQUENCE: 9

Glu Val Val Pro
1

<210> SEQ ID NO 10
<211> LENGTH: 4
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: Gamma-Carboxy Ester: t-Butyl

<400> SEQUENCE: 10

Glu Val Val Pro
1

<210> SEQ ID NO 11
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: t-Butoxycarbonyl
      Delta-Carboxy Ester: t-Butyl
<220> FEATURE:
<221> NAME/KEY: MOD_RES
<222> LOCATION: (2)..(2)
<223> OTHER INFORMATION: Gamma-Carboxy Ester: t-Butyl
<220> FEATURE:
<221> NAME/KEY: MISC_FEATURE
<222> LOCATION: (6)..(6)
<223> OTHER INFORMATION: Boro-allylglycine pinanediol ester

<400> SEQUENCE: 11

Asp Glu Val Val Pro Xaa
1               5
```